(12) United States Patent
Fiorina et al.

(10) Patent No.: US 12,221,485 B2
(45) Date of Patent: Feb. 11, 2025

(54) TMEM219 ANTIBODIES AND THERAPEUTIC USES THEREOF

(71) Applicant: ENTHERA S.R.L., Milan (IT)

(72) Inventors: Paolo Fiorina, Boston, MA (US); Giovanni Amabile, Milan (IT); Francesca D'Addio, Milan (IT)

(73) Assignee: ENTHERA S.R.L., Milan (IT)

( * ) Notice: Subject to any disclaimer, the term of this patent is extended or adjusted under 35 U.S.C. 154(b) by 0 days.

(21) Appl. No.: 18/772,062

(22) Filed: Jul. 12, 2024

(65) Prior Publication Data
US 2024/0368290 A1    Nov. 7, 2024

Related U.S. Application Data

(63) Continuation of application No. 17/777,021, filed as application No. PCT/EP2020/082292 on Nov. 16, 2020.

(30) Foreign Application Priority Data

Nov. 15, 2019 (EP) ..................................... 19209521
Apr. 1, 2020 (EP) ..................................... 20167459

(51) Int. Cl.
   *C07K 16/28*        (2006.01)
   *A61P 3/10*         (2006.01)
   *C12N 15/63*       (2006.01)

(52) U.S. Cl.
CPC ............ *C07K 16/2863* (2013.01); *A61P 3/10* (2018.01); *C12N 15/63* (2013.01); *C07K 2317/24* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 10,682,391 B2 * | 6/2020 | D'Addio | A61P 1/04 |
| 11,020,453 B2 * | 6/2021 | D'Addio | A61K 31/713 |
| 2018/0169184 A1 | 6/2018 | D'Addio et al. | |
| 2018/0172708 A1 | 6/2018 | D'Addio et al. | |
| 2018/0243367 A1 | 8/2018 | D'Addio et al. | |
| 2020/0316168 A1 | 10/2020 | D'Addio et al. | |
| 2021/0169973 A1 | 6/2021 | D'Addio et al. | |
| 2021/0388072 A1 | 12/2021 | Fiorina et al. | |
| 2023/0039165 A1 | 2/2023 | Amabile et al. | |
| 2023/0192827 A1 | 6/2023 | Amabile et al. | |

FOREIGN PATENT DOCUMENTS

| | | | | |
|---|---|---|---|---|
| EP | 3302564 B1 * | 10/2019 | | A61K 31/713 |
| EP | 3632929 A1 * | 4/2020 | | C07K 16/005 |
| WO | WO 98/029451 A1 | 7/1998 | | |
| WO | WO 2016/193496 A1 | 12/2016 | | |
| WO | WO-2016193497 A1 * | 12/2016 | | A61K 31/713 |
| WO | WO-2018085252 A1 * | 5/2018 | | A61K 38/17 |
| WO | WO 2020/070224 A1 | 4/2020 | | |
| WO | WO 2021/099574 A1 | 5/2021 | | |
| WO | WO-2021094620 A1 * | 5/2021 | | A61K 39/0008 |
| WO | WO 2021/165499 A1 | 8/2021 | | |

OTHER PUBLICATIONS

D'Addio, F. et al., "Autologous nonmyeloablative hematopoietic stem cell transplantation in new-onset type 1 diabetes: a multicenter analysis," Diabetes, 2014, vol. 63, pp. 3041-3046.
D'Addio, F., et al., "Circulating IGF-I and IGFBP3 levels control human colonic stem cell function and are disrupted in diabetic enteropathy," Cell Stem Cell, Oct. 1, 2015, vol. 17, No. 4, pp. 486-498.
D'Addio, F., Maestroni, A., Assi, E. et al. The IGFBP3/TMEM219 pathway regulates beta cell homeostasis. Nat Commun 13, 684, Feb. 3, 2022, pp. 1-14.
Fiorina, P. et al., "Effects of kidney-pancreas transplantation on atherosclerotic risk factors and endothelial function in patients with uremia and type 1 diabetes," Diabetes, 2001, vol. 50, pp. 496-501.
Fiorina, P. et al., "Long-term beneficial effect of islet transplantation on diabetic macro-/microangiopathy in type 1 diabetic kidney-transplanted patients," Diabetes Care, 2003, vol. 26, pp. 1129-1136.
Fiorina, P. et al., "Natural history of kidney graft survival, hypertrophy, and vascular function in end-stage renal disease type 1 diabetic kidney-transplanted patients: beneficial impact of pancreas and successful islet cotransplantation," Diabetes Care, 2005, vol. 28, pp. 1303-1310.
Fiorina, P. et al., "Normalization of multiple hemostatic abnormalities in uremic type 1 diabetes patients after kidney-pancreas transplantation," Diabetes, 2004, vol. 53, pp. 2291-2300.
Atkinson, M.A. et al., "Current concepts on the pathogenesis of type 1 diabetes-considerations for attempts to prevent and reverse the disease," Diabetes Care, 2015, vol. 38, pp. 979-988.
Baxter, R., "IGF binding proteins in cancer: mechanistic and clinical insights," Nature Reviews, 2014, vol. 14, pp. 329-341.
Baxter, R.C., "Insulin-like growth factor binding protein-3 (IGFBP-3): Novel ligands mediate unexpected functions," J Cell Commun Signal, 2013, vol. 7, pp. 179-189.
Dall'Acqua, W.F. et al., "Properties of Human IgG1s Engineered for Enhanced Binding to the Neonatal Fc Receptor (FcRn)*," The Journal of Biological Chemistry, 2006, vol. 281, No. 33, pp. 23514-23524.
Drogan, D. et al., "Insulin-Like Growth Factor 1 and Insulin-Like Growth Factor-Binding Protein 3 in Relation to the Risk of Type 2 Diabetes Mellitus: Results from the EPIC-Potsdam Study," Am J Epidemiol, 2016, vol. 183, No. 6, pp. 553-560.

(Continued)

*Primary Examiner* — Marianne P Allen
(74) *Attorney, Agent, or Firm* — Fenwick & West LLP

(57) ABSTRACT

The present invention relates to antibodies or antigen binding fragments thereof that bind specifically to the IGFBP3 receptor, namely TMEM219, to methods for their production, pharmaceutical compositions containing said antibodies, and uses thereof.

22 Claims, 10 Drawing Sheets
(7 of 10 Drawing Sheet(s) Filed in Color)
Specification includes a Sequence Listing.

(56) References Cited

OTHER PUBLICATIONS

Flynn, R.S. et al., "Endogenous IGFBP-3 regulates excess collagen expression in intestinal smooth muscle cells of Crohn's disease strictures," Inflammatory Bowel Diseases, vol. 17, No. 1, Jan. 1, 2011, pp. 193-201.
Forbes, K. et al., "Transforming growth factor-β (TGFβ) receptors I/II differentially regulate TGFβ1 and IGF-binding protein-3 mitogenic effects in the human placenta," Endocrinology, 2010, vol. 151, pp. 1723-1731.
International Preliminary Report on Patentability Chapter II, Patent Cooperation Treaty Application No. PCT/EP2016/062792, May 23, 2017, 10 pages.
International Search Report and Written Opinion, Patent Cooperation Treaty Application No. PCT/EP2016/062790, Sep. 26, 2016, 12 pages.
International Search Report and Written Opinion, Patent Cooperation Treaty Application No. PCT/EP2016/062792, Sep. 30, 2016, 9 pages.
International Search Report and Written Opinion, Patent Cooperation Treaty Application No. PCT/EP2019/076771, Mar. 16, 2020, 27 pages.
International Search Report and Written Opinion, Patent Cooperation Treaty Application No. PCT/EP2020/082890, Feb. 22, 2021, 13 pages.
International Search Report and Written Opinion, Patent Cooperation Treaty Application No. PCT/EP2021/054215, dated Apr. 19, 2021, 11 pages.
Katsanos, K.H. et al., "Reduced serum insulin-like growth factor-1 (IGF-1) and IGF-binding protein-3 levels in adults with inflammatory bowel disease," Growth Hormone & IGF Research, 2001, vol. 11, pp. 364-367.
Keenan, H.A. et al., "Residual insulin production and pancreatic β-cell turnover after 50 years of diabetes: Joslin Medalist Study," Diabetes, 2010, vol. 59, No. 11, pp. 2846-2853.
Kim, KS, et al., "Induction of Cellular Senescence by Insulin-like Growth Factor Binding Protein-5 through a p53-dependent Mechanism," *Molecular Biology of the Cell*, vol. 18, No. 11, DOI:10.2091/MBC.E07-03-0280, Sep. 2007, p. 4543-4552, Retrieved from the Internet: URL:https://www.ncbi.nlm.nih.gov/pmc/articles/PMC2043568/pdf/zmk4543.pdf, Abstract, p. 4545, right-hand column last paragraph through p. 4547, left-hand column, 1st paragraph, figures 1 and 2, p. 4549, left-hand column, last paragraph through right-hand column, 1st paragraph.
Kirman, I. et al., "Insulin-like Growth Factor Binding Protein 3 in Inflammatory Bowel Disease," Digestive Diseases and Sciences, Apr. 2005, vol. 50, No. 4, pp. 780-784.
Kuemmerle, J.F. et al., "IGFBP-3 actives TFG-β receptors and directly inhibits growth in human intestinal smooth muscle cells," Am J Physiol Gastrointest Liver Physiol, Jun. 3, 2004, vol. 287, pp. G795-G802.
Lee, C-M. et al., "IL-13Rα2 uses TMEM219 in chitinase 3-like-1-induced signalling and effector responses," Nature Communications 7:12752, Sep. 15, 2016, pp. 1-12.
Melone, M.A.B., et al., "Increased expression of IGF-binding protein-5 in Duchenne muscular dystrophy (DMD) fibroblasts correlates with the fibroblast induced downregulation of DMD myoblast growth: an in vitro analysis," *Journal of Cellular Physiology, Wiley Subscription Services, Inc, US*, vol. 185, Jan. 2000, p. 143-153, abstract, p. 145, last paragraph, p. 136, 2nd paragraph, p. 148, left-hand column 1st paragraph through p. 149, right-hand column, 1st paragraph.
Müllberg at al., "The soluble interleukin-6 receptor is generated by shedding," *European Journal of Immunology*, vol. 23, Issue 2, Feb. 1993, pp. 473-480.
Munoz, J. et al., "The Igr5 intestinal stem cell signature: robust expression of proposed quiescent '+4' cell markers," EMBO J, 2012, vol. 31, pp. 3079-3091.

Muzumdar, R., et al., "Central and Opposing Effects of IGF-1 and IGF-Binding Protein-3 on Systemic Insulin Action," Diabetes, Oct. 2006, vol. 55, pp. 2788-2796.
Nano, R. et al., "Islet isolation for alltransplantation: variables associated with successful islet yield and graft function," Diabetologia, 2005, vol. 48, pp. 906-912.
Nathan, D.M., "Diabetes: Advances in Diagnosis and Treatment," Jama, 2015, vol. 314, pp. 1052-1062.
Nguyen, K.H. et al., "Human IGF Binding Protein-3 Overexpression Impairs Glucose Regulation in Mice via an Inhibition of Insulin Secretion," Endocrinology, 2011, vol. 152, No. 6, pp. 2184-2196.
Oh, Y. et al., "Antiproliferative actions of insulin-like growth factor binding protein (IGFBP)-3 in human breast cancer cells," Prog Growth Factor Res, 1995, vol. 6, pp. 503-512.
Oilinki, T. et al., "Prevalence and characteristics of diabetes among Somali children and adolescents living in Helsinki, Finland," Pediatric Diabetes, 2012, vol. 13, pp. 176-180.
Pambianco, G. et al. "The 30-year natural history of type 1 diabetes complications: the Pittsburgh Epidemiology of Diabetes Complications Study experience," Diabetes, 2006, vol. 55, pp. 1463-1469.
Peet, A. et al., "Circulating IGF1 and IGFBP3 in relation to the development of β-cell autoimmunity in young children," Eur J Endocrinol, 2015, vol. 173, No. 2, pp. 129-137.
Petkova, S.B. et al., "Enhanced half-life of genetically engineered human IgG1 antibodies in a humanized FcRn mouse model: potential application in humorally mediated autoimmune disease," International Immunology, 2006, vol. 18, No. 12, pp. 1759-1769.
Petrelli, A. et al., "IL-21 is an antitolerogenic cytokine of the late-phase alloimmune response," Diabetes, 2011, vol. 60, pp. 3223-3234.
Piscaglia, A.C. et al., "Circulating hematopoietic stem cells and putative intestinal stem cells in coeliac disease," Journal of Translational Medicine, 2015, vol. 13, pp. 220.
Pithadia, A.B. et al., "Treatment of inflammatory bowel disease (IBD)" Pharmacological Reports, 2011, vol. 63, pp. 629-642.
Pupim, L.B. et al., "Accelerated lean body mass loss in incident chronic dialysis patients with diabetes mellitus," Kidney Int, 2005, vol. 68, pp. 2368-2374.
Remes-Troche, J.M., et al., "Rectoanal reflexes and sensorimotor response in rectal hyposensitivity," Diseases of the Colon and Rectum, 2010, vol. 53, pp. 1047-1054.
Sato, T. et al., "Growing self-organizing mini-guts from a single intestinal stem cell: mechanism and applications," Science, 2013, vol. 340, pp. 1190-1194.
Schonhoff, S.E. et al., "Minireview: Development and Differentiation of Gut Endocrine Cells," Endocrinology, 2004, vol. 145, pp. 2639-2644.
Schwartz, G.P. et al., "A superactive insulin: [B10 Aspartic acid]insulin(human)," Proc Natl Acad Sci, Sep. 1987, vol. 84, pp. 6408-6411.
Schwarz, P.E. et al., "Nonpharmacological interventions for the prevention of type 2 diabetes mellitus," Nature Reviews Endocrinology, 2012, vol. 8, pp. 363-373.
Secchi, A. et al., "Cardiovascular disease and neoplasms after pancreas transplantation," Lancet, 1998, vol. 352, pp. 65-66.
Senger, S. et al., "Celiac Disease Histopathology Recapitulates Hedgehog Downregulation, Consistent with Wound Healing Processes Activation," PloS One, 2015, vol. 10, pp. e0144634.
Smets, Y.F. et al., "Effect of simultaneous pancreas-kidney transplantation on mortality of patients with type-1 diabetes mellitus and end-stage renal failure," Lancet, 1999, vol. 1915-1919.
Spinelli, A. et al. "Intestinal fibrosis in Crohn's disease: medical treatment or surgery?" Current Drug Targets, 2010, vol. 11, No. 2, pp. 242-248.
Sridhar, S.S. et al., "Insulin-insulin-like growth factor axis and colon cancer," J Clin Oncol, 2009, vol. 27, pp. 165-167.
Stange, D.E. et al., "Concise review: the yin and yang of intestinal (cancer) stem cells and their progenitors," Stem Cells, 2013, vol. 31, pp. 2287-2295.
Svedlund, J. et al., "GSRS—a clinical rating scale for gastrointestinal symptoms in patients with irritable bowel syndrome and peptic ulcer disease," Digestive diseases, 1988, vol. 33, pp. 129-134.

(56) References Cited

OTHER PUBLICATIONS

Taghipour, N. et al., "An experimental model of colitis induced by dextran sulfate sodium from acute progresses to chronicity in C57BL/6: correlation between conditions of mice and the environment," Gastroenterology and Hepatology from Bed to Bench, 2016, vol. 9, No. 1, pp. 45-52.
Talley, N.J. et al., "Impact of chronic gastrointestinal symptoms in diabetes mellitus on health-related quality of life," Am J Gastroenterol, 2001, vol. 96, pp. 71-76.
The Diabetes Control and Complications Research Group, "The effect of intensive treatment of diabetes on the development and progression of long-term complications in insulin-dependent mellitus," N Engl J Med, Sep. 30, 1993, vol. 329, pp. 977-986.
Tomlinson, I.M. et al., "The repertoire of human germline VH sequences reveals about fifty groups of VH segments with different hypervariable loops," Journal of Molecular Biology, 1992, vol. 227, No. 3, pp. 776-798.
United States Office Action, U.S. Appl. No. 16/855,992, filed Apr. 12, 2021, fourteen pages.
United States Office Action, U.S. Appl. No. 17/174,893, filed Sep. 20, 2023, 14 pages.
Van Der Flier, L.G. et al., "Stem cells, self-renewal, and differentiation in the intestinal epithelium," Annual Review of Physiology, 2009, vol. 71, pp. 241-290.
Venepalli, N.K. et al., "Phase I Study of IGF-Methotrexate Conjugate in the Treatment of Advanced Tumors Expressing IGF-1 R," American Journal of Clinical Oncology, Nov. 2019, vol. 42, No. 11, pp. 862-869.
Vergani, A. et al., "A novel clinically relevant strategy to abrogate autoimmunity and regulate alloimmunity in NOD mice," Diabetes, 2010, vol. 59, pp. 2253-2264.
Vergani, A. et al., "Effect of the purinergic inhibitor oxidized ATP in a model of islet allograft rejection," Diabetes, 2013, vol. 62, pp. 1665-1675.
Wang, S. et al., "Circulating IGF-1 promotes prostate adenocarcinoma via FOXO31/BIM signaling in a double-transgenic mouse model," Oncogene, Jul. 16, 2019, vol. 38, pp. 6338-6353.
Wang, Z. et al., "Integrin targeted drug and gene delivery," *Expert Opinion on Drug Delivery*, 2010, vol. 7, No. 2, pp. 159-171.
Williams, A.C. et al., "Insulin-like growth factor binding protein 3 (IGFBP-3) potentiates TRAIL-induced apoptosis of human colorectal carcinoma cells through inhibition of NF-kappaB," Cell Death Differ, 2007, vol. 14, pp. 137-145.
Wright, A. et al., "Effect of glycosylation on antibody function: implications for genetic engineering," Trends in Biotechnology, 1997, vol. 15, No. 1, pp. 26-32.
Wright, C.S., et al., "Cell motility in models of wounded human skin is improved by Gap27 despite raised glucose, insulin and IGFBP-5," *Experimental Cell Research*, vol. 319, Issue 4, Feb. 15, 2013, , p. 390-401, DOI: 10.1016/j.yexcr.2012.12.013, ISSN:0014-4827, Abstract, p. 391, left-hand column, paragraph 2; p. 393, right-hand column, paragraph 2, figure 2, figure 3, p. 398, right-hand column, paragraph 3.
Wu, M.J. et al., "Colonic transit time in long-term dialysis patients," Am J Kidney Dis, 2004, vol. 44, pp. 322-327.
Yakar, S. et al., "Serum complexes of insulin-like growth factor-1 modulate skeletal integrity and carbohydrate metabolism," FASEB J, 2009, vol. 23, No. 3, pp. 709-719.
Yancu, D. et al., "A phenotype of IGFBP-3 knockout mice revealed by dextran sulfate-induced colitis," Journal of gastroenterology and hepatology, 2017, vol. 32, No. 1, pp. 146-153.
Yeung, Y.A. et al., "Engineering Human IgG1 Affinity to Human Neonatal Fc Receptor: Impact of Affinity Improvement on Pharmacokinetics in Primates," The Journal of Immunology, 2009, vol. 182, No. 12, pp. 7663-7671.
Yi, P. et al., "Perspectives on the activities of ANGPTL8/betatrophin," Cell, 2014, vol. 159, pp. 467-468.
Zahnd, C. et al., "A Designed Ankyrin Repeat Protein Evolved to Picomolar Affinity to Her2," J Mol Biol, 2007, vol. 369, pp. 1015-1028.
Zeki, S.S. et al., "Stem cells and their implications for colorectal cancer," Nature Reviews, Gastroenterology & Hepatology, 2011, vol. 8, pp. 90-100.
Zhao, J. et al., "Biomechanical and morphometric intestinal remodelling during experimental diabetes in rats," Diabetologia, 2003, vol. 46, pp. 1688-1697.
Ziegler, A.G. et al., "Seroconversion to multiple islet autoantibodies and risk of progression to diabetes in children," Jama, 2013, vol. 309, pp. 2473-2479.
Ziskin, J.L. et al., "In situ validation of an intestinal stem cell signature in colorectal cancer," Gut, 2013, vol. 62, pp. 1012-1023.

* cited by examiner p<0.01 vs. IGFBP3 * p<0.001 vs. IGFBP3
(n=3 experiments)

* p<0.05 vs. T1D ** p<0.01 vs. T1D
(n=3 experiments)

N=3 experiments
***P < 0.001 vs. IGFBP3

N=3 experiments
***P < 0.001 vs. IGFBP3; *p < 0.05

N=3 experiments
**P < 0.01 vs. T1D serum; *p < 0.05 vs T1D serum

N=3 experiments
**P < 0.001 vs. T1D serum

** p<0.01 IGFBP3 vs untreated

Experiments performed in triplicates in Beta-lox5 cultured for 72 h

**** p<0.0001 IGFBP3 vs untreated, TM1, TC01;
**p<0.01 IGFBP3 vs. antiTMEM219 commercial Experiments performed in triplicates in Beta-lox5 cultured for 72 h

TMEM219 ANTIBODIES AND THERAPEUTIC USES THEREOF

CROSS-REFERENCE TO RELATED APPLICATIONS

This application is a continuation of U.S. patent application Ser. No. 17/777,021, filed on May 14, 2022, which is the National Stage of International Application No. PCT/EP2020/082292, filed on Nov. 16, 2020, which claims priority to European Patent Application Serial No. 19209521.4, filed on Nov. 15, 2019, and European Patent Application Serial No. 20167459.5, filed on Apr. 1, 2020.

SEQUENCE LISTING

The instant application contains a Sequence Listing which has been submitted electronically via Patent Center and is hereby incorporated by reference in its entirety. Said XML copy, created on Jul. 12, 2024, is named 59235_US_005USC1_SL.xml, and is 241,509 bytes in size.

TECHNICAL FIELD

The present invention relates to antibodies or antigen binding fragments thereof that bind specifically to the IGFBP3 receptor, namely TMEM219, to methods for their production, pharmaceutical compositions containing said antibodies, and uses thereof.

BACKGROUND ART

IGFBP3/TMEM219 Axis

The insulin-like growth factor binding proteins is a family of seven binding proteins which modulate the bioavailability of insulin-like growth factors (IGFs). Among them IGFBP3 is the most abundant, being present in almost all tissues, and has the higher affinity for IGFs; indeed, approximately 80-90% of IGFs are bound to IGFBP3 in a ternary complex with the acid labile subunit (ALS) (1).

In addition to its ability to regulate IGFs availability, IGFBP3 has also been shown to have IGF-independent functions (2). Indeed, it is able to associate with cell-surface proteins, cell-surface receptors with integral signaling capacity, intracellular and nuclear proteins (transcription factors) thus influencing cell growth and directly inducing apoptosis (2). Among death receptors, TMEM219, a single-span membrane protein, was shown high binding to IGFBP-3 (3). Binding of IGFBP3 to TMEM219 induces caspase-8-mediated apoptosis in a variety of cells, including cancer cells (i.e. prostate and breast) (3), but also stem cells (i.e. colonic stem cells) (4). Blocking or enhancing IGFBP3/TMEM219 axis with different strategies has been shown to respectively prevent or increase cell death. To the best of our knowledge there are no monoclonal antibodies against TMEM219 or IGFBP3 commercially available capable of preventing the IGFBP3/TMEM219 binding and halting the IGF-I independent and Caspase8-mediated detrimental effects on target tissues/cells of binding of IGFBP3 to TMEM219.

IGFBP3/TMEM219 axis in diabetes Type 1 (T1D) and type 2 diabetes (T2D) are both characterized by a loss of beta cells, which results in a reduced secretion of insulin, failure to control blood glucose levels and hyperglycemia (5,6). Despite different etiological mechanisms, either autoimmune response in T1D or insulin resistance/inflammation in T2D, both lead to a progressive reduction of beta cell mass. Indeed, it is becoming evident that the occurring autoimmune activation does not appear sufficient to fully explain beta cell loss in T1D (5). Moreover, the failure of immunotherapies to cure T1D (7) highlighted that: (i) autoimmunity may not be the sole factor involved in T1D pathogenesis and (ii) alternative strategies that target different mechanisms of disease, such as beta cell loss, are needed in order to establish an effective treatment for T1D. The observation that scattered beta cells are detected in individuals with long-standing T1D(8) confirms that either new beta cells must be occurring in order to preserve the beta cell turnover (5, 9), or the destroyed beta-cells may be "different" and prone to death (10). This may suggest that the up/down-regulated expression of surface beta cell receptors may have a key role in making them visible to immune system and, more importantly, that other non-immunological determinants may modulate beta cell fate and function. Therefore, preventing the non-immunological beta cell destruction in T1D and the progressive loss of beta cells in T2D may skew the balance between beta cell generation and destruction towards the recovery of the appropriate beta cell mass, thus paving the way for novel therapeutic approaches capable of halting or delaying the very first phase of the disease. It has been shown that TMEM219, the IGFBP3 receptor, is expressed in a beta cell line and in human/murine islets, and that its ligation is toxic to beta cells. Interestingly, it has been also observed that mice transgenic for human IGFBP3 develop hyperglycemia, exhibit a reduced islets mass and show a decrease response to insulin-glucose stimulation (11), while those knocked down for IGFBP3 did not show any alteration in terms of glycometabolic control (12).

In humans, Drogan and colleagues recently published that elevated circulating levels of IGFBP3 are associated with the development of T2D (13). Moreover, a recent study by the Diabimmune Study group demonstrated that IGFBP3 levels correlate with autoantibody positivity and chance to seroconversion in children at risk for T1D, thus suggesting a role for circulating IGFBP3 in the early development of beta cell autoimmunity (14).

TMEM219, the IGFBP3 receptor, has been already described as a death receptor, whose activation triggers Caspase8-mediated apoptosis within the target cells thus leading to their loss (4).

IGFBP3/TMEM219 Axis in Inflammatory Bowel Disease

Intestinal stem cells (ISCs) reside at the bottom of small and large intestine crypts and control the crypts regeneration and turnover. In particular, ISCs can differentiate along the crypts to generate goblet cells, enterocytes, enteroendocrine cells (4).

Inflammatory bowel disease (IBD) is an immune-mediated chronic condition that encompasses two clinical entities, Crohn's disease (CD) and ulcerative colitis (UC), and affects nearly 2.5 million of individuals in Europe and 1 million in USA (15). The pathogenesis of IBD is still under investigation, but recent evidences suggest that an impaired differentiation of ISCs towards Paneth cells, in ileal CD, and towards goblet cells in UC, may play a key-role in the onset of the disease. In particular, local signaling and inflammatory pathways in the mucosa both respond to external stimuli and preserve ISCs number and function, thus maintaining intestinal homeostasis (16). Indeed recently, Yancu et al., published results that support the role of IGFBP-3 in CD. Indeed, they demonstrated that, the knockout of IGFBP3 has a role in modulating inflammation in the Dextran-Sodium-Sulphate (DSS) colitis murine model (17).

The inventors have recently found that the insulin-like growth factor binding protein 3 (IGFBP3) receptor, namely the TMEM219 receptor, is expressed on ISCs and that its interaction with the circulating hormone IGFBP3 controls ISCs fate and function in a model of intestinal disorders in diabetes and diabetic enteropathy (4). Since diabetic enteropathy and IBD share common features, as alteration in intestinal stem cell (ISC) homeostasis and altered mucosa morphology, these results may add important insights in the still unknown IBD pathogenesis and will possibly lead to the introduction of a new therapeutic approach for IBD treatment.

Current available therapy for IBD is based on the use of anti-inflammatory and immunotherapeutic strategies, which are aggravated by several adverse effects and whose effectiveness in the long-term remains questionable. Surgery is also successfully employed in advanced state of the disease especially in UC (15). Relapsing of the disease mostly in CD is also frequent, thus highlighting the need for a different therapeutic approach. As a result, the identification of novel therapeutic targets and strategies in the treatment of IBD is of a high clinically relevance and need for the health community.

WO2016193497 and WO2016193496 (incorporated herein by reference in their entireties), describe a TMEM219 extracellular domain, ecto-TMEM, acting as an effective therapeutic agent. However, receptor constructs are less desirable as therapeutic agents than are antibodies. Therefore, there is still a need for further therapeutics agents, as antibodies or derivatives thereof, that mimic the effects of ecto-TMEM.

SUMMARY OF THE INVENTION

Disclosed herein are antibodies that bind with high affinity and specificity to human ecto-TMEM (extracellular domain of TMEM) and that are capable of reducing or abrogating binding of IGFBP3 to its cognate receptor, TMEM219, without themselves activating the TMEM219 pathway upon binding. Such neutralizing antibodies are useful in treating disorders in which IGFBP3 binding to TMEM219 contributes to the pathophysiology of the disease, including diabetic enteropathy, inflammatory bowel disease (IBD) such as ulcerative colitis and Crohn's disease, type 1 or type 2 diabetes. Such neutralizing antibodies provide advantageous therapeutic agents that have therapeutic activities similar to the receptor-based ligand trap, ecto-TMEM219.

In a first aspect, it is provided an isolated antibody or antigen binding fragment thereof that binds to human TMEM219 and inhibits or reduces the binding of IGFBP3 to said TMEM219 receptor.

Preferably the isolated antibody or antigen binding fragment thereof inhibits, reduces, or neutralizes the activation of the TMEM219 receptor induced by binding of IGFBP3.

Activation of the TMEM219 receptor induced by IGFBP3 may be measured by any known method in the art or as described below. In particular, IGFBP3-induced activation of a TMEM219 receptor may be measured by measuring apoptosis increase as described therein or decrease in minigut growth as known in the art and described in several publications (4, 18, 27, 28).

Preferably the isolated antibody or antigen binding fragment thereof does not activate TMEM219 pathway upon binding to human TMEM219.

In a preferred embodiment the isolated antibody or antigen binding fragment thereof is effective in preserving beta cells in diabetic subject and/or in preventing islet destruction, and/or in controlling blood glucose levels in an in vivo model.

In a preferred embodiment the isolated antibody or antigen binding fragment thereof is effective in reducing acute colitis in an in vivo model.

In a preferred embodiment the isolated antibody or antigen binding fragment thereof decreases DSS-induced increase in DAI score and histological score or is effective in reducing acute colitis in an in vivo model.

The present invention also provides an isolated antibody or antigen binding fragment thereof that has at least one activity selected from:
- a—increase in IGFBP3 treated healthy subject minigut growth
- b—increase in IBD-patient minigut growth;
- c—increase in diabetic enteropathy serum treated healthy subject minigut growth;
- d—increase in expression of EphB2 and/or LGR5 in IGFBP3 treated healthy subject minigut;
- e—decrease in caspase 8 expression in IGFBP3 treated healthy subject minigut;
- f—decrease in β-cell loss in IGFBP3 treated β-cell;
- g—increase in expression of insulin in IGFBP3 treated β-cell;
- h—inhibits or decreases DSS-induced intestinal cells apoptosis;
- i—restores expression of PCNA in DSS-treated colon;
- j—decrease in apoptosis of β-cell in IGFBP3 treated β-cell;
- k—decrease in insulitis score in an animal model of diabetes;
- l—decrease in diabetes onset in an animal model of diabetes;
- m—protects beta cell injury in an animal model of diabetes;
- n—prevents beta cell loss in an animal model of diabetes.

Preferably the increase in a), b) and c) is by at least 20%; the increase in d) and e) is by at least 30%, preferably by at least 50%; the decrease in f) and the increase in g) is by at least 10%, decrease in k) and l) is by at least 50%, preferably the decrease in l) is by at least 70%. Preferably the decrease j) is by at least 30%.

The invention provides an isolated antibody or antigen binding fragment thereof comprising:
- a. a heavy chain variable domain (VH) comprising:
  - i. a CDR1 sequence of the amino acid sequence selected from the group consisting of: SEQ ID NO: 1, 4, 8, 10, 56, 59, 62, 65 and 68;
  - ii. a CDR2 sequence of the amino acid sequence selected from the group consisting of: SEQ ID NO:2, 5, 11, 57, 60, 63, 66 and 69; and
  - iii. a CDR3 sequence of the amino acid sequence selected from the group consisting of: SEQ ID NO:3, 6, 7, 9, 12, 13, 58, 61, 64, 67 and 70; and/or
- b. a light chain variable domain (VL) comprising:
  - i. a CDR1 sequence of the amino acid sequence selected from the group consisting of: SEQ ID NO:14, 17, 20, 23, 26, 29, 71, 77, 80, 82 and 85;
  - ii. a CDR2 sequence of the amino acid sequence selected from the group consisting of: SEQ ID NO:15, 18, 21, 24, 27, 30, 72, 78, 83 and 86; and
  - iii. a CDR3 sequence of the amino acid sequence selected from the group consisting of: SEQ ID NO:16, 19, 22, 25, 28, 31, 73, 74, 75, 76, 79, 81, 84, 87, 166 and 167.

Preferably the isolated antibody or antigen binding fragment thereof comprises:
- SEQ ID NO: 4 and SEQ ID NO: 5 and SEQ ID NO: 6 and SEQ ID NO: 17 and SEQ ID NO: 18 and SEQ ID NO: 19 or Kabat, IMGT, Chothia, AbM, or Contact CDRs of TC01 or of TC05 or
- SEQ ID NO: 4 and SEQ ID NO: 5 and SEQ ID NO: 6 and SEQ ID NO: 17 and SEQ ID NO: 18 and SEQ ID NO: 166 or Kabat, IMGT, Chothia, AbM, or Contact CDRs of TC03 or
- SEQ ID NO: 4 and SEQ ID NO: 5 and SEQ ID NO: 6 and SEQ ID NO: 17 and SEQ ID NO: 18 and SEQ ID NO: 167 or Kabat, IMGT, Chothia, AbM, or Contact CDRs of TC04 or
- SEQ ID NO: 68 and SEQ ID NO: 69 and SEQ ID NO: 70 and SEQ ID NO: 85 and SEQ ID NO: 86 and SEQ ID NO: 87 or Kabat, IMGT, Chothia, AbM, or Contact CDRs of TM1.

Preferably the isolated antibody or antigen binding fragment thereof comprises:
a. a heavy chain variable domain (VH) comprising:
  i. a CDR1 sequence of the amino acid sequence selected from the group consisting of a sequence as defined using abysis tool analysis (www.abysis.org);
  ii. a CDR2 sequence of the amino acid sequence selected from the group consisting of a sequence as defined using abysis tool analysis (www.abysis.org); and
  iii. a CDR3 sequence of the amino acid sequence selected from the group consisting of a sequence as defined using abysis tool analysis (www.abysis.org); and/or
b. a light chain variable domain (VL) comprising:
  i. a CDR1 sequence of the amino acid sequence selected from the group consisting of a sequence as defined using abysis tool analysis (www.abysis.org);
  ii. a CDR2 sequence of the amino acid sequence selected from the group consisting of a sequence as defined using abysis tool analysis (www.abysis.org); and
  iii. a CDR3 sequence of the amino acid sequence selected from the group consisting of a sequence as defined using abysis tool analysis (www.abysis.org).

Preferably the isolated antibody or antigen binding fragment thereof comprises the CDRs as indicated in Table 2-5, 8-11, as well as Tables 3.1 to 3.4.

Preferably said antibody or antigen binding fragment thereof binds specifically to TMEM219.

Preferably it has at least one activity selected from:
a—increase in IGFBP3 treated healthy subject minigut growth
b—increase in IBD-patient minigut growth;
c—increase in diabetic enteropathy serum treated healthy subject minigut growth;
d—increase in expression of EphB2 and/or LGR5 in IGFBP3 treated healthy subject minigut;
e—decrease in caspase 8 expression in IGFBP3 treated healthy subject minigut;
f—decrease in β-cell loss in IGFBP3 treated β-cell;
g—increase in expression of insulin in IGFBP3 treated β-cell;
h—inhibits or decreases DSS-induced intestinal cells apoptosis;
i—restores expression of PCNA in DSS-treated colon;
j—decrease in apoptosis of β-cell in IGFBP3 treated β-cell.

Preferably the increase in a), b) and c) is by at least 20%; the increase in d) and e) is by at least 50%; the decrease in f) and the increase in g) is by at least 10%.

Preferably the isolated antibody or antigen binding fragment thereof comprises:
a. a heavy chain variable domain (VH) comprising:
  i. a CDR1 sequence of the amino acid sequence selected from the group consisting of: SEQ ID NO: 4, 1, 8, 10, 56, 59, 62, 65 and 68;
  ii. a CDR2 sequence of the amino acid sequence selected from the group consisting of: SEQ ID NO: 5, 2, 11, 57, 60, 63, 66 and 69; and
  iii. a CDR3 sequence of the amino acid sequence selected from the group consisting of: SEQ ID NO:6, 3, 7, 9, 12, 13, 58, 61, 64, 67 and 70; and/or
b. a light chain variable domain (VL) comprising:
  i. a CDR1 sequence of the amino acid sequence selected from the group consisting of: SEQ ID NO:17, 14, 20, 23, 26, 29, 71, 77, 80, 82 and 85;
  ii. a CDR2 sequence of the amino acid sequence selected from the group consisting of: SEQ ID NO:18, 15, 21, 24, 27, 30, 72, 78, 83 and 86; and
  iii. a CDR3 sequence of the amino acid sequence selected from the group consisting of: SEQ ID NO:19, 16, 22, 25, 28, 31, 73, 74, 75, 76, 79, 81, 84, 87, 166 and 167.

Preferably the isolated antibody or antigen binding fragment thereof comprises:
- SEQ ID NO: 4 and SEQ ID NO: 5 and SEQ ID NO: 6 and SEQ ID NO: 17 and SEQ ID NO: 18 and SEQ ID NO: 19 or Kabat, IMGT, Chothia, AbM, or Contact CDRs of TC01 or of TC05 or
- SEQ ID NO: 4 and SEQ ID NO: 5 and SEQ ID NO: 6 and SEQ ID NO: 17 and SEQ ID NO: 18 and SEQ ID NO: 166 or Kabat, IMGT, Chothia, AbM, or Contact CDRs of TC03 or
- SEQ ID NO: 4 and SEQ ID NO: 5 and SEQ ID NO: 6 and SEQ ID NO: 17 and SEQ ID NO: 18 and SEQ ID NO: 167 or Kabat, IMGT, Chothia, AbM, or Contact CDRs of TC04 or
- SEQ ID NO: 68 and SEQ ID NO: 69 and SEQ ID NO: 70 and SEQ ID NO: 85 and SEQ ID NO: 86 and SEQ ID NO: 87 or Kabat, IMGT, Chothia, AbM, or Contact CDRs of TM1.

Preferably the isolated antibody or antigen binding fragment thereof comprises:
a. a heavy chain variable domain (VH) comprising:
  i. a CDR1 sequence of the amino acid sequence selected from the group consisting of a sequence as defined using abysis tool analysis (www.abysis.org);
  ii. a CDR2 sequence of the amino acid sequence selected from the group consisting of a sequence as defined using abysis tool analysis (www.abysis.org); and
  iii. a CDR3 sequence of the amino acid sequence selected from the group consisting of a sequence as defined using abysis tool analysis (www.abysis.org); and/or
b. a light chain variable domain (VL) comprising:
  i. a CDR1 sequence of the amino acid sequence selected from the group consisting of a sequence as defined using abysis tool analysis (www.abysis.org);
  ii. a CDR2 sequence of the amino acid sequence selected from the group consisting of a sequence as defined using abysis tool analysis (www.abysis.org); and iii. a CDR3 sequence of the amino acid sequence selected from the group consisting of a sequence as defined using abysis tool analysis (www.abysis.org).

Preferably the isolated antibody or antigen binding fragment thereof comprises:

a. a heavy chain variable domain sequence of the amino acid sequence selected from the group consisting of: SEQ ID NO:32 to SEQ ID NO:37 or of SEQ ID NO:88 to SEQ ID NO:95; or of SEQ ID NO:168, SEQ ID NO:169 and SEQ ID NO:170; or b. a light chain variable domain sequence of the amino acid sequence selected from the group consisting of: SEQ ID NO: 38 to SEQ ID NO:43; or of SEQ ID NO: 96 to SEQ ID NO: 103 or of SEQ ID NO: 171, SEQ ID NO: 172 or SEQ ID NO: 173;

c. the light chain variable domain of (a) and the heavy chain variable domain of (b).

Still preferably the isolated antibody is TC01, TC03, TC04, TC05, TA02, TC02, TD01, TE01, TG02, TM1, TE02.1, TE02.2, TE02.3, TE03, TE04, TE07, TE10 or antigen binding fragment thereof, preferably the isolated antibody is TC01, TC05, TC03, TC04 or TM1 or antigen binding fragment thereof, as reported in Tables 4, 7 and 10-13 as well as Tables 3.1 to 3.4. Preferably the isolated antibody is TC01.

Still preferably the isolated antibody is TC01 comprising SEQ ID NO:33 and SEQ ID NO:39, TC03 comprising SEQ ID NO:168 and SEQ ID NO:171, TC04 comprising SEQ ID NO:169 and SEQ ID NO:172, TC05 comprising SEQ ID NO:170 and SEQ ID NO:173, TA02 comprising SEQ ID NO:32 and SEQ ID NO:38, TC01 comprising SEQ ID NO:33 and SEQ ID NO:39, TC02 comprising SEQ ID NO:34 and SEQ ID NO:40, TD01 comprising SEQ ID NO:35 and SEQ ID NO:41, TE01 comprising SEQ ID NO:36 and SEQ ID NO:42, TG02 comprising SEQ ID NO:37 and SEQ ID NO:43, TE02.1 comprising SEQ ID NO:88 and SEQ ID NO:96, TE02.2 comprising SEQ ID NO:89 and SEQ ID NO:97, TE02.3 comprising SEQ ID NO:90 and SEQ ID NO:98, TE03 comprising SEQ ID NO:91 and SEQ ID NO:99, TE04 comprising SEQ ID NO:92 and SEQ ID NO:100, TE07 comprising SEQ ID NO:93 and SEQ ID NO:101, TE10 comprising SEQ ID NO:94 and SEQ ID NO:102, TM1 comprising SEQ ID NO:95 and SEQ ID NO:103.

Preferably the isolated antibody or antigen binding fragment of the invention binds to human TMEM219 with an affinity constant lower than or equal to $10^{-7}$ M, preferably with an affinity constant lower than or equal to $2\times10^{-8}$ M.

The invention also provides an isolated antibody or antigen binding fragment thereof that:

(a) binds specifically to an epitope on IGFBP3, e.g., the same or similar epitope as the epitope recognized by the monoclonal antibody TC01, TC03, TC04, TC05, TA02, TC02, TD01, TE01, TG02, TM1, TE02.1, TE02.2, TE02.3, TE03, TE04, TE07, TE10 as defined in Tables 2-19 as well as Tables 3.1 to 3.4; or (b) cross-competes for binding with the monoclonal antibody TC01, TC03, TC04, TC05, TA02, TC02, TD01, TE01, TG02, TM1, TE02.1, TE02.2, TE02.3, TE03, TE04, TE07, TE10 as defined in Tables 2-19 and Tables 3.1-3.4; or (c) shows the same or similar binding affinity or specificity, or both, as any of TC01, TC03, TC04, TC05, TA02, TC02, TD01, TE01, TG02, TM1, TE02.1, TE02.2, TE02.3, TE03, TE04, TE07, TE10 as defined in Tables 2-19 and Tables 3.1-3.4; or (d) has one or more biological properties of an antibody molecule described herein, e.g., an antibody molecule chosen from, e.g., any of TC01, TC03, TC04, TC05, TA02, TC02, TD01, TE01, TG02, TM1, TE02.1, TE02.2, TE02.3, TE03, TE04, TE07, TE10 as defined in Tables 2-19 and Tables 3.1-3.4; or (e) has one or more pharmacokinetic properties of an antibody molecule described herein, e.g., an antibody molecule chosen from, e.g., any of TC01, TC03, TC04, TC05, TA02, TC02, TD01, TE01, TG02, TM1, TE02.1, TE02.2, TE02.3, TE03, TE04, TE07, TE10 as defined in Tables 2-19 and Tables 3.1-3.4.

Preferably the isolated antibody or antigen binding fragment thereof of the invention is a human or humanized antibody.

More preferably the isolated antibody or antigen binding fragment thereof of the invention is an IgG2 or IgG4 antibody, preferably an IgG2 kappa antibody, an IgG2 lambda antibody, an IgG4 kappa antibody or an IgG4 lambda antibody, preferably said IgG2 or IgG4 is human IgG2 or human IgG4.

The invention provides an isolated polynucleotide comprising at least one sequence that encodes the antibody or antigen binding fragment thereof as defined above, preferably said polynucleotide is a cDNA.

The invention provides a vector comprising the polynucleotide as defined above, preferably said vector is selected from the group consisting of a plasmid, a viral vector, a non-episomal mammalian vector, an expression vector, and a recombinant expression vector.

The invention further provides an isolated cell comprising the polynucleotide as defined above or the vector as defined above, preferably the isolated cell is a hybridoma or a Chinese Hamster Ovary (CHO) cell or a Human Embryonic Kidney cells (HEK293).

The invention further provides the antibody or antigen binding fragment thereof or the isolated polynucleotide or the vector or the isolated cell s defined above for use as a medicament, preferably for use in the treatment of: diabetes, intestinal and/or bowel disorder, malabsorption syndrome, cachexia or diabetic enteropathy, preferably diabetes is Type I or Type II diabetes preferably the intestinal and/or bowel disorder is inflammatory bowel disease, celiac disease, ulcerative colitis, Crohn's disease or intestinal obstruction.

The invention provides also a pharmaceutical composition comprising the isolated antibody or antigen binding fragment thereof or the isolated polynucleotide or the vector or the isolated cell as defined above and pharmaceutically acceptable carrier, preferably for use in the treatment of: diabetes, intestinal and/or bowel disorder, malabsorption syndrome, cachexia or diabetic enteropathy, preferably the intestinal and/or bowel disorder is inflammatory bowel disease, celiac disease, ulcerative colitis, Crohn's disease or intestinal obstruction.

The invention provides a method of inhibiting the binding of IGFBP3 to TMEM219 receptor, comprising contacting TMEM219 with the antibody or composition as defined above.

The invention provides a method of treatment of: diabetes, preferably Type 1 or Type 2 diabetes, intestinal and/or bowel disorder, malabsorption syndrome, cachexia or diabetic enteropathy, preferably the intestinal and/or bowel disorder is inflammatory bowel disease, IBD, celiac disease, Crohn's disease or intestinal obstruction, the method comprising administering to a subject in need thereof a pharmaceutical composition comprising the isolated antibody or antigen binding fragment thereof or the isolated polynucleotide or the vector or the isolated cell as defined above and pharmaceutically acceptable carrier or administering to a subject in need thereof the isolated antibody or antigen binding fragment thereof or the isolated polynucleotide or the vector or the isolated cell as defined above.

The present invention also provides a method for producing an antibody or antigen binding fragment thereof, comprising obtaining the cell as defined above and producing the antibody or antigen binding fragment thereof.

In some embodiments, the combination includes an inhibitor of IGFBP3 (e.g., an anti-TMEM antibody molecule as described herein). Thus, compositions and methods for detecting IGFBP3, as well as methods for treating various disorders including diabetes, as well as intestinal and/or bowel disorders, using the anti-TMEM antibody molecules and combinations thereof are disclosed herein.

Accordingly, in one aspect, the invention features an antibody molecule (e.g., an isolated or recombinant antibody molecule) having one or more of the following properties:

- binds to TMEM219, e.g., human TMEM219, with high affinity, e.g., with an affinity constant of at least about $4\times10^6$ $M^{-1}$, preferably $10^7$ $M^{-1}$, typically about $10^8$ $M^{-1}$ and more typically, about $10^9$ $M^{-1}$ to $10^{10}$ $M^{-1}$ or stronger;
- inhibits or reduces binding of IGFBP3 to its receptor, TMEM;
- binds specifically to an epitope on TMEM219, e.g., the same or similar epitope as the epitope recognized by the monoclonal antibody TC01, TC03, TC04, TC04, TA02, TC02, TD01, TE01, TG02, TM1, TE02.1, TE02.2, TE02.3, TE03, TE04, TE07, TE10 as defined in Tables 2-19 and Tables 3.1-3.4;
- cross-competes for binding with the monoclonal antibody TC01, TC03, TC04, TC04, TA02, TC02, TD01, TE01, TG02, TM1, TE02.1, TE02.2, TE02.3, TE03, TE04, TE07, TE10 as defined in Tables 2-19 and Tables 3.1-3.4;
- shows the same or similar binding affinity or specificity, or both, as any of TC01, TC03, TC04, TC04, TA02, TC02, TD01, TE01, TG02, TM1, TE02.1, TE02.2, TE02.3, TE03, TE04, TE07, TE10 as defined in Tables 2-19 and Tables 3.1-3.4;
- shows the same or similar binding affinity or specificity, or both, as an antibody molecule (e.g., an heavy chain variable region and light chain variable region) described in Tables 2-19;
- shows the same or similar binding affinity or specificity, or both, as an antibody molecule (e.g., an heavy chain variable region and light chain variable region) having an amino acid sequence shown in Tables 4, 5, 10, 11, 16, 17;
- shows the same or similar binding affinity or specificity, or both, as an antibody molecule (e.g., an heavy chain variable region and light chain variable region) encoded by the nucleotide sequence shown in Tables 6-7 and 12, 13, 16, 17;
- binds the same or an overlapping epitope with a second antibody molecule to TMEM219 wherein the second antibody molecule is an antibody molecule described herein, e.g., an antibody molecule chosen from TC01, TC03, TC04, TC04, TA02, TC02, TD01, TE01, TG02, TM1, TE02.1, TE02.2, TE02.3, TE03, TE04, TE07, TE10 as defined in Tables 2-19 and Tables 3.1-3.4;
- has one or more biological properties of an antibody molecule described herein, e.g., an antibody molecule chosen from, e.g., any of TC01, TC03, TC04, TC04, TA02, TC02, TD01, TE01, TG02, TM1, TE02.1, TE02.2, TE02.3, TE03, TE04, TE07, TE10 as defined in Tables 2-19 and Tables 3.1-3.4;
- has one or more pharmacokinetic properties of an antibody molecule described herein, e.g., an antibody molecule chosen from, e.g., any of TC01, TC03, TC04, TC04, TA02, TC02, TD01, TE01, TG02, TM1, TE02.1, TE02.2, TE02.3, TE03, TE04, TE07, TE10 as defined in Tables 2-19 and Tables 3.1-3.4;
- inhibits one or more activities of IGFBP3, e.g., results in one or more of: an increase of at least 20% in the development of minigut from IBD-patient derived tissue sample when compared to untreated samples and/or an increase of at least 20% in the development of minigut growth in presence of IGFBP3 when compared to untreated samples or an increase of at least 20% in the development of minigut growth in presence of diabetic enteropathy serum when compared to untreated samples;
- induces an increase in EphB2 and LGR5 of at least 50% compared to the IGFBP3-treated samples; or decrease in caspase 8 expression level of at least 50% compared to the IGFBP3-treated samples; or
- inhibits one or more activities of IGFBP3, e.g., results in one or more of: a reduction in beta cell loss, or an increase in Insulin; The reduction in beta cell loss or the increase in insulin is at least 10% compared to IGFBP3 treated samples;
- inhibits, reduces or neutralizes one or more activities of IGFBP3, resulting in blockade or reduction of IGFBP3 induced apoptosis;
- binds human TMEM219 and is cross-reactive with cynomolgus TMEM219.

Nucleic acid molecules encoding the antibody molecules, expression vectors, host cells and methods for making the antibody molecules are also provided. Immunoconjugates, multi- or bispecific antibody molecules and pharmaceutical compositions comprising the antibody molecules are also provided.

Without being bound to any theory, it is believed that IGFBP3/TMEM219 axis is dysfunctional in inflammatory bowel diseases (IBD) thus leading to ISCs loss and to altered function of the mucosal barrier, which is further invaded by microbes that trigger and sustain immune response activation and inflammation. The use of agents that block the IGFBP3-TMEM219 interaction in IBD may protect ISCs and preserve the integrity of the intestinal barrier, thus preventing the development of local inflammation.

Further, activation of TMEM219 signaling increases apoptosis of beta cells through upregulation of caspase 8 expression and reduced insulin expression. IGFBP3 is increased in the serum of patients with pre-T1D and pre-T2D as well as in newly diagnosed and long-standing diabetes patients and TMEM219 is expressed in beta cells.

An expression or overexpression of TMEM219 favors beta cells destruction and affects beta cell mass, and the consequent hyperglycemia/inflammation perpetuates the process during diabetes onset and progression. Altered glycemic control and inflammation in pre-diabetic conditions favor an increased IGFBP3 hepatic production, which may target TMEM219 expressed on pancreatic beta cells and trigger a loop where TMEM219 overexpression parallels the increase in IGFBP3 release. Then TMEM219 may trigger beta cell death and thus targeting the IGFBP3/TMEM219 axis may prevent such cell death.

The anti-TMEM antibody molecules disclosed herein can be used (alone or in combination with other agents or therapeutic modalities) to treat, prevent and/or diagnose disorders, such as diabetes, as well as intestinal and/or bowel disorders, malabsorption syndrome, inflammatory bowel disease, cachexia, IBD, celiac disease, diabetic enteropathy. Additionally, disclosed herein are methods and compositions comprising a combination of two, three or more therapeutic agents chosen from one, two, or all of the following categories (i)-(iii): (i) an agent that treat diabetes; (ii) an anti-inflammatory agent; or (iii) an immunotherapeutic agent.

The additional therapeutic agent may be selected from an agent that treat diabetes including: insulin, Insulin glargine as detailed in Vandana, 2014 (19, incorporated by reference), biguanide, glucosidase inhibitors, thiazolidinedione, DPP-4 inhibitors, GLP-1 receptor agonists as detailed in George et al 2013 (20, incorporated by reference)), an agent used to prevent diabetes, aspirin, anticoagulation and platelet anti-aggregation agents (such as enoxaparin, eparin, sulodexide); cholesterol-lowering drugs (such as statins, bile acids sequestrants, ezetimibe, fibrates as described in Marsha et al 2011 (21, incorporated by reference)); other blood pressure lowering agents (such as thiazide, ACE inhibitors, beta and alpha blockers); an anti-apoptotic agent, an anti-inflammatory agent, corticosteroids and immune suppressive agent (22, incorporated by reference), adjuvant therapy in organ transplantation, protective agent in cell therapy approach, a pain reliever, antibiotic, probiotics, TNF-alpha blockers (23, incorporated by reference), SGLT2 inhibitors (such as gliflozin derivates), integrin inhibitors (24, incorporated by reference).

Methods to measure an increase in minigut growth when compared to minigut growth in the presence of IGFBP3, and/or in the presence of diabetic enteropathy serum are known in the art and are described in several publications (4, 18, 27, 28).

Methods to measure an increase and/or a decrease in EphB2, LGR5 or caspase 8 expression when compared to expression in the presence of IGFBP3 are known in the art and include quantitative RT-PCR, Realt-Time RT-PCR, microarray, northern blotting, RNA-Seq (29,30) or as described in the method section below.

Methods to measure a decrease in beta-cell loss when compared to beta-cell loss in the presence of IGFBP3 are known in the art and include cell proliferation assays (CFSE staining, Calcein/PI staining, Trypan Blue exclusion, BrdU staining, MTT) apoptosis assays (TUNEL, Caspase activation and detection, Annexin V binding) or as described in the method section below.

Methods to measure an increase in insulin level when compared to insulin level in the presence of IGFBP3 are known in the art and include western blots, ELISA mass spectrometry (31-33).

Methods to measure a decrease in apoptosis when compared to apoptosis in the presence of IGFBP3 are known in the art and include DNA fragmentation, Caspase activation analysis, Mithocondrial membrane permeabilization, Annexin V binding (34) or as described in the method section below.

In some embodiments, the antibody molecule binds to IGFBP3 with high affinity, e.g., with a KD that is about the same, or at least about 10%, 20%, 30%, 40%, 50%, 60%, 70%, 80% or 90% higher or lower than the KD of a murine anti-TMEM antibody molecule or chimeric anti-TMEM antibody molecule or a commercial anti-TMEM antibody molecule. In some embodiments, the KD of the murine or chimeric anti-TMEM antibody molecule is less than about 0.4, 0.3, 0.2, 0.1, or 0.05 nM, e.g., measured by a Biacore method or KinExA=kinetic exclusion assays. In some embodiments, the KD of the murine or chimeric anti-TMEM219 antibody molecule is less than about 0.2 nM. In other embodiments, the KD of the murine or chimeric anti IGFBP3 antibody molecule is less than about 10, 5, 3, 2, or 1 nM, e.g., measured by binding on cells expressing IGFBP3 (e.g., 300.19 cells). In some embodiments, the KD of the murine or chimeric anti IGFBP3 antibody molecule is less than about 1 nM.

Methods to measure binding to TMEM219 are known in the art as protein-protein interactions assays and include ELISA, co-immunoprecipitation, surface plasmon resonance, FRET—Forster resonance energy transfer (35) or as described in the method section below.

In some embodiments, the expression level of the antibody molecule is higher, e.g., at least about 0.5, 1, 2, 3, 4, 5, 6, 7, 8, 9 or 10-fold higher, than the expression level of a murine or chimeric antibody molecule, e.g., a murine, commercial or chimeric anti-TMEM antibody molecule. In some embodiments, the antibody molecule is expressed in HEK293 cells, CHO cells or any suitable mammalian cell line known in the art.

In some embodiments, the anti-TMEM219 antibody molecule reduces one or more TMEM-associated activities with an IC50 (concentration at 50% inhibition) that is about the same or lower, e.g., at least about 10%, 20%, 30%, 40%, 50%, 60%, 70%, 80% or 90% lower, than the IC50 of a murine, commercial or chimeric anti-TMEM antibody molecule, e.g., a murine commercial or chimeric anti-TMEM antibody molecule described herein.

In some embodiments, the anti-TMEM antibody molecule has improved stability, e.g., at least about 0.5, 1, 2, 3, 4, 5, 6, 7, 8, 9 or 10-fold more stable in vivo or in vitro, than a murine, commercial or chimeric anti-TMEM antibody molecule, such as HPA051870, as defined in material section below.

In one embodiment, the anti TMEM antibody molecule is a humanized antibody molecule.

In another embodiment, the anti-TMEM antibody molecule comprises at least one antigen-binding region, e.g., a variable region or an antigen-binding fragment thereof, from an antibody described herein, e.g., an antibody chosen from any of TA02, TC01, TC02, TD01, TE01, TG02, TM1, TE02.1, TE02.2, TE02.3, TE03, TE04, TE07, TE10 as defined in Tables 2-5, 8-11 or encoded by the nucleotide sequence in Tables 6, 7, 12, 13; or a sequence substantially identical (e.g., at least 80%, 85%, 90%, 92%, 95%, 97%, 98%, 99% or higher identical) to any of the aforesaid sequences.

In yet another embodiment, the anti-TMEM antibody molecule comprises at least one, two, three or four variable regions from an antibody described herein, e.g., an antibody chosen from any of TA02, TC01, TC02, TD01, TE01, TG02, TM1, TE02.1, TE02.2, TE02.3, TE03, TE04, TE07, TE10 as defined in Tables 2-5, 8-11 or encoded by the nucleotide sequence in Tables 6, 7, 12, 13; or a sequence substantially identical (e.g., at least 80%, 85%, 90%, 92%, 95%, 97%, 98%, 99% or higher identical) to any of the aforesaid sequences.

In yet another embodiment, the anti-TMEM antibody molecule comprises at least one or two heavy chain variable regions from an antibody described herein, e.g., an antibody chosen from any of TA02, TC01, TC02, TD01, TE01, TG02, TM1, TE02.1, TE02.2, TE02.3, TE03, TE04, TE07, TE10 as defined in Tables 2-5, 8-11 or encoded by the nucleotide sequence in Tables 6, 7, 12, 13; or a sequence substantially identical (e.g., at least 80%, 85%, 90%, 92%, 95%, 97%, 98%, 99% or higher identical) to any of the aforesaid sequences.

In yet another embodiment, the anti-TMEM antibody molecule comprises at least one or two light chain variable regions from an antibody described herein, e.g., an antibody chosen from any of TA02, TC01, TC02, TD01, TE01, TG02, TM1, TE02.1, TE02.2, TE02.3, TE03, TE04, TE07, TE10 as defined in Tables 2-5, 8-11 or encoded by the nucleotide sequence in Tables 6, 7, 12, 13; or a sequence substantially identical (e.g., at least 80%, 85%, 90%, 92%, 95%, 97%, 98%, 99% or higher identical) to any of the aforesaid sequences.

In yet another embodiment, the anti-TMEM antibody molecule includes a heavy chain constant region for an IgG4, e.g., a human IgG4. In one embodiment, the human IgG4 includes a substitution at position 228 (e.g., a Ser to Pro substitution). In one embodiment, the human IgG4 includes a substitution at position 235 (e.g., a Leu to Glu substitution). In one embodiment, the human IgG4 includes a substitution at position 228 (e.g., a Ser to Pro substitution) and a substitution at position 235 (e.g., a Leu to Glu substitution). In still another embodiment, the anti-TMEM antibody molecule includes a heavy chain constant region for an IgG1, e.g., a human IgG1. In one embodiment, the human IgG1 includes a substitution at position 297 (e.g., an Asn to Ala substitution). In one embodiment the human IgG1 includes a substitution at position 250, a substitution at position 428, or both (e.g., a Thr to Gln substitution at position 250 and/or a Met to Leu substitution at position 428). In one embodiment, the human IgG1 includes a substitution at position 234, a substitution at position 235, or both (e.g., a Leu to Ala substitution at position 234 and/or a Leu to Ala substitution at position 235).

In yet another embodiment, the anti-TMEM antibody molecule includes a kappa light chain constant region, e.g., a human kappa light chain constant region. In one embodiment, the light chain constant region comprises an amino sequence set forth in Table 8, or a sequence substantially identical (e.g., at least 80%, 85%, 90%, 92%, 95%, 97%, 98%, 99% or higher identical) thereto.

In another embodiment, the anti-TMEM antibody molecule includes a heavy chain constant region for an IgG4, e.g., a human IgG4, and a kappa light chain constant region, e.g., a human kappa light chain constant region. In one embodiment, the human IgG1 or IgG4 includes a substitution at the variable region to decrease aggregation, reduce charge heterogeneity, increase affinity and modulate antigen binding; removal by mutation of instability hotspot in the CDR, putative N-glycosylation sites in the variable region as described in (26), incorporated by reference.

In another embodiment, the anti-TMEM antibody molecule includes a heavy chain variable domain and a constant region, a light chain variable domain and a constant region, or both, comprising the amino acid sequence of any of TA02, TC01, TC02, TD01, TE01, TG02, TM1, TE02.1, TE02.2, TE02.3, TE03, TE04, TE07, TE10 as defined in Tables 2-5, 8-11 or encoded by the nucleotide sequence in Tables 6, 7, 12, 13; or a sequence substantially identical (e.g., at least 80%, 85%, 90%, 92%, 95%, 97%, 98%, 99% or higher identical) to any of the aforesaid sequences. The anti-TMEM antibody molecule, optionally, comprises a leader sequence from a heavy chain, a light chain, or both.

In yet another embodiment, the anti-TMEM antibody molecule includes at least one, two, or three complementarity determining regions (CDRs) from a heavy chain variable region of an antibody described herein, e.g., an antibody chosen from any of any of TA02, TC01, TC02, TD01, TE01, TG02, TM1, TE02.1, TE02.2, TE02.3, TE03, TE04, TE07, TE10 as defined in Tables 2-5, 8-11 or encoded by the nucleotide sequence in Tables 6, 7, 12, 13; or a sequence substantially identical (e.g., at least 80%, 85%, 90%, 92%, 95%, 97%, 98%, 99% or higher identical) to any of the aforesaid sequences.

In yet another embodiment, the anti-TMEM antibody molecule includes at least one, two, or three CDRs (or collectively all of the CDRs) from a heavy chain variable region comprising an amino acid sequence shown in Tables 2-5, 8-11 or encoded by a nucleotide sequence shown in Tables 6-7, 12, 13. In one embodiment, one or more of the CDRs (or collectively all of the CDRs) have one, two, three, four, five, six or more changes, e.g., amino acid substitutions or deletions, relative to the amino acid sequence shown in Tables 2-5, 8-11 or encoded by a nucleotide sequence shown in Tables 6-7, 12, 13.

In yet another embodiment, the anti-TMEM antibody molecule includes at least one, two, or three CDRs from a light chain variable region of an antibody described herein, e.g., an antibody chosen from any of any of TA02, TC01, TC02, TD01, TE01, TG02, TM1, TE02.1, TE02.2, TE02.3, TE03, TE04, TE07, TE10 as defined in Tables 2-5, 8-11 or encoded by the nucleotide sequence in Tables 6, 7, 12, 13; or a sequence substantially identical (e.g., at least 80%, 85%, 90%, 92%, 95%, 97%, 98%, 99% or higher identical) to any of the aforesaid sequence.

In yet another embodiment, the anti-TMEM antibody molecule includes at least one, two, or three CDRs (or collectively all of the CDRs) from a light chain variable region comprising an amino acid sequence shown in Tables 2-5, 8-11 or encoded by a nucleotide sequence shown in Tables 6, 7, 12, 13. In one embodiment, one or more of the CDRs (or collectively all of the CDRs) have one, two, three, four, five, six or more changes, e.g., amino acid substitutions or deletions, relative to the amino acid sequence shown in Tables 2-5, 8-11, or encoded by a nucleotide sequence shown in Tables 6, 7, 12, 13. In certain embodiments, the anti-TMEM antibody molecule includes a substitution in a light chain CDR, e.g., one or more substitutions in a CDR1, CDR2 and/or CDR3 of the light chain.

In another embodiment, the anti-TMEM antibody molecule includes at least one, two, three, four, five or six CDRs (or collectively all of the CDRs) from a heavy and light chain variable region comprising an amino acid sequence shown in Tables 2-5, 8-11, or encoded by a nucleotide sequence shown in Tables 6, 7, 12, 13. In one embodiment, one or more of the CDRs (or collectively all of the CDRs) have one, two, three, four, five, six or more changes, e.g., amino acid substitutions or deletions, relative to the amino acid sequence shown in Tables 2-5, 8-11, or encoded by a nucleotide sequence shown in Tables 6, 7, 12, 13.

In one embodiment, the anti-TMEM antibody molecule includes all six CDRs from an antibody described herein, e.g., an antibody chosen from any of any of TA02, TC01, TC02, TD01, TE01, TG02, TM1, TE02.1, TE02.2, TE02.3, TE03, TE04, TE07, TE10 as defined in Tables 2-5, 8-11 or encoded by the nucleotide sequence in Tables 6, 7, 12, 13, or closely related CDRs, e.g., CDRs which are identical or which have at least one amino acid alteration, but not more than two, three or four alterations (e.g., substitutions, deletions, or insertions, e.g., conservative substitutions). In one embodiment, the anti-TMEM antibody molecule may include any CDR described herein. In certain embodiments, the anti-TMEM antibody molecule includes a substitution in a light chain CDR, e.g., one or more substitutions in a CDR1, CDR2 and/or CDR3 of the light chain. In another embodiment, the anti-TMEM antibody molecule includes at least one, two, or three CDRs according to Kabat et al. (e.g., at least one, two, or three CDRs according to the Kabat definition as set out in Tables 2-5) from a heavy chain variable region of an antibody described herein, e.g., an antibody chosen from any of any of TA02, TC01, TC02, TD01, TE01, TG02, TM1, TE02.1, TE02.2, TE02.3, TE03, TE04, TE07, TE10 as defined in Tables 2-5, 8-11 or encoded by the nucleotide sequence in Tables 6, 7, 12, 13; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat et al. shown in Tables 2-5, 8-11.

In another embodiment, the anti-TMEM antibody molecule includes at least one, two, or three CDRs according to Kabat et al. (e.g., at least one, two, or three CDRs according to the Kabat definition as set out in Tables 2-5, 8-11) from a light chain variable region of an antibody described herein, e.g., an antibody chosen from any of any of TA02, TC01, TC02, TD01, TE01, TG02, TM1, TE02.1, TE02.2, TE02.3, TE03, TE04, TE07, TE10 as defined in Tables 2-5, 8-11 or encoded by the nucleotide sequence in Tables 6, 7, 12, 13; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat et al. shown in Tables 2-5, 8-11.

In yet another embodiment, the anti-TMEM antibody molecule includes at least one, two, three, four, five, or six CDRs according to Kabat et al. (e.g., at least one, two, three, four, five, or six CDRs according to the Kabat definition as set out in Tables 2-5, 8-11) from the heavy and light chain variable regions of an antibody described herein, e.g., an antibody chosen from any of TA02, TC01, TC02, TD01, TE01, TG02, TM1, TE02.1, TE02.2, TE02.3, TE03, TE04, TE07, TE10 as defined in Tables 2-5, 8-11 or encoded by the nucleotide sequence in Tables 6, 7, 12, 13; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, three, four, five, or six CDRs according to Kabat et al. shown in Tables 2-5, 8-11.

In yet another embodiment, the anti-TMEM antibody molecule includes all six CDRs according to Kabat et al. (e.g., all six CDRs according to the Kabat definition as set out in Tables 2-5, 8-11) from the heavy and light chain variable regions of an antibody described herein, e.g., an antibody chosen from any of TA02, TC01, TC02, TD01, TE01, TG02, TM1, TE02.1, TE02.2, TE02.3, TE03, TE04, TE07, TE10 as defined in Tables 2-5, 8-11 or encoded by the nucleotide sequence in Tables 6, 7, 12, 13; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to all six CDRs according to Kabat et al. shown in Tables 2-5, 8-11. In one embodiment, the anti-TMEM antibody molecule may include any CDR described herein.

In another embodiment, the anti-TMEM antibody molecule includes at least one, two, or three Chothia or Kabat hypervariable loops (e.g., at least one, two, or three hypervariable loops according to the Chothia or Kabat definition as set out in Tables 2-5, 8-11) from a heavy chain variable region of an antibody described herein, e.g., an antibody chosen from any of any of TA02, TC01, TC02, TD01, TE01, TG02, TM1, TE02.1, TE02.2, TE02.3, TE03, TE04, TE07, TE10 as defined in Tables 2-5, 8-11 or encoded by the nucleotide sequence in Tables 6, 7, 12, 13; or at least the amino acids from those hypervariable loops that contact TMEM; or which have at least one amino acid alteration, but not more than two, three or four alterations (e.g., substitutions, deletions, or insertions, e.g., conservative substitutions) relative to one, two, or three hypervariable loops according to Chothia et al. shown in Tables 2-5, 8-11.

In another embodiment, the anti-TMEM antibody molecule includes at least one, two, or three Chothia hypervariable loops (e.g., at least one, two, or three hypervariable loops according to the Chothia definition as set out in Tables 2-5, 8-11) of a light chain variable region of an antibody described herein, e.g., an antibody chosen from any of any of TA02, TC01, TC02, TD01, TE01, TG02, TM1, TE02.1, TE02.2, TE02.3, TE03, TE04, TE07, TE10 as defined in Tables 2-5, 8-11 or encoded by the nucleotide sequence in Tables 6, 7, 12, 13; or at least the amino acids from those hypervariable loops that contact TMEM; or which have at least one amino acid alteration, but not more than two, three or four alterations (e.g., substitutions, deletions, or insertions, e.g., conservative substitutions) relative to one, two, or three hypervariable loops according to Chothia et al. shown in Tables 2-5, 8-11.

In yet another embodiment, the anti-TMEM antibody molecule includes at least one, two, three, four, five, or six hypervariable loops (e.g., at least one, two, three, four, five, or six hypervariable loops according to the Chothia definition as set out in Tables 2-5, 8-11) from the heavy and light chain variable regions of an antibody described herein, e.g., an antibody chosen from any of any of TA02, TC01, TC02, TD01, TE01, TG02, TM1, TE02.1, TE02.2, TE02.3, TE03, TE04, TE07, TE10 as defined in Tables 2-5, 8-11 or encoded by the nucleotide sequence in Tables 6, 7, 12, 13; or at least the amino acids from those hypervariable loops that contact TMEM; or which have at least one amino acid alteration, but not more than two, three or four alterations (e.g., substitutions, deletions, or insertions, e.g., conservative substitutions) relative to one, two, three, four, five or six hypervariable loops according to Chothia et al. shown in Tables 2-5, 8-11.

In one embodiment, the anti-TMEM antibody molecule includes all six hypervariable loops (e.g., all six hypervariable loops according to the Chothia definition as set out in Tables 2-5, 8-11) of an antibody described herein, e.g., an antibody chosen from any of any of TA02, TC01, TC02, TD01, TE01, TG02, TM1, TE02.1, TE02.2, TE02.3, TE03, TE04, TE07, TE10 as defined in Tables 2-5, 8-11 or encoded by the nucleotide sequence in Tables 6, 7, 12, 13 or closely related hypervariable loops, e.g., hypervariable loops which are identical or which have at least one amino acid alteration, but not more than two, three or four alterations (e.g., substitutions, deletions, or insertions, e.g., conservative substitutions); or which have at least one amino acid alteration, but not more than two, three or four alterations (e.g., substitutions, deletions, or insertions, e.g., conservative substitutions) relative to all six hypervariable loops according to Chothia et al. shown in Tables 2-5, 8-11. In one embodiment, the anti-TMEM antibody molecule may include any hypervariable loop described herein.

In still another embodiment, the anti-TMEM antibody molecule includes at least one, two, or three hypervariable loops that have the same canonical structures as the corresponding hypervariable loop of an antibody described herein, e.g., an antibody chosen from any of any of TA02, TC01, TC02, TD01, TE01, TG02, TM1, TE02.1, TE02.2, TE02.3, TE03, TE04, TE07, TE10 as defined in Tables 2-5, 8-11 or encoded by the nucleotide sequence in Tables 6, 7, 12, 13, e.g., the same canonical structures as at least loop 1 and/or loop 2 of the heavy and/or light chain variable domains of an antibody described herein. See, e.g., Chothia et al., (1992) J. Mol. Biol. 227:799-817; Tomlinson et al., (1992) J. Mol. Biol. 227:776-798 for descriptions of hypervariable loop canonical structures. These structures can be determined by inspection of the tables described in these references.

In certain embodiments, the anti-TMEM antibody molecule includes a combination of CDRs or hypervariable loops defined according to the Kabat et al. and Chothia et al.

In one embodiment, the anti-TMEM antibody molecule includes at least one, two or three CDRs or hypervariable loops from a heavy chain variable region of an antibody described herein, e.g., an antibody chosen from any of any of TA02, TC01, TC02, TD01, TE01, TG02, TM1, TE02.1, TE02.2, TE02.3, TE03, TE04, TE07, TE10 as defined in Tables 2-5, 8-11 or encoded by the nucleotide sequence in Tables 6, 7, 12, 13, according to the Kabat and Chothia definition (e.g., at least one, two, or three CDRs or hypervariable loops according to the Kabat and Chothia definition as set out in Tables 2-5, 8-11); or encoded by the nucleotide sequence in Tables 6, 7, 12, 13; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs or hypervariable loops according to Kabat and/or Chothia shown in Tables 2-5, 8-11.

For example, the anti-TMEM antibody molecule can include VH CDR1 according to Kabat et al. or VH hypervariable loop 1 according to Chothia et al., or a combination thereof, e.g., as shown in Tables 2-5, 8-11. The anti-TMEM antibody molecule can further include, e.g., VH CDRs 2-3 according to Kabat et al. and VL CDRs 1-3 according to Kabat et al., e.g., as shown in Tables 2-5, 8-11. Accordingly, in some embodiments, framework regions are defined based on a combination of CDRs defined according to Kabat et al. and hypervariable loops defined according to Chothia et al. For example, the anti-TMEM antibody molecule can include VH FR1 defined based on VH hypervariable loop 1 according to Chothia et al. and VH FR2 defined based on VH CDRs 1-2 according to Kabat et al., e.g., as shown in Tables 2-5, 8-11, 6, 7, 12, 13. The anti-TMEM antibody molecule can further include, e.g., VH FRs 3-4 defined based on VH CDRs 2-3 according to Kabat et al. and VL FRs 1-4 defined based on VL CDRs 1-3 according to Kabat et al.

The anti-TMEM antibody molecule can contain any combination of CDRs or hypervariable loops according to the Kabat and Chothia definitions. In one embodiment, the anti-TMEM antibody molecule includes at least one, two or three CDRs from a light chain variable region of an antibody described herein, e.g., an antibody chosen from any of any of TA02, TC01, TC02, TD01, TE01, TG02, TM1, TE02.1, TE02.2, TE02.3, TE03, TE04, TE07, TE10 as defined in Tables 2-5, 8-11 or encoded by the nucleotide sequence in Tables 6, 7, 12, 13 according to the Kabat and Chothia definition (e.g., at least one, two, or three CDRs according to the Kabat and Chothia definition as set out in Tables 3.3 e 3.4). Preferred anti-TMEM antibodies are TC01 and TM1 as defined in Tables 2-5, 8-11 or encoded by the nucleotide sequence in Tables 6, 7, 12, 13. In an embodiment, e.g., an embodiment comprising a variable region, a CDR (e.g., Chothia CDR or Kabat CDR), or other sequence referred to herein, e.g., in Tables 2-5, 8-11, the antibody molecule is a monospecific antibody molecule, a bispecific antibody molecule, or is an antibody molecule that comprises an antigen binding fragment of an antibody, e.g., a half antibody or antigen binding fragment of a half antibody. In embodiments the antibody molecule is a bispecific antibody molecule having a first binding specificity for IGFBP3 and a second binding specificity for TNF-alpha, integrin, IL1, IL12 and IL23, CD3, CD20, CD80, CD86.

In one embodiment, the anti-TMEM antibody molecule includes:
(i) a heavy chain variable region (VH) including a VHCDR1 amino acid sequence chosen from any one of SEQ ID NO: 1, 4, 8, 10, 56, 59, 62, 65 and 68; a VHCDR2 amino acid sequence chosen from any one of SEQ ID NO: 2, 5, 11, 57, 60, 63, 66 and 69; and a VHCDR3 amino acid sequence chosen from any one of SEQ ID NO: 3, 6, 7, 9, 12, 13, 58, 61, 64, 67 and 70; and
(ii) a light chain variable region (VL) including a VLCDR1 amino acid sequence chosen from any one of SEQ ID NO: 14, 17, 20, 23, 26, 29, 71, 77, 80, 82 and 85, a VLCDR2 amino acid sequence chosen from any one of SEQ ID NO: 15, 18, 21, 24, 27, 30, 72, 78, 83 and 86, and a VLCDR3 amino acid sequence chosen from SEQ ID NO: 16, 19, 22, 25, 28, 31, 73, 74, 75, 76, 79, 81, 84 and 87.

In one embodiment, the light or the heavy chain variable framework (e.g., the region encompassing at least FR1, FR2, FR3, and optionally FR4) of the anti-TMEM antibody molecule can be chosen from: (a) a light or heavy chain variable framework including at least 80%, 85%, 87% 90%, 92%, 93%, 95%, 97%, 98%, or preferably 100% of the amino acid residues from a human light or heavy chain variable framework, e.g., a light or heavy chain variable framework residue from a human mature antibody, a human germline sequence, or a human consensus sequence; (b) a light or heavy chain variable framework including from 20% to 80%, 40% to 60%, 60% to 90%, or 70% to 95% of the amino acid residues from a human light or heavy chain variable framework, e.g., a light or heavy chain variable framework residue from a human mature antibody, a human germline sequence, or a human consensus sequence; (c) a non-human framework (e.g., a rodent framework); or (d) a non-human framework that has been modified, e.g., to remove antigenic or cytotoxic determinants, e.g., deimmunized, or partially humanized.

In one embodiment, the light or heavy chain variable framework region (particularly FR1, FR2 and/or FR3) includes a light or heavy chain variable framework sequence at least 70, 75, 80, 85, 87, 88, 90, 92, 94, 95, 96, 97, 98, 99% identical or identical to the frameworks of a VL or VH segment of a human germline gene.

In certain embodiments, the anti-TMEM antibody molecule comprises a heavy chain variable domain having at least one, two, three, four, five, six, seven, ten, fifteen, twenty or more changes, e.g., amino acid substitutions or deletions.

In one embodiment, the heavy or light chain variable region, or both, of the anti-TMEM antibody molecule includes an amino acid sequence encoded by a nucleic acid sequence described herein or a nucleic acid that hybridizes to a nucleic acid sequence described herein (e.g., a nucleic acid sequence as shown in Tables 6, 7, 12, 13) or its complement, e.g., under low stringency, medium stringency, or high stringency, or other hybridization condition described herein.

In another embodiment, the anti-TMEM antibody molecule comprises at least one, two, three, or four antigen-binding regions, e.g., variable regions, having an amino acid sequence as set forth in Tables 2-5, 8-11 or a sequence substantially identical thereto (e.g., a sequence at least about 85%, 90%, 95%, 99% or more identical thereto, or which differs by no more than 1, 2, 5, 10, or 15 amino acid residues from the sequences shown in Tables 2-5, 8-11. In another embodiment, the anti-TMEM antibody molecule includes a VH and/or VL domain encoded by a nucleic acid having a nucleotide sequence as set forth in Tables 2-5, 8-11 or a sequence substantially identical thereto (e.g., a sequence at least about 85%, 90%, 95%, 99% or more identical thereto, or which differs by no more than 3, 6, 15, 30, or 45 nucleotides from the sequences shown in Tables 2-5, 8-11.

In yet another embodiment, the anti-TMEM antibody molecule comprises at least one, two, or three CDRs from a heavy chain variable region having an amino acid sequence as set forth in Tables 2-5, 8-11, or a sequence substantially homologous thereto (e.g., a sequence at least about 85%, 90%, 95%, 99% or more identical thereto, and/or having one, two, three or more substitutions, insertions or deletions, e.g., conserved substitutions). In yet another embodiment, the anti-TMEM antibody molecule comprises at least one, two, or three CDRs from a light chain variable region having an amino acid sequence as set forth in Tables 2-5, 8-11 or a sequence substantially homologous thereto (e.g., a sequence at least about 85%, 90%, 95%, 99% or more identical thereto, and/or having one, two, three or more substitutions, insertions or deletions, e.g., conserved substitutions). In yet another embodiment, the anti-TMEM antibody molecule comprises at least one, two, three, four, five or six CDRs from heavy and light chain variable regions having an amino acid sequence as set forth in Tables 2-5, 8-11), or a sequence substantially homologous thereto (e.g., a sequence at least about 85%, 90%, 95%, 99% or more identical thereto, and/or having one, two, three or more substitutions, insertions or deletions, e.g., conserved substitutions).

In yet other embodiments, the anti-TMEM antibody molecule has a heavy chain constant region (Fc) chosen from, e.g., the heavy chain constant regions of IgG1, IgG2, IgG3, IgG4, IgM, IgA1, IgA2, IgD, and IgE; particularly, chosen from, e.g., the heavy chain constant regions of IgG1, IgG2, IgG3, and IgG4, more particularly, the heavy chain constant region of IgG1 or IgG4 (e.g., human IgG1, IgG2 or IgG4). In one embodiment, the heavy chain constant region is human IgG1. In another embodiment, the anti-TMEM antibody molecule has a light chain constant region chosen from, e.g., the light chain constant regions of kappa or lambda. In one embodiment, the constant region is altered, e.g., mutated, to modify the properties of the anti-TMEM antibody molecule (e.g., to increase or decrease one or more of: Fc receptor binding, antibody glycosylation, the number of cysteine residues, effector cell function, complement function, half-life, aggregation and stability). In certain embodiments, the anti-TMEM antibody molecules comprises a human IgG4 mutated In one embodiment, the anti-TMEM antibody molecule is isolated or recombinant.

In one embodiment, the anti-TMEM antibody molecule is a humanized or human antibody molecule.

The invention also features a nucleic acid molecule that comprise one or both nucleotide sequences that encode heavy and light chain variable regions, CDRs, hypervariable loops, framework regions of the anti-TMEM antibody molecules, as described herein. In certain embodiments, the nucleotide sequence that encodes the anti-TMEM antibody molecule is codon optimized. For example, the invention features a first and second nucleic acid encoding heavy and light chain variable regions, respectively, of an anti-TMEM antibody molecule chosen from one or more of, e.g., any of TA02, TC01, TC02, TD01, TE01, TG02, TM1, TE02.1, TE02.2, TE02.3, TE03, TE04, TE07, TE10 as defined in Tables 2-5, 8-11 or encoded by the nucleotide sequence in Tables 6, 7, 12, 13, or a sequence substantially identical thereto. For example, the nucleic acid can comprise a nucleotide sequence as set forth in Tables 6, 7, 12, 13, or a sequence substantially identical thereto (e.g., a sequence at least about 85%, 90%, 95%, 99% or more identical thereto, or which differs by no more than 3, 6, 15, 30, or 45 nucleotides from the sequences shown in Tables 6-7, 12, 13).

In other embodiments, the nucleic acid molecule comprises a nucleotide sequence that encodes a heavy chain variable domain and/or a heavy chain constant region comprising the amino acid sequence of any of TA02, TC01, TC02, TD01, TE01, TG02, TM1, TE02.1, TE02.2, TE02.3, TE03, TE04, TE07, TE10 as defined in Tables 2-5, 8-11 or encoded by the nucleotide sequence in Tables 6, 7, 12, 13; or a sequence substantially identical (e.g., a sequence at least about 85%, 90%, 95%, 99% or more identical) to any of the aforesaid sequences.

In other embodiments, the nucleic acid molecule comprises a nucleotide sequence that encodes a light chain variable domain and/or a light chain constant region comprising the amino acid sequence of any of TA02, TC01, TC02, TD01, TE01, TG02, TM1, TE02.1, TE02.2, TE02.3, TE03, TE04, TE07, TE10 as defined in Tables 2-5, 8-11 or the nucleotide sequence in Tables 6, 7, 12, 13, or a sequence substantially identical (e.g., a sequence at least about 85%, 90%, 95%, 99% or more identical) to any of the aforesaid sequences.

The aforesaid nucleotide sequences encoding the anti-TMEM heavy and light chain variable domain and constant regions can be present in a separate nucleic acid molecule, or in the same nucleic acid molecule. In certain embodiments, the nucleic acid molecules comprise a nucleotide sequence encoding a leader sequence.

In certain embodiments, the nucleic acid molecule comprises a nucleotide sequence encoding at least one, two, or three CDRs, or hypervariable loops, from a heavy chain variable region having an amino acid sequence as set forth in Tables 2-5, 8-11, or a sequence substantially homologous thereto (e.g., a sequence at least about 85%, 90%, 95%, 99% or more identical thereto, and/or having one, two, three or more substitutions, insertions or deletions, e.g., conserved substitutions).

In another embodiment, the nucleic acid molecule comprises a nucleotide sequence encoding at least one, two, or three CDRs, or hypervariable loops, from a light chain variable region having an amino acid sequence as set forth in Tables 2-5, 8-11 or a sequence substantially homologous thereto (e.g., a sequence at least about 85%, 90%, 95%, 99% or more identical thereto, and/or having one, two, three or more substitutions, insertions or deletions, e.g., conserved substitutions).

In yet another embodiment, the nucleic acid molecule comprises a nucleotide sequence encoding at least one, two, three, four, five, or six CDRs, or hypervariable loops, from heavy and light chain variable regions having an amino acid sequence as set forth in Tables 2-5, 8-11 or a sequence substantially homologous thereto (e.g., a sequence at least about 85%, 90%, 95%, 99% or more identical thereto, and/or having one, two, three or more substitutions, insertions or deletions, e.g., conserved substitutions).

In another embodiment, the nucleic acid molecule includes one or more heavy chain framework region (e.g., any of VHFW1 (type a), VHFW1 (type b), VHFW1 (type c), VHFW1 (type d), VHFW2 (type a), VHFW2 (type a'), VHFW2 (type b), VHFW2 (type c), VHFW2 (type d), VHFW2 (type e), VHFW3 (type a), VHFW3 (type b), VHFW3 (type c), VHFW3 (type d), VHFW3 (type e), or VHFW4, or any combination thereof, e.g., a framework combination as described herein) for any of TA02, TC01, TC02, TD01, TE01, TG02, TM1, TE02.1, TE02.2, TE02.3, TE03, TE04, TE07, TE10 as defined in Tables 2-5, 8-11, or a sequence substantially identical thereto. For example, the nucleic acid molecule can comprise a nucleotide sequence as set forth in Tables 6, 7, 12, 13, or a sequence substantially identical thereto (e.g., a sequence at least about 85%, 90%, 95%, 99% or more identical thereto, or which differs by no more than 3, 6, 15, 30, or 45 nucleotides from the sequences shown in Tables 6, 7, 12, 13).

In another embodiment, the nucleic acid molecule includes one or more light chain framework region (e.g., any of VLFW1 (type a), VLFW1 (type b), VLFW1 (type c), VLFW1 (type d), VLFW1 (type e), VLFW1 (type f), VLFW2 (type a), VLFW2 (type c), VLFW3 (type a), VLFW3 (type b), VLFW3 (type c), VLFW3 (type d), VLFW3 (type e), VLFW3 (type f), VLFW3 (type g), or VLFW4, or any combination thereof, e.g., a framework combination as described herein) for of any of E01, E02, E08, E14, E19, E20, E23, E24 or M1 as defined in Tables 2-5, 8-11, or a sequence substantially identical thereto. For example, the nucleic acid molecule can comprise a nucleotide sequence as set forth in Tables 6, 7, 12, 13, or a sequence substantially identical thereto (e.g., a sequence at least about 85%, 90%, 95%, 99% or more identical thereto, or which differs by no more than 3, 6, 15, 30, or 45 nucleotides from the sequences shown in Tables 6, 7, 12, 13).

In another embodiment, the nucleic acid molecule includes one or more heavy chain framework region and one or more light chain framework region as described herein. The heavy and light chain framework regions may be present in the same vector or separate vectors.

In another aspect, the application features host cells and vectors containing the nucleic acids described herein or modified for codon optimization according to known methods. The nucleic acids may be present in a single vector or separate vectors present in the same host cell or separate host cell. The host cell can be a eukaryotic cell, e.g., a mammalian cell, an insect cell, a yeast cell, or a prokaryotic cell, e.g., E. coli. For example, the mammalian cell can be a cultured cell or a cell line. Exemplary mammalian cells include lymphocytic cell lines (e.g., NSO), Chinese hamster ovary cells (CHO), COS cells, oocyte cells, and cells from a transgenic animal, e.g., mammary epithelial cell.

In one aspect, the invention features a method of providing an antibody molecule described herein. The method includes: providing a TMEM antigen (e.g., an antigen comprising at least a portion of a TMEM epitope); obtaining an antibody molecule that specifically binds to the TMEM polypeptide; and evaluating if the antibody molecule specifically binds to the TMEM polypeptide, or evaluating efficacy of the antibody molecule in modulating, e.g., inhibiting, the activity of the TMEM. The method can further include administering the antibody molecule to a subject, e.g., a human or non-human animal.

In another aspect, the invention provides, compositions, e.g., pharmaceutical compositions, which include a pharmaceutically acceptable carrier, excipient or stabilizer, and at least one of the anti-TMEM antibody molecules described herein. In one embodiment, the composition, e.g., the pharmaceutical composition, includes a combination of the antibody molecule and one or more agents, e.g., a therapeutic agent or other antibody molecule, as described herein. In one embodiment, the antibody molecule is conjugated to a label or a therapeutic agent.

The anti-TMEM antibody molecules disclosed herein can inhibit, reduce or neutralize one or more activities of IGFBP3 as indicated above. Thus, such antibody molecules can be used to treat or prevent disorders where the inhibition, reduction or neutralization of IGFBP3-induced activities in a subject is desired.

Uses of the Anti-TMEM Antibody Molecules

The present antibodies are used in methods of treatment of various disorders or conditions such as diabetes, as well as intestinal bowel diseases, malabsorption syndrome, inflammatory bowel disease, cachexia, Crohn's disease, ulcerative colitis, celiac disease, diabetic enteropathy.

Accordingly, in another aspect, a method of modulating the IGFBP3/TMEM219 axis in a subject is provided. The method comprises administering to the subject an anti-TMEM antibody molecule disclosed herein (e.g., a therapeutically effective amount of an anti-TMEM antibody molecule), alone or in combination with one or more agents or procedures, such that the IGFBP3/TMEM219 axis in the subject is modulated. In one embodiment, the antibody molecule inhibits, reduce or neutralize or block the IGFBP3/TMEM219 axis activity in the subject. The subject can be a mammal, e.g., a primate, preferably a higher primate, e.g., a human (e.g., a patient having, or at risk of having, a disorder described herein). In one embodiment, the subject is in need of inhibiting, reducing, neutralizing or blocking the IGFBP3/TMEM219 axis. In one embodiment, the subject has, or is at risk of, having a disorder described herein, e.g., diabetes, or inflammatory bowel disorder (IBD), malabsorption syndrome, irritable bowel disease, cachexia, celiac disease, diabetic enteropathy as described herein.

DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
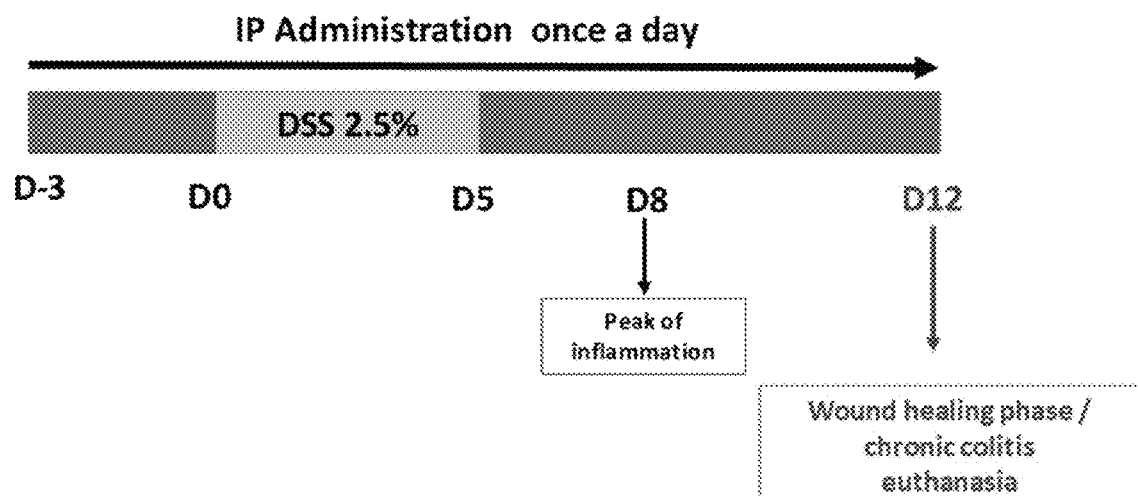
FIG. 1. Effect of newly generated anti-TMEM mAb on DSS-induced colitis in mice. Experimental timelines of DSS-induced colitis mice study: C57BL/6 mice were administered 2.5% DSS in the drinking water for 5 days and daily intraperitoneal administration of anti-TMEM mAbs 0.5 mg/mice starting 3 days before colitis induction until euthanasia occurring 7 days after the last DSS administration.

The antibodies of the invention specifically bind human TMEM219. As discussed herein, antibodies of the invention are collectively referred to as "anti-TMEM or anti-TMEM219 antibodies". All such antibodies are encompassed by the discussion herein. The respective antibodies can be used alone or in combination in the methods of the invention.

By "antibodies that specifically bind" TMEM219 is intended that the antibodies will not substantially cross react with another, nonhomologous, human polypeptide. By "not substantially cross react" is intended that the antibody or fragment has a binding affinity for a non-homologous protein which is less than 10%, more preferably less than 5%, and even more preferably less than 1%, of the binding affinity for TMEM219.

In various embodiments, an antibody that "specifically binds" TMEM219, as used herein, includes antibodies that bind TMEM219 or the extracellular portion thereof, such as ecto-TMEM, with a KD of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or about 0.5 nM, as measured with an Octet biolayer interferometry device or in a surface plasmon resonance assay, for example using the BIAcore™ system (Biacore Life Sciences division of GE Healthcare, Piscataway, NJ) or kinetic exclusion assays or any known method in the art.

The term "antibody" herein is used in the broadest sense understood in the art, including all polypeptides described as antibodies in (25), incorporated herein by reference.

For example, the term "antibody", as used herein, encompasses monoclonal antibodies, polyclonal antibodies, monospecific and multispecific antibodies (e.g., bispecific antibodies), and antibody fragments, so long as the fragment exhibits the desired antigen-binding activity (antigen-binding fragments). The term has its broadest art-recognized meaning and includes all known formats, including, without limitation: bivalent monospecific monoclonal antibodies, bivalent bispecific antibodies, trivalent trispecific antibodies, F(ab) fragments, F(ab)'2 fragments, scFv fragments, diabodies, single domain antibodies, including camelid VHH single domain antibodies, tandabs, and flexibodies.

The terms "antigen-binding fragment" of an antibody or equivalently "antigen-binding portion" of an antibody and the like, as used herein, include any naturally occurring, enzymatically obtainable, synthetic, or genetically engineered polypeptide or glycoprotein that comprises a portion of an antibody and that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen.

In particular embodiments, an antigen-binding fragment of an antibody comprises at least one variable domain covalently linked to at least one constant domain. Non-limiting, exemplary configurations of variable and constant domains that may be found within an antigen-binding fragment of an antibody include: (i) VH-CH1; (ii) VH-CH2; (iii) VH-CH3; (iv) VH-CH1-CH2; (v) VH-CH1-CH2-CH3; (vi) VH-CH2-CH3; (vii) VH-CL; (viii) VL-CH1; (ix) VL-CH2; (x) VL-CH3; (xi) VL-CH1-CH2; (xii) VL-CH1-CH2-CH3; (xiii) VL-CH2-CH3; and (xiv) VL-CL. In any configuration of variable and constant domains, including any of the exemplary configurations listed above, the variable and constant domains may be either directly linked to one another or may be linked by a full or partial hinge or linker region. A hinge region may in various embodiments consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody may in various embodiments comprise a homodimer or hetero-dimer (or other multimer) of any of the variable and constant domain configurations listed above in non-covalent association with one another and/or with one or more monomeric VH or VL domain (e.g., by disulfide bond(s)).

The term "antigen-binding fragment" of an antibody further includes single domain antibodies.

A single-domain antibody is an antibody fragment consisting of a single monomeric variable antibody domain. In some embodiments, the single-domain antibody is derived from the variable domain of the antibody heavy chain from camelids (also termed nanobodies, or VHH fragments). In some embodiments, the single-domain antibody is an autonomous human heavy chain variable domain (aVH) or VNAR fragments derived from sharks.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, and bivalent nanobodies), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a VH domain associated with a VL domain, the VH and VL domains may be situated relative to one another in any suitable arrangement. For example, the variable region may be dimeric and contain VH-VH, VH-VL or VL-VL dimers. Alternatively, the antigen-binding fragment of an antibody may contain a monomeric VH or VL domain.

The antibody or binding molecule of the invention can further be linked to an active substance, preferably a nanoparticle or a radionucleotide.

As used herein, the term "antigen binding molecule" refers in its broadest sense to a molecule that specifically binds an antigenic determinant. Examples of antigen binding molecules are antibodies, including antigen-binding antibody fragments, and scaffold antigen binding proteins.

The term "antigen binding moiety" refers to the portion of an antigen binding molecule that specifically binds to an antigenic determinant. Antigen binding moieties include antibodies and antigen-binding fragments thereof, such as scFv, that are capable of specific binding to an antigen on a target cell. In a particular aspect, the antigen binding moiety is able to direct the entity to which it is attached, such as a cell, to a target site.

In addition, antigen binding moieties capable of specific binding to a target cell antigen include scaffold antigen binding proteins as defined herein below, e.g. binding domains which are based on designed repeat proteins or designed repeat domains such as designed ankyrin repeat proteins (DARPins) (see e.g. WO 2002/020565) or Lipocalins (Anticalin).

Designed Ankyrin Repeat Proteins (DARPins), which are derived from Ankyrin, which is a family of proteins that mediate attachment of integral membrane proteins to the cytoskeleton. A single ankyrin repeat is a 33-residue motif consisting of two alpha-helices and a beta-turn. They can be engineered to bind different target antigens by randomizing residues in the first alpha-helix and a beta-turn of each repeat. Their binding interface can be increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028.

In certain embodiments, antibodies and antigen binding molecules provided herein are altered to increase or decrease the extent to which the antigen binding moiety is glycosylated. Glycosylation variants of the molecules may be conveniently obtained by altering the amino acid sequence such that one or more glycosylation sites is created or removed. Where the antigen binding molecule comprises an Fc region, the carbohydrate attached thereto may be altered. In one aspect, variants of antigen binding molecules are provided having a carbohydrate structure that lacks fucose attached (directly or indirectly) to an Fc region. Such fucosylation variants may have improved ADCC function, see e.g. US Patent Publication Nos. US 2003/0157108 (Presta, L.) or US 2004/0093621 (Kyowa Hakko Kogyo Co., Ltd). Further variants of antigen binding molecules of the invention include those with bisected oligosaccharides, e.g., in which a biantennary oligosaccharide attached to the Fc region is bisected by GlcNAc. Such variants may have reduced fucosylation and/or improved ADCC function, see for example WO 2003/011878 (Jean-Mairet et al.); U.S. Pat. No. 6,602,684 (Umana et al.); and US 2005/0123546 (Umana et al.). Variants with at least one galactose residue in the oligosaccharide attached to the Fc region are also provided. Such antibody variants may have improved CDC function and are described, e.g., in WO 1997/30087 (Patel et al.); WO 1998/58964 (Raju, S.); and WO 1999/22764 (Raju, S.).

In certain embodiments, it may be desirable to create cysteine engineered variants of the antibody or antigen binding molecule of the invention, e.g., "thioMAbs," in which one or more residues of the molecule are substituted with cysteine residues. In particular embodiments, the substituted residues occur at accessible sites of the molecule. By substituting those residues with cysteine, reactive thiol groups are thereby positioned at accessible sites of the antibody and may be used to conjugate the antibody to other moieties, such as drug moieties or linker-drug moieties, to create an immunoconjugate.

In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antigen binding molecules may be generated as described, e.g., in U.S. Pat. No. 7,521,541.

In certain aspects, the antibody or antigen binding molecules provided herein may be further modified to contain additional non-proteinaceous moieties that are known in the art and readily available. The moieties suitable for derivatization of the antibody or antigen binding molecule include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another aspect, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed. In another aspect, immunoconjugates of the antigen binding molecules provided herein may be obtained. An "immunoconjugate" is an antibody conjugated to one or more heterologous molecule(s), including but not limited to a cytotoxic agent.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity. In certain embodiments, the constant region is an IgG1, IgG2, IgG3, IgG4 constant region.

The invention encompasses in various embodiments antibodies having one or more mutations in the hinge, CH2 or CH3 region which may be desirable, for example, in production, to improve the yield of the desired antibody form. In some embodiments, for example, the antibodies described herein comprise a human IgG4 constant region. In particular embodiments, the IgG4 constant region has a single amino acid substitution in the hinge region of the human IgG4 hinge which reduced Fab arm exchange (Angal et al. (1993) Molecular Immunology 30:105) to levels typically observed using a human IgG1 hinge.

In certain embodiments, the antibody comprises one or more mutations in the constant region that increase serum half-life, including those described in U.S. Pat. Nos. 7,083,784, 8,323,962 and Dall'Aqua et al., *J. Biol. Chem.* 281 (33):23514-23524 (2006); Hinton et al., *J. Immunology* 176:346-356 (2006); Yeung et al., *J. Immunology* 182:7663-7671 (2009); and Petkova et al., *Intn'l Immunology*, 18: 1759-1769 (2006), incorporated herein by reference in their entireties.

The term "human antibody", as used herein, is intended to include antibodies having variable and constant regions derived from human germline immunoglobulin sequences. The human antibodies featured in the invention may in various embodiments nonetheless include amino acid residues not encoded by human germline immunoglobulin sequences (e.g., mutations introduced by random or site-specific mutagenesis in vitro or by somatic mutation in vivo), for example in the CDRs, and in some embodiments, CDR3. However, the term "human antibody", as used herein, is not intended to include antibodies in which CDR sequences are derived from the germline of another mammalian species, such as a mouse, which have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295, incorporated herein by reference in its entirety,) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody." In various embodiments, the isolated antibody also includes an antibody in situ within a recombinant cell. In other embodiments, isolated antibodies are antibodies that have been subjected to at least one purification or isolation step. In various embodiments, an isolated antibody may be substantially free of other cellular material and/or chemicals.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The anti-TMEM219 antibodies described herein and useful for the methods featured herein may in various embodiments include one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases.

The present invention includes in various embodiments antibodies and methods involving the use of antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations").

Numerous antibodies and antigen-binding fragments may be constructed which comprise one or more individual germline mutations or combinations thereof. In certain embodiments, all of the framework and/or CDR residues within the VH and/or VL domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies may contain any combination of two or more germline mutations within the framework and/or CDR regions, e.g., wherein certain individual residues are mutated to the corresponding residue of a certain germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. The use of antibodies and antigen-binding fragments obtained in this general manner are encompassed within the present invention.

The present invention also includes anti-TMEM219 antibodies and methods involving the use of anti-TMEM219 antibodies comprising variants of any of the HCVR, LCVR, and/or CDR amino acid sequences disclosed herein having one or more conservative substitutions. For example, the present invention includes the use of anti-IL-6R antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein. The term "bioequivalent" as used herein, refers to a molecule having similar bioavailability (rate and extent of availability) after administration at the same molar dose and under similar conditions (e.g., same route of administration), such that the effect, with respect to both efficacy and safety, can be expected to be essentially same as the comparator molecule. Two pharmaceutical compositions comprising an anti-IGFBP3 antibody are bioequivalent if they are pharmaceutically equivalent, meaning they contain the same amount of active ingredient (e.g., IGFBP3 antibody), in the same dosage form, for the same route of administration and meeting the same or comparable standards. Bioequivalence can be determined, for example, by an in vivo study comparing a pharmacokinetic parameter for the two compositions. Parameters commonly used in bioequivalence studies include peak plasma concentration (Cmax) and area under the plasma drug concentration time curve (AUC).

The invention in certain embodiments relates to antibodies and methods comprising administering to the subject an antibody which comprises the heavy chain variable region comprising a sequence chosen from the group of: SEQ ID NO:32 to SEQ ID NO:37 or SEQ ID NO:88 to SEQ ID NO:95 and the light chain variable region comprising a sequence chosen from the group of: SEQ ID NO:38 to SEQ ID NO:43 or SEQ ID NO:96 to SEQ ID NO:103. The disclosure provides pharmaceutical compositions comprising such antibody, and methods of using these compositions.

The antibody is administered to the subject in various embodiments in a formulation comprising suitable carriers, excipients, and other agents to provide improved transfer, delivery, tolerance, and the like, and suitable for an intravenous or subcutaneous injection.

The injectable preparations may be prepared by methods publicly known. For example, injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 20 or 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injectable preparation thus prepared can be filled in an appropriate ampoule.

The antibody according to the invention can be administered to the subject using any acceptable device or mechanism. For example, the administration can be accomplished using a syringe and needle or with a reusable pen and/or autoinjector delivery device. The methods of the present invention include the use of numerous reusable pen and/or autoinjector delivery devices to administer an antibody (or pharmaceutical formulation comprising the antibody). Examples of such devices include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and Ill (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (Sanofi-Aventis, Frankfurt, Germany), to name only a few. Examples of disposable pen and/or autoinjector delivery devices having applications in subcutaneous delivery of a pharmaceutical composition of the present invention include, but are not limited to, the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L.P.), the HUMIRA™ Pen (Abbott Labs, Abbott Park, IL), the DAI® Auto Injector (SHL Group) and any auto-injector featuring the PUSHCLICK™ technology (SHL Group), to name only a few.

In one embodiment, the antibody is administered with a prefilled syringe. In another embodiment, the antibody is administered with a prefilled syringe containing a safety system. For example, the safety system prevents an accidental needlestick injury. In various embodiments, the antibody is administered with a prefilled syringe containing an ERIS™ safety system (West Pharmaceutical Services Inc.). See also U.S. Pat. Nos. 5,215,534 and 9,248,242, incorporated herein by reference in their entireties. In another embodiment, the antibody is administered with an auto-injector. In various embodiments, the antibody is administered with an auto-injector featuring the PUSHCLICK™ technology (SHL Group). In various embodiments, the auto-injector is a device comprising a syringe that allows for administration of a dose of the composition and/or antibody to a subject. See also U.S. Pat. Nos. 9,427,531 and 9,566,395, incorporated herein by reference in their entireties.

According to the invention, "subject" means a human subject or human patient.

EXAMPLES

Methods

Recombinant Proteins

Recombinant human IGFBP3 was obtained from Life Technologies (IGFBP3, Life Technologies, 10430H07H5). Ecto-TMEM219, which is the extracellular domain of the TMEM219 receptor, was obtained through Genescript's customized protein service. The protein, produced in *E. coli*, has the following amino acid sequence:

```
Human Ecto-TMEM amino acid sequence:
                                      (SEQ ID NO: 125)
THRTGLRSPDIPQDWVSFLRSFGQLTLCPRNGTVT

GKWRGSHVVGLLTTLNFGDGPDRNKTRTFQATVLG

SQMGLKGSSAGQLVLITARVTTERTAGTCLYFSAV

PGILPSSQPPISCSEEGAGNATLSPRMGEECVSVW

SHEGLVLTKLLTSEELALCGSR

Murine Ecto-TMEM amino acid sequence:
                                      (SEQ ID NO: 126)
THTTGLRSPDIPQDWVSFLRSFGQLSLCPMNETVT

GTWQGPHVVGLLTTLNFGDGPDRNKTQTFQAKIHG

SQIGLTGSSAGESVLVTARVASGRTPGTCLYFSGV

PKVLPSSQPPISCSEEGVGNATLSPVMGEECVRVW

SHERLVLTELLTSEELALCGS
```

Monoclonal Antibodies Development from Naïve Human Phage-Display Libraries

Monoclonal anti-TMEM antibodies were selected from naïve human phage-display libraries using human EctoTMEM219 (obtained from Genescript's customized protein service) as antigen for the screening. The EctoTMEM antigen was immobilized onto 96-well ELISA plates either by direct adsorption or capturing via an anti-ectoTMEM polyclonal antibody. After washing and blocking of the wells with BSA, the antibody-phage libraries were added. The libraries were cleared from sticky or cross-reactive antibody-phage previously.

The phage that displayed an antigen-specific antibody were captured on the plate surface. After removal of unbound/weakly bound phage by washing with PBS-T, antigen-specific phage was eluted and amplified. This amplified library subset was again selected for target binding under more stringent conditions, i.e. the number of washing steps were increased to clear non-bound or weakly bound phage. In total, three selection rounds were performed to enrich antigen specific antibody-phage.

At the end of the selection process, the selection output was screened for antigen-specific antibodies by ELISA. For this purpose, monoclonal scFv antibodies were produced from clones of the selection output. These were then tested for specific antigen binding by ELISA. 15 target specific hits were identified. 11 of them contained a unique CDR sequence. These were cloned into a mammalian scFv-Fc expression vector, resulting in a genetic fusion of the scFv with a human IgG4 Fc.

6 of those antibodies could be produced in the scFv-Fc format by transient transfection of HEK293 cells. The antibodies were purified by affinity chromatography (Protein A) and re-buffered in PBS. The protein concentration was determined by UV/VIS spectrometry and purity was checked by Coomassie staining.

Monoclonal Antibodies Development Hybridoma-Based

Monoclonal anti-TMEM antibodies were identified through the utilization of transgenic mouse, where the relevant human immunoglobulin sequences have been introduced into the genome of the animal by genetic engineering, the Trianni Mouse™ (Trianni).

Through use of such technology, chimeric monoclonal antibodies containing the full repertoire of human heavy- and light-chain variable domains and the retention of the mouse constant domains were produced.

Essentially, two cohorts of Trianni Mouse™ (Cohort 1: ALD/MDP adjuvant and Cohort 2: SAS/Ribi adjuvant) were immunized with human EctoTMEM219 (Genescript's customized protein service), two injections a week for 4 weeks then 2 weeks extension at one injection a week. Then, lymphatic cells (such as B-cells) were recovered from the mice that express antibodies, such cells were fused with a myeloid-type cell line to prepare immortal hybridoma cell lines, and such hybridoma cell lines were screened and selected to identify hybridoma cell lines that produce antibodies specific to human Ecto-TMEM219 by ELISA. Hybridoma cell lines that were reactive for the antigen of interest were expanded. Sequencing was accomplished by RNA isolation, followed by cDNA sequencing of the human VH and human VK using Sanger sequencing methods.

Antibodies can be expressed in cell lines other than hybridoma cell lines. Sequences encoding antibodies can be used for transformation of a suitable mammalian host cell.

Method of Expressing Recombinant Protein in CHO Cells

The corresponding TC01 and TM1 cDNAs were cloned into evitria's vector system using conventional (non-PCR based) cloning techniques to produce a fully human IgG4 mAb. The evitria vector plasmids were gene synthesized. Plasmid DNA was prepared under low-endotoxin conditions based on anion exchange chromatography. Correctness of the sequences was verified with Sanger sequencing (with up to two sequencing reactions per plasmid depending on the size of the cDNA.)

Suspension-adapted CHO K1 cells (evitria) was used for production. The seed was grown in eviGrow medium, a chemically defined, animal-component free, serum-free medium. Cells were transfected with eviFect, evitria's custom-made, proprietary transfection reagent, and cells were grown after transfection in eviMake, an animal-component free, serum-free medium, at 37° C. and 5% CO2 for 7 days. Supernatant was harvested by centrifugation and subsequent filtration (0.2 μm filter).

The antibody was purified using MabSelect™ SuRe™ with Dulbecco's PBS (Lonza BE17-512Q) as wash buffer and 0.1 M Glycine pH 3.5 as elution buffer. Subsequent size exclusion chromatography was performed on a HiLoad Superdex 200 pg column using the final buffer as running buffer.

Monomericity was determined by analytical size exclusion chromatography with an Agilent AdvanceBio SEC column (300A 2.7 um 7.8×300 mm) and DPBS as running buffer at 0.8 ml/min.

The sequences of the 6 novel anti-TMEM antibodies from human phage-display libraries are reported in Tables 2-7 below.

TABLE 2

VH CDR Sequences of exemplified antibodies

| Antibody | CDR1 | CDR2 | CDR3 |
|---|---|---|---|
| TA02 | SYAIS (SEQ ID NO. 1) | GIIPIFGTA NYAQKFQG (SEQ ID NO. 2) | GDIAAAGRK GLPIYYMDV (SEQ ID NO. 3) |
| TC01 | SYGI (SEQ ID NO. 4) | WISAYNGNTN YAQKLQG (SEQ ID NO. 5) | WGRWLAHDY (SEQ ID NO. 6) |

TABLE 2-continued

VH CDR Sequences of exemplified antibodies

| Antibody | CDR1 | CDR2 | CDR3 |
|---|---|---|---|
| TC02 | SYAIS (SEQ ID NO. 1) | GIIPIFGTA NYAQKFQG (SEQ ID NO. 2) | PSGYYIYDAFDI (SEQ ID NO. 7) |
| TD01 | SYGIS (SEQ ID NO. 8) | WISAYNGNT NYAQKLQG (SEQ ID NO. 5) | DLGWPDDY (SEQ ID NO. 9) |
| TE01 | DYGMS (SEQ ID NO. 10) | GINWNGGST GYADSVKG (SEQ ID NO. 11) | DRLRYCSST SCYIPDY (SEQ ID NO. 12) |
| TG02 | SYGIS (SEQ ID NO. 8) | WISAYNGNT NYAQKLQG (SEQ ID NO. 5) | VGSTYDFWS GAYYYYGMD V (SEQ ID NO. 13) |

TABLE 3

VL CDR Sequences of exemplified antibodies

| Antibody | CDR1 | CDR2 | CDR3 |
|---|---|---|---|
| TA02 | QASQDISNYLN (SEQ ID NO. 14) | AASSLQS (SEQ ID NO. 15) | QQSYSTPT (SEQ ID NO. 16) |
| TC01 | SGDKLGNKNAY (SEQ ID NO. 17) | QSTRRPS (SEQ ID NO. 18) | QAWDSSSGWEV (SEQ ID NO. 19) |
| TC02 | GASQSVS SSYLA (SEQ ID NO. 20) | DASSRAT (SEQ ID NO. 21) | HQYNNWPRT (SEQ ID NO. 22) |
| TD01 | SGSSSNI GSNYVY (SEQ ID NO. 23) | RNNQRPS (SEQ ID NO. 24) | AAWDDSLNGVV (SEQ ID NO. 25) |
| TE01 | KSSQSVLDS SNNKNYVA (SEQ ID NO. 26) | WASTRES (SEQ ID NO. 27) | QQYYTTRWT (SEQ ID NO. 28) |
| TG02 | RASQGIRNDLG (SEQ ID NO. 29) | DASNLET (SEQ ID NO. 30) | QQYDNLPLT (SEQ ID NO. 31) |

CDR definition is also provided using annotation tool from http://www.abysis.org/ based on full VH and VL amino acid sequences as defined in Tables 4, 5, 10 and 11. For example, the VH amino acid sequence of any antibody disclosed herein is plugged into the annotation tool and Kabat defined CDR sequences are provided.

Below is shown the example in reference to SEQ ID No. 33 (VH of TC01).

TABLE 3.1

Kabat defined CDR sequences Residues
Regions Definition Kabat

| Region | Sequence Fragment | Residues |
|---|---|---|
| HFR1 | QIQLVQSGAEVKKPGASV KVSCKASGYTFT (SEQ ID No. 127) | 1-30 |
| CDR-H1 | SYGIS (SEQ ID No. 8) | 31-35 |
| HFR2 | WVRQAPGQGLEWMG (SEQ ID No. 128) | 36-49 |
| CDR-H2 | WISAYNGNTNYAQKLQG (SEQ ID No. 5) | 50-66 |
| HFR3 | RVTMTTDTSTSTAYMELR SLRSDDTAVYYCAR (SEQ ID No. 129) | 67-98 |
| CDR-H3 | WGRWLAHDY (SEQ ID No. 6) | 99-107 |
| HFR4 | WGQGTLVTVSS (SEQ ID No. 130) | 108-118 |

The VH amino acid sequence of any antibody disclosed herein may also be plugged into the annotation tool and IMGT defined CDR sequences are provided.

Below is shown the example in reference to SEQ ID No. 33 (VH of TC01).

TABLE 3.2

IMGT defined CDR sequences Residues
Regions Definition IMGT

| Region | Sequence Fragment | Residues |
|---|---|---|
| HFR1 | QIQLVQSGAEVKKPGAS VKVSCKAS (SEQ ID No. 131) | 1-25 |
| CDR-H1 | GYTFTSYG (SEQ ID No. 132) | 26-33 |
| HFR2 | ISWVRQAPGQGLEWMGW (SEQ ID No. 133) | 34-50 |
| CDR-H2 | ISAYNGNT (SEQ ID No. 134) | 51-58 |
| HFR3 | NYAQKLQGRVTMTTDTST STAYMELRSLRSDDTAVY YC (SEQ ID No. 135) | 59-96 |
| CDR-H3 | ARWGRWLAHDY (SEQ ID No. 136) | 99-107 |
| HFR4 | WGQGTLVTVSS (SEQ ID No. 137) | 108-118 |

In addition, the VH amino acid sequence of any antibody disclosed herein may also be plugged into the annotation tool and the "All, side by side" defined CDR sequences are provided.

Below is shown the example in reference to SEQ ID No. 33 (VH of TC01).

TABLE 3.3

All, side by side defined CDR sequences
Regions Definition All, side by side

| Region | Definition | Sequence Fragment | Residues |
|---|---|---|---|
| HFR1 | Chothia | QIQLVQSGAEVKKPGASVKVSCKAS----- (SEQ ID No. 131) | 1-25 |
| | AbM | QIQLVQSGAEVKKPGASVKVSCKAS----- (SEQ ID No. 131) | 1-25 |
| | Kabat | QIQLVQSGAEVKKPGASVKVSCKASGYTFT (SEQ ID No. 127) | 1-30 |
| | Contact | QIQLVQSGAEVKKPGASVKVSCKASGYTF- (SEQ ID No. 138) | 1-29 |
| | IMGT | QIQLVQSGAEVKKPGASVKVSCKAS----- (SEQ ID No. 131) | 1-25 |
| CDR-H1 | Chothia | GYTFTSY--- (SEQ ID No. 139) | 26-32 |
| | AbM | GYTFTSYGIS (SEQ ID No. 140) | 26-35 |
| | Kabat | -----SYGIS (SEQ ID No. 8) | 31-35 |
| | Contact | ----TSYGIS (SEQ ID No. 141) | 30-35 |
| HFR2 | IMGT | GYTFTSYG-- (SEQ ID No. 132) | 26-33 |
| | Chothia | GISWVRQAPGQGLEWMGWI (SEQ ID No. 142) | 33-51 |
| | AbM | ---WVRQAPGQGLEWMG-- (SEQ ID No. 128) | 36-49 |
| | Kabat | ---WVRQAPGQGLEWMG-- (SEQ ID No. 128) | 36-49 |

TABLE 3.3-continued

All, side by side defined CDR sequences
Regions Definition All, side by side

| Region | Definition | Sequence Fragment | Residues |
|---|---|---|---|
| | Contact | ---WVRQAPGQGLE----- (SEQ ID No. 143) | 36-46 |
| | IMGT | -ISWVRQAPGQGLEWMGW- (SEQ ID No. 133) | 34-50 |
| CDR-H2 | Chothia | -----SAYNGN--------- (SEQ ID No. 144) | 52-57 |
| | AbM | ---WISAYNGNTN------- (SEQ ID No. 145) | 50-59 |
| | Kabat | ---WISAYNGNTNYAQKLQG (SEQ ID No. 5) | 50-66 |
| | Contact | ---WMGWISAYNGNTN---- (SEQ ID No. 146) | 47-59 |
| | IMGT | -------ISAYNGNT----- (SEQ ID No. 134) | 51-58 |
| HFR3 | Chothia | TNYAQKLQGRVTMTTDTSTSTAYMELRSLRSDDTAVYYCAR (SEQ ID No. 147) | |
| | AbM | --YAQKLQGRVTMTTDTSTSTAYMELRSLRSDDTAVYYCAR (SEQ ID No. 148) | 60-98 |
| | Kabat | ---------RVTMTTDTSTSTAYMELRSLRSDDTAVYYCAR (SEQ ID No. 129) | 67-98 |
| | Contact | --YAQKLQGRVTMTTDTSTSTAYMELRSLRSDDTAVYYC-- (SEQ ID No. 149) | 60-96 |
| | IMGT | -NYAQKLQGRVTMTTDTSTSTAYMELRSLRSDDTAVYYC-- (SEQ ID No. 135) | 59-96 |
| CDR-H3 | Chothia | --WGRWLAHDY (SEQ ID No. 6) | 99-107 |
| | AbM | --WGRWLAHDY (SEQ ID No. 6) | 99-107 |
| | Kabat | --WGRWLAHDY (SEQ ID No. 6) | 99-107 |
| | Contact | ARWGRWLAHD-(SEQ ID No. 150) | 97-106 |
| | IMGT | ARWGRWLAHDY (SEQ ID No. 136) | 97-107 |
| HFR4 | Chothia | -WGQGTLVTVSS (SEQ ID No. 137) | 108-118 |
| | AbM | -WGQGTLVTVSS (SEQ ID No. 137) | 108-118 |
| | Kabat | -WGQGTLVTVSS (SEQ ID No. 137) | 108-118 |
| | Contact | YWGQGTLVTVSS (SEQ ID No. 151) | 107-118 |
| | IMGT | -WGQGTLVTVSS (SEQ ID No. 137) | 108-118 |

CDR definition provided using annotation tool from http://www.abysis.org/ based on full VL amino acid of TC01 (SEQ ID No. 39) is also reported.

TABLE 3.4

All, side by side defined CDR sequences

| Region | Definition | Sequence Fragment | Residues |
|---|---|---|---|
| LFR1 | Chothia | QAVLTQPPSVSVSPGQTASITC------ (SEQ ID No. 152) | 1-22 |
| | AbM | QAVLTQPPSVSVSPGQTASITC------ (SEQ ID No. 152) | 1-22 |
| | Kabat | QAVLTQPPSVSVSPGQTASITC------ (SEQ ID No. 152) | 1-22 |
| | Contact | QAVLTQPPSVSVSPGQTASITCSGDKLG (SEQ ID No. 153) | 1-28 |

TABLE 3.4-continued

All, side by side defined CDR sequences

| Region | Definition | Sequence Fragment | Residues |
|---|---|---|---|
| | IMGT | QAVLTQPPSVSVSPGQTASITCSGD--- (SEQ ID No. 154) | 1-25 |
| CDR-L1 | Chothia | SGDKLGNKNAY-- (SEQ ID No. 17) | 23-33 |
| | AbM | SGDKLGNKNAY-- (SEQ ID No. 17) | 23-33 |
| | Kabat | SGDKLGNKNAY-- (SEQ ID No. 17) | 23-33 |
| | Contact | ------NKNAYWY (SEQ ID No. 155) | 29-35 |
| | IMGT | ---KLGNKN---- (SEQ ID No. 156) | 26-31 |
| LFR2 | Chothia | --WYQQKPGQSPVLVMY (SEQ ID No. 156) | 34-48 |
| | AbM | --WYQQKPGQSPVLVMY (SEQ ID No. 156) | 34-48 |
| | Kabat | --WYQQKPGQSPVLVMY (SEQ ID No. 156) | 34-48 |
| | Contact | ----QQKPGQSPV---- (SEQ ID No. 157) | 36-44 |
| | IMGT | AYWYQQKPGQSPVLVMY (SEQ ID No. 158) | 32-48 |
| CDR-L2 | Chothia | ----QSTRRPS (SEQ ID No. 18) | 49-55 |
| | AbM | ----QSTRRPS (SEQ ID No. 18) | 49-55 |
| | Kabat | ----QSTRRPS (SEQ ID No. 18) | 49-55 |
| | Contact | LVMYQSTRRP- (SEQ ID No. 159) | 45-54 |
| | IMGT | ----QS----- | 49-50 |
| LFR3 | Chothia | -----GTPERFSASNSGNTATLTISGTQAMDEADYYC (SEQ ID No. 160) | 56-87 |
| | AbM Kabat | -----GIPERFSASNSGNTATLTISGTQAMDEADYYC (SEQ ID No. 160) | 56-87 |
| | | -----GIPERFSASNSGNTATLTISGTQAMDEADYYC (SEQ ID No. 160) | 56-87 |
| | Contact IMGT | ----SGIPERFSASNSGNTATLTISGTQAMDEADYYC (SEQ ID No. 161) | 55-87 |
| | | TRRPSGIPERFSASNSGNTATLTISGTQAMDEADYYC (SEQ ID No. 162) | 51-87 |
| CDR-L3 | Chothia | QAWDSSSGWEV (SEQ ID No. 19) | 88-98 |
| | AbM | QAWDSSSGWEV (SEQ ID No. 19) | 88-98 |
| | Kabat | QAWDSSSGWEV (SEQ ID No. 19) | 88-98 |
| | Contact | QAWDSSSGWE- (SEQ ID No. 163) | 88-97 |
| LFR4 | IMGT | QAWDSSSGWEV (SEQ ID No. 19) | 88-98 |
| | Chothia | -FGGGTKLTVL (SEQ ID No. 164) | 99-108 |
| | AbM | -FGGGTKLTVL (SEQ ID No. 164) | 99-108 |
| | Kabat | -FGGGTKLTVL (SEQ ID No. 164) | 99-108 |
| | Contact | VFGGGTKLTVL (SEQ ID No. 165) | 98-108 |
| | IMGT | -FGGGTKLTVL (SEQ ID No. 164) | 99-108 |

TABLE 4

VH amino acid sequences of exemplified antibodies

| Antibody | AA of VH |
|---|---|
| TA02 | QVQLVQSGAEVKRPGSSVKVSCKASGGTFS SYAISWVRQAPGQGLEWMGGIIPIFGTANY AQKFQGRVTITADESTSTAYMELSNLRSED TAVYYCARGDIAAAGRKGLPIYYMDVWGKG TTVTVSS (SEQ ID NO. 32) |
| TC01 | QIQLVQSGAEVKKPGASVKVSCKASGYTFT SYGISWVRQAPGQGLEWMGWISAYNGNTNY AQKLQGRVTMTTDTSTSTAYMELRSLRSDD TAVYYCARWGRWLAHDYWGQGTLVTVSS (SEQ ID NO. 33) |
| TC02 | QMQLVQSGAEVKKPGSSVKVSCKASGGTFS SYAISWVRQAPGQGLEWMGGIIPIFGTANY AQKFQGRVTITADESTSTAYMELSSLRSED TAVYYCASPSGYYIYDAFDIWGQGTMVTVS S (SEQ ID NO. 34) |
| TD01 | QVQLVQSGAEVKKPGASVKVSCKASGYTFT SYGISWVRQAPGQGLEWMGWISAYNGNTNY AQKLQGRVTMTTDTSTSTAYMELRSLRSDD TAVYYCARDLGWPDDYWGQGTLVTVSS (SEQ ID NO. 35) |
| TE01 | EVQLLESGGGVVRPGGSLRLSCAASGFTFD DYGMSWVRQAPGKGLEWVSGINWNGGSTGY ADSVKGRFTISRDNSKNTLYLQMNSLRAED TAAYYCAKDRLRYCSSTSCYIPDYWGQGTL VTVSS (SEQ ID NO. 36) |
| TG02 | QVQLVQSGAEVKRPGASVKVSCKASGYTFT SYGISWVRQAPGQGLEWMGWISAYNGNTNY AQKLQGRVTMTTDTSTSTAYMELRSLRSDD TA VYYCARVGSTYDFWSGAYYYYGMDVWGQGT TVTVSS (SEQ ID NO. 37) |

TABLE 5

VL amino acid sequences of exemplified antibodies

| Antibody | AA of VL |
|---|---|
| TA02 | DIQMTQSPSSLSASVGDRVTITCQA SQDISNYLNWYQQKPGKAPKLLIYA ASSLQSGVPSRFSGSGSGTDFTLTI SSLQPEDFATYYCQQSYSTPTFGQG TKLEIK (SEQ ID NO. 38) |
| TC01 | QAVLTQPPSVSVSPGQTASITCSGD KLGNKNAYWYQQKPGQSPVLVMYQS TRRPSGIPERFSASNSGNTATLTIS GTQAMDEADYYCQAWDSSSGWEVFG GGTKLTVL (SEQ ID NO. 39) |
| TC02 | ETTLTQSPATLSLSPGERATLSCGA SQSVSSSYLAWYQQKPGLAPRLLIY DASSRATGIPDRFSGSGSGTDFTLT ISRLEPEDFAVYYCHQYNNWPRTFG QGTKVEIK (SEQ ID NO. 40) |
| TD01 | QPVLTQPPSASGTPGQRVTISCSGS SSNIGSNYVYWYQQLPGTAPKLLIY RNNQRPSGVPDRFSGSKSGTSASLA ISGLRSEDEADYYCAAWDDSLNGVV FGGGTKLTVL (SEQ ID NO. 41) |
| TE01 | DIQMTQSPDSLAVSLGERATINCKS SQSVLDSSNNKNYVAWFQQKPGQPP KLLIYWASTRESGVPDRFSGSGSGT DFTLTISSLQAEDVAVYYCQQYTT RWTFGQGTKVEIK (SEQ ID NO. 42) |
| TG02 | DIVMTQSPSSLSASVGDRVTITCRA SQGIRNDLGWYQQKPGKAPKLLIYD ASNLETGVPSRFSGSGSGTDFTFTI SSLQPEDIATYYCQQYDNLPLTFGG GTKVEIK (SEQ ID NO. 43) |

TABLE 6

VH nucleotide sequences of exemplified antibodies

| Antibody | DNA of VH |
|---|---|
| TA02 | CAGGTCCAGCTGGTACAGTCTGGGGCTGAG GTGAAGAGGCCTGGGTCCTCGGTGAAGGTC TCCTGCAAGGCTTCTGGAGGCACCTTCAGC AGCTATGCTATCAGCTGGGTGCGACAGGCC CCTGGACAAGGGCTTGAGTGGATGGGAGGG ATCATCCCTATCTTTGGTACAGCAAACTAC GCACAGAAGTTCCAGGGCAGAGTCACGATT ACCGCGGACGAATCCACGAGCACAGCCTAC ATGGAGCTGAGCAACCTGAGATCTGAGGAC ACGGCCGTGTATTACTGTGCGAGAGGGGAT ATAGCAGCAGCTGGTAGGAAAGGACTGCCC ATCTACTACATGGACGTCTGGGGCAAAGGG ACCACGGTCACCGTCTCCTCA (SEQ ID NO. 44) |
| TC01 | CAAATCCAGCTGGTACAGTCTGGGGCTGAG GTGAAGAAGCCTGGGGCCTCAGTGAAGGTC TCCTGCAAGGCTTCTGGTTACACCTTTACC AGCTACGGTATCAGCTGGGTGCGACAGGCC CCTGGACAAGGGCTTGAGTGGATGGGATGG ATCAGCGCTTACAATGGTAACACAAACTAT GCACAGAAGCTCCAGGGCAGAGTCACCATG ACCACAGACACATCCACGAGCACAGCCTAC ATGGAGCTGAGGAGCCTGAGATCTGACGAC ACGGCCGTGTATTACTGTGCGAGGTGGGGT AGGTGGCTGGCTCATGACTACTGGGGCCAG GGAACCCTGGTCACCGTCTCCTCA (SEQ ID NO. 45) |
| TC02 | CAGATGCAGCTGGTGCAGTCTGGGGCTGAG GTGAAGAAGCCTGGGTCCTCGGTGAAGGTC TCCTGCAAGGCTTCTGGAGGCACCTTCAGC AGCTATGCTATCAGCTGGGTGCGACAGGCC CCTGGACAAGGGCTTGAGTGGATGGGAGGG ATCATCCCTATCTTTGGTACAGCAAACTAC GCACAGAAGTTCCAGGGCAGAGTCACGATT ACCGCGGACGAATCCACGAGCACAGCCTAC ATGGAGCTGAGCAGCCTGAGATCTGAGGAC ACGGCCGTGTATTACTGTGCGAGCCCAAGT GGTTATTATATTTATGATGCTTTTGATATC TGGGGCCAAGGGACAATGGTCACCGTCTCT TCA (SEQ ID NO. 46) |
| TD01 | CAGGTCCAGCTGGTGCAGTCTGGAGCTGAG GTGAAGAAGCCTGGGGCCTCAGTGAAGGTC TCCTGCAAGGCTTCTGGTTACACCTTTACC AGCTACGGTATCAGCTGGGTGCGACAGGCC CCTGGACAAGGGCTTGAGTGGATGGGATGG ATCAGCGCTTACAATGGTAACACAAACTAT GCACAGAAGCTCCAGGGCAGAGTCACCATG ACCACAGACACATCCACGAGCACAGCCTAC ATGGAGCTGAGGAGCCTGAGATCTGACGAC |

TABLE 6-continued

VH nucleotide sequences of exemplified antibodies

| Antibody | DNA of VH |
|---|---|
| | ACGGCCGTGTATTACTGTGCGAGAGATCTC GGCTGGCCAGATGACTACTGGGGCCAGGGA ACCCTGGTCACCGTCTCCTCA (SEQ ID NO. 47) |
| TE01 | GAAGTGCAGTTGTTGGAGTCTGGGGGAGGT GTGGTACGGCCTGGGGGGTCCCTGAGACTC TCCTGTGCAGCCTCTGGATTCACCTTTGAT GATTATGGCATGAGCTGGGTCCGCCAAGCT CCAGGGAAGGGGCTGGAGTGGGTCTCTGGT ATTAATTGGAATGGTGGTAGCACAGGTTAT GCAGAGCTCCGTGAAGGGCCGATTCACCATC TCCAGAGACAATTCCAAGAACACGCTGTAT CTGCAAATGAACAGCCTGAGAGCTGAGGAC ACGGCTGCGTATTACTGTGCGAAAGATCGA CTAAGATATTGTAGTAGTACCAGCTGCTAT ATCCCTGACTACTGGGGCCAGGGAACCCTG GTCACCGTCTCCTCA (SEQ ID NO. 48) |
| TG02 | CAGGTGCAGCTGGTGCAGTCTGGAGCTGAG GTGAAGAAGCCTGGGGCCTCAGTGAAGGTC TCCTGCAAGGCTTCTGGTTACACCTTTACC AGCTATGGTATCAGCTGGGTGCGACAGGCC CCTGGACAAGGGCTTGAGTGGATGGGATGG ATCAGCGCTTACAATGGTAACACAAACTAT GCACAGAAGCTCCAGGGCAGAGTCACCATG ACCACAGACACATCCACGAGCACAGCCTAC ATGGAGCTGAGGAGCCTGAGATCTGACGAC ACGGCCGTGTATTACTGTGCGAGAGTAGGG AGCACTTACGATTTTTGGAGTGGCGCCTAC TACTACTACGGTATGGACGTCTGGGGCCAA GGGACCACGGTCACCGTCTCCTCA (SEQ ID NO. 49) |

TABLE 7

VL nucleotide sequences of exemplified antibodies

| Antibody | DNA of VL |
|---|---|
| TA02 | GACATCCAGATGACCCAGTCTCCATCCTCC CTGTCTGCATCTGTAGGAGACAGAGTCACC ATCACTTGCCAGGCGAGTCAGGACATTAGC AACTACTTAAATTGGTATCAGCAGAAACCA GGGAAAGCCCCTAAGCTCCTGATCTATGCT GCATCCAGTTTGCAAAGTGGGGTCCCATCA AGGTTCAGTGGCAGTGGATCTGGGACAGAT TTCACTCTCACCATCAGCAGTCTGCAACCT GAAGATTTTGCAACTTACTACTGTCAACAG AGTTACAGTACCCCTACTTTTGGCCAGGGG ACCAAGCTGGAGATCAAA (SEQ ID NO. 50) |
| TC01 | CAGGCAGTGCTGACTCAGCCACCCTCAGTG TCCGTGTCCCCAGGACAGACAGCCAGCATC ACCTGCTCTGGAGATAAATTGGGAAATAAA AATGCTTATTGGTATCAGCAGAAGCCAGGC CAGTCCCCTGTACTGGTCATGTATCAAAGT ACCAGACGGCCCTCAGGGATCCCTGAGCGA TTCTCTGCCTCCAACTCTGGGAACACAGCC ACTCTGACCATCAGCGGGACCCAGGCTATG GATGAGGCTGACTATTACTGTCAGGCGTGG GACAGCAGTAGTGGATGGGAGGTATTCGGC GGAGGGACCAAGCTGACCGTCCTA (SEQ ID NO. 51) |
| TC02 | GAAACGACACTCACGCAGTCTCCAGCCACC CTGTCTTTGTCTCCAGGGGAAAGAGCCACC CTCTCCTGCGGGGCCAGTCAGAGTGTTAGC AGCAGCTACTTAGCCTGGTACCAGCAGAAA CCTGGCCTGGCGCCCAGGCTCCTCATCTAT GATGCATCCAGCAGGGCCACTGGCATCCCA GACAGGTTCAGTGGCAGTGGGTCTGGGACA GACTTCACTCTCACCATCAGCAGACTGGAG CCTGAAGATTTTGCAGTTTATTACTGTCAC CAGTATAATAACTGGCCTAGGACGTTCGGC CAAGGGACCAAGGTGGAAATCAAA (SEQ ID NO. 52) |
| TD01 | CAGCCTGTGCTGACTCAGCCACCCTCAGCG TCTGGGACCCCCGGGCAGAGGGTCACCATC TCTTGTTCTGGAAGCAGCTCCAACATCGGA AGTAATTATGTATACTGGTACCAGCAGCTC CCAGGAACGGCCCCCAAACTCCTCATCTAT AGGAATAATCAGCGGCCCTCAGGGGTCCCT GACCGATTCTCTGGCTCCAAGTCTGGCACC TCAGCCTCCCTGGCCATCAGTGGGCTCCGG TCCGAGGATGAGGCTGATTATTATTGTGCA GCATGGGATGACAGCCTGAATGGTGTGGTA TTCGGCGGAGGGACCAAGCTGACCGTCCTA (SEQ ID NO. 53) |
| TE01 | GACATCCAGATGACCCAGTCTCCGGACTCC CTGGCTGTGTCTCTGGGCGAGAGGGCCACC ATCAACTGCAAGTCCAGCCAGAGTGTTTTG GACAGCTCCAACAATAAAAATTATGTCGCT TGGTTCCAGCAGAAACCAGGACAGCCTCCT AAGCTGCTCATTTACTGGGCCTCTACCCGG GAATCCGGGGTCCCTGACCGATTCAGTGGC AGCGGTTCTGGGACAGATTTCACTCTCACC ATCAGCAGCCTGCAGGCTGAAGATGTGGCA GTTTATTACTGTCAGCAATATTATACTACT CGGTGGACGTTCGGCCAAGGGACCAAGGTG GAAATCAAA (SEQ ID NO. 54) |
| TG02 | GACATCGTGATGACCCAGTCTCCATCCTCC CTGTCTGCATCTGTAGGAGACAGAGTCACC ATCACTTGCCGGGCAAGTCAGGGCATTAGA AATGATTAGGCTGGTATCAGCAAAAACCA GGGAAAGCCCCTAAACTCCTGATCTACGAT GCATCCAATTTGGAAACAGGGGTCCCATCA AGGTTCAGTGGAAGTGGATCTGGGACAGAT TTTACTTTCACCATCAGCAGCCTGCAGCCT GAAGATATTGCAACATATTACTGTCAACAG TATGATAACCTCCCGCTCACTTTCGGCGGA GGGACCAAGGTGGAGATCAAA (SEQ ID NO. 55) |

The sequences of the 8 novel anti-TMEM antibodies hybridoma-based are reported in Tables 8-13 below.

TABLE 8

VH CDR Sequences of exemplified antibodies

| Antibody | CDR1 | CDR2 | CDR3 |
|---|---|---|---|
| TE02.1 | GFTFSRHG (SEQ ID NO. 56) | IWYDGRNK (SEQ ID NO. 57) | AREGITMVRGVIPLFDY (SEQ ID NO. 58) |
| TE02.2 | GFTFSRHG (SEQ ID NO. 56) | IWYDGRNK (SEQ ID NO. 57) | AREGITMVRGVIPLFDY (SEQ ID NO. 58) |
| TE02.3 | GFTFSRHG (SEQ ID NO. 56) | IWYDGRNK (SEQ ID NO. 57) | AREGITMVRGVIPLFDY (SEQ ID NO. 58) |
| TE03 | GFTFSRYG (SEQ ID NO. 59) | IWYDGSYK (SEQ ID NO. 60) | ARFGILTGYYFDY (SEQ ID NO. 61) |

TABLE 8-continued

VH CDR Sequences of exemplified antibodies

| Antibody | CDR1 | CDR2 | CDR3 |
| --- | --- | --- | --- |
| TE04 | GFTFSRHG (SEQ ID NO. 56) | IWYDGRNK (SEQ ID NO. 57) | AREGITMVRGVIPLFDY (SEQ ID NO. 58) |
| TE07 | GFTFSSYA (SEQ ID NO. 62) | ISGSGYST (SEQ ID NO. 63) | AKGKVGPTYAFDL (SEQ ID NO. 64) |
| TE10 | GFTFSSYG (SEQ ID NO. 65) | IWYDGSNK (SEQ ID NO. 66) | AREGRGMDV (SEQ ID NO. 67) |
| TM1 | GFTFSTYG (SEQ ID NO. 68) | IWYDGYNK (SEQ ID NO. 69) | EGWFGKLLSALDI (SEQ ID NO. 70) |

TABLE 9

VL CDR sequences of exemplified antibodies

| Antibody | CDR1 | CDR2 | CDR3 |
| --- | --- | --- | --- |
| TE02.1 | SGHSSYA (SEQ ID NO. 71) | LNSDGSH (SEQ ID NO. 72) | QTWGTGMLC (SEQ ID NO. 73) |
| TE02.2 | SGHSSYA (SEQ ID NO. 71) | LNSDGSH (SEQ ID NO. 72) | QTWGTGMLF (SEQ ID NO. 74) |
| TE02.3 | SGHSSYA (SEQ ID NO. 71) | LNSDGSH (SEQ ID NO. 72) | QTWGTGMLW (SEQ ID NO. 75) |
| TE03 | SGHSSYA (SEQ ID NO. 71) | LNSDGSH (SEQ ID NO. 72) | QTWGTGCC (SEQ ID NO. 76) |
| TE04 | SGSVSTSYN (SEQ ID NO. 77) | STN (SEQ ID NO. 78) | VLYMGSGII (SEQ ID NO. 79) |
| TE07 | SGSVSTSYY (SEQ ID NO. 80) | STN (SEQ ID NO. 78) | VLYMGSGTCC (SEQ ID NO. 81) |
| TE10 | SGHSSYI (SEQ ID NO. 82) | LEGSGSY (SEQ ID NO. 83) | ETWDSNTPHAV (SEQ ID NO. 84) |
| TM1 | QGIRND (SEQ ID NO. 85) | PAS (SEQ ID NO. 86) | LQDYNYPFT (SEQ ID NO. 87) |

TABLE 10

VH amino acid sequences of exemplified antibodies

| Antibody | AA of VH |
| --- | --- |
| TE02.1 | QVQLVESGGGVVQPGRSLRLSCAASGFTFSRHGMHWVRQAPGKGLEWVAVIWYDGRNKYYADSVKGRFTISRDNSKNTLYLQMNSLRVEDTAVYYCAREGITMVRGVIPLFDYWGQGTLVTVSS (SEQ ID NO. 88) |
| TE02.2 | QVQLVESGGGVVQPGRSLRLSCAASGFTFSRHGMHWVRQAPGKGLEWVAVIWYDGRNKYYADSVKGRFTISRDNSKNTLYLQMNSLRVEDTAVYYCAREGITMVRGVIPLFDYWGQGTLVTVSS (SEQ ID NO. 89) |
| TE02.3 | QVQLVESGGGVVQPGRSLRLSCAASGFTFSRHGMHWVRQAPGKGLEWVAVIWYDGRNKYYADSVKGRFTISRDNSKNTLYLQMNSLRVEDTAVYYCAREGITMVRGVIPLFDYWGQGTLVTVSS (SEQ ID NO. 90) |
| TE03 | QVQLVESGGGVVQPGRSLRLSCAASGFTFSRYGMHWVRQAPGKGLEWVAVIWYDGSYKYYADSIKGRFTVSRDNSKNTLYLQMNSLRAEDTALYYCARFGILTGYYFDYWGQGTLVTVSS (SEQ ID NO. 91) |
| TE04 | QVQLVESGGGVVQPGRSLRLSCAASGFTFSRHGMHWVRQAPGKGLEWVAVIWYDGRNKYYADSVKGRFTISRDNSKNTLYLQMNSLRVEDTAVYYCAREGITMVRGVIPLFDYWGQGTLVTVSS (SEQ ID NO. 92) |
| TE07 | EVQLLESGGGLVQPGGSLRLSCAASGFTFSSYAMSWVRQAPGEGLEWVSGISGSGYSTYSADSVKGRFTIFKDNSKNTLYLQINSLRAEDTAVYYCAKGKVGPTYAFDLWGQGTMVTVSS (SEQ ID NO. 93) |
| TE10 | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCAREGRGMDVWGQGTTVTVSS (SEQ ID NO. 94) |
| TM1 | QVQLVESGGGVVQPGRSLRLSCAASGFTFSTYGIHWVRQAPGKGLEWVAVIWYDGYNKYYVDSVKGRFTISRDNSENTVYLQMNSLRTEDTAVYYCAREGWFGKLLSALDIWGQGTMVTVSS (SEQ ID NO. 95) |

TABLE 11

VL amino acid sequences of exemplified antibodies

| Antibody | AA of VK |
| --- | --- |
| TE02.1 | QFVLTQSPSASASLGASVKLTCTLSSGHSSYAIAWHHQQPEKGPRYLMKLNSDGSHSKGDGIPDRFSGSSSGAERYLTISSLQSEDEADYYCQTWGTGMLCFGGGTQLTALR (SEQ ID NO. 96) |
| TE02.2 | QFVLTQSPSASASLGASVKLTCTLSSGHSSYAIAWHHQQPEKGPRYLMKLNSDGSHSKGDGIPDRFSGSSSGAERYLTISSLQSEDEADYYCQTWGTGMLFGGGTQLTALR (SEQ ID NO. 97) |
| TE02.3 | QFVLTQSPSASASLGASVKLTCTLSSGHSSYAIAWHHQQPEKGPRYLMKLNSDGSHSKGDGIPDRFSGSSSGAERYLTISSLQSEDEADYYCQTWGTGMLWFGGGTQLTALR (SEQ ID NO. 98) |
| TE03 | QVVLTQSPPASASLGASVKLTCTLSSGHSSYAIAWHQQQPEKGPRYLMKLNSDGSHSKGDGIPDRFSGSSSGAERYLTISSLQSEDEADYYCQTWGTGCCFGGGTQLTALR (SEQ ID NO. 99) |

TABLE 11-continued

VL amino acid sequences of exemplified antibodies

| Antibody | AA of VK |
|---|---|
| TE04 | QTVVTQESSFSVSPGGTVTLTCGLSSGS VSTSYNPSWYQQTPGQAPRTLIYSTNTR SSGVPDRFSGSILGNKAALTITGAQADD ESDYYCVLYMGSGIIFGSGTKVTVL (SEQ ID NO. 100) |
| TE07 | QTVVTQEPSFSVSPGGTVTLTCGLSSGS VSTSYYPSWYQQTPGQAPRTLIYSTNTR SSGVPERFSGSILGNKAALTITGAQADD ESDYYCVLYMGSGTCCFGGGTQLTALR (SEQ ID NO. 101) |
| TE10 | QPVLTQSSSASASLGSSVKLTCTLSSGH SSYIIAWHQQQPGKAPRYLMKLEGSGSY NKGSGVPDRFSGSSSGADRYLTISNLQF EDEADYYCETWDSNTPHAVFGGGTQLT AL (SEQ ID NO. 102) |
| TM1 | VIQMTQSPSSLSASVGDRVTITCRASQG IRNDLGWYLQKPGKAPELLIYPASSLQS GVPSRFSGSGSGTDFTLTISSLQPEDFA TYYCLQDYNYPFTFGQGTKLEIK (SEQ ID NO. 103) |

TABLE 12

VH nucleotide sequences of exemplified antibodies

| Antibody | DNA of VH |
|---|---|
| TE02.1 | CAGGTCCAACTCGTCGAGAGCGGAGGAGGA GTCGTCCAACCCGGAAGGAGCTTGCGGCTA TCATGCGCGGCATCCGGCTTCACATTTTCC CGGCACGGGATGCACTGGGTCAGGCAAGCA CCCGGCAAGGGGCTAGAATGGGTCGCGGTC ATCTGGTATGATGGAAGGAACAAATACTAT GCCGACTCAGTCAAGGGGCGATTTACAATT TCGCGAGACAACTCCAAGAATACGCTATAC CTGCAAATGAACTCGCTGAGGGTCGAGGAC ACGGCGGTTTATTACTGCGCGAGGGAGGGG ATAACTATGGTCAGAGGAGTCATTCCGCTA TTTGACTATTGGGGCAGGGTACCTTAGTC ACGGTCTCGAGC (SEQ ID NO. 104) |
| TE02.2 | CAGGTCCAACTCGTCGAGAGCGGAGGAGGA GTCGTCCAACCCGGAAGGAGCTTGCGGCTA TCATGCGCGGCATCCGGCTTCACATTTTCC CGGCACGGGATGCACTGGGTCAGGCAAGCA CCCGGCAAGGGGCTAGAATGGGTCGCGGTC ATCTGGTATGATGGAAGGAACAAATACTAT GCCGACTCAGTCAAGGGGCGATTTACAATT TCGCGAGACAACTCCAAGAATACGCTATAC CTGCAAATGAACTCGCTGAGGGTCGAGGAC ACGGCGGTTTATTACTGCGCGAGGGAGGGG ATAACTATGGTCAGAGGAGTCATTCCGCTA TTTGACTATTGGGGCAGGGTACCTTAGTC ACGGTCTCGAGC (SEQ ID NO. 105) |
| TE02.3 | CAGGTCCAACTCGTCGAGAGCGGAGGAGGA GTCGTCCAACCCGGAAGGAGCTTGCGGCTA TCATGCGCGGCATCCGGCTTCACATTTTCC CGGCACGGGATGCACTGGGTCAGGCAAGCA CCCGGCAAGGGGCTAGAATGGGTCGCGGTC ATCTGGTATGATGGAAGGAACAAATACTAT GCCGACTCAGTCAAGGGGCGATTTACAATT TCGCGAGACAACTCCAAGAATACGCTATAC CTGCAAATGAACTCGCTGAGGGTCGAGGAC |

TABLE 12-continued

VH nucleotide sequences of exemplified antibodies

| Antibody | DNA of VH |
|---|---|
| | ACGGCGGTTTATTACTGCGCGAGGGAGGGG ATAACTATGGTCAGAGGAGTCATTCCGCTA TTTGACTATTGGGGGCAGGGTACCTTAGTC ACGGTCTCGAGC (SEQ ID NO. 106) |
| TE03 | CAGGTCCAACTCGTTGAATCCGGGGGGGGA GTCGTCCAACCGGGGAGAAGCCTGCGGCTA AGCTGCGCGGCTTCGGGATTCACATTCTCT CGATACGGGATGCACTGGGTCAGGCAAGCA CCCGGGGAAGGGCTTGGAATGGGTCGCCGTC ATATGGTACGACGGATCATATAAATATTAT GCTGACTCTATAAAGGGGCGATTCACGGTT AGCCGAGACAACTCCAAAAACACGCTATAC CTGCAAATGAACTCACTGCGAGCTGAAGAT ACGGCGCTATATTATTGCGCCCGATTCGGA ATCCTGACCGGATATTATTTTGACTACTGG GGGCAGGGTACCCTAGTCACGGTCTCGAGC (SEQ ID NO. 107) |
| TE04 | CAGGTCCAACTCGTCGAGAGCGGAGGAGGA GTCGTCCAACCCGGAAGGAGCTTGCGGCTA TCATGCGCGGCATCCGGCTTCACATTTTCC CGGCACGGGATGCACTGGGTCAGGCAAGCA CCCGGCAAGGGGCTAGAATGGGTCGCGGTC ATCTGGTATGATGGAAGGAACAAATACTAT GCCGACTCAGTCAAGGGGCGATTTACAATT TCGCGAGACAACTCCAAGAATACGCTATAC CTGCAAATGAACTCGCTGAGGGTCGAGGAC ACGGCGGTTTATTACTGCGCGAGGGAGGGG ATAACTATGGTCAGAGGAGTCATTCCGCTA TTTGACTATTGGGGGCAGGGTACCTTAGTC ACGGTCTCGAGC (SEQ ID NO. 108) |
| TE07 | GAAGTCCAACTGCTGGAATCGGGCGGGGGG CTGGTCCAACCCGGAGGATCATTGAGGCTG TCATGCGCCGCTTCCGGCTTTACATTTAGC TCATACGCAATGCATGGGTCCGACAAGCT CCGGGGGAGGGACTGGAATGGGTCTCTGGG ATTTCGGGCTCTGGATACTCCACATATAGC GCGGACTCAGTCAAGGGGAGATTCACGATT TTTAAGGATAACTCCAAGAATACATTATAT CTGCAAATAAACTCGCTGAGGGCGAGGAT ACCGCCGTTTATTACTGCGCCAAAGGGAAA GTCGGGCCAACTTACGCATTCGACCTATGG GGGCAGGGTACCATGGTCACGGTCTCGAGC (SEQ ID NO. 109) |
| TE10 | CAAGTGCAACTCGTGGAATCGGGCGGAGGG GTGGTGCAACCGGGAAGATCACTGCGACTA TCATGCGCCGCATCGGGATTTACATTTAGC AGCTACGGGATGCACTGGGTCCGCCAAGCA CCCGGAAAGGGCTGGAATGGGTCGCGGTG ATTTGGTACGATGGCTGAATAAATACTAT GCTGACTCGGTGAAGGGCCGATTCACAATC TCGCGGGACAACTCCAAAAACACACTATAT CTGCAAATGAACTCACTGCGGGCGGAGGAT ACCGCGGTATATTACTGCGCGAGGGAGGGG CGCGGAATGGATGTATGGGGGCAGGGTACC ACGGTGACCGTCTCGAGC (SEQ ID NO. 110) |
| TM1 | CAGGTGCAGCTGGTGGAGTCTGGGGGAGGC GTGGTCCAGCCTGGGAGGTCCCTGAGACTC TCCTGTGCAGCATCTGGATTCACCTTCAGT ACCTATGGCATATACACTGGGTCGCCAGGCT CCAGGCAAGGGGCTGGAGTGGGTGGCAGTT ATATGGTATGATGGATATAATAAATACTAT GTAGACTCCGTGAAGGGCCGATTCACCATC TCCAGAGACAATTCCGAGAACACGGTGTAT CTGCAGATGAACAGCCTGAGAACCGAGGAC ACGGCTGTTTATTACTGTGCGAGAGAAGGA |

TABLE 12-continued

VH nucleotide sequences of exemplified antibodies

| Antibody | DNA of VH |
|---|---|
| | TGGTTCGGGAAATTATTATCCGCTCTTGAT<br>ATCTGGGGCCAAGGGACAATGGTCACCGTC<br>TCTTCA<br>(SEQ ID NO. 111) |

TABLE 13

VL nucleotide sequences of exemplified antibodies

| Antibody | DNA of VL |
|---|---|
| TE02.1 | GCGGCCGCCATGAATTTTGGACTGAGGCTGATTTTCCTGGTGCTGACCCTGAAAG<br>GCGTCCAGTGTCAATTTGTGCTGACGCAATCGCCATCGGCTAGTGCATCACTGGG<br>GGCGAGCGTTAAATTGACATGCACGCTATCGAGCGGACACTCATCATATGCCATT<br>GCATGGCACCACCAACAACCGGAAAAGGGGCCACGATATCTAATGAAGCTGAACT<br>CTGACGGATCGCATTCGAAAGGGGATGGGATTCCCGACCGATTCTCGGGAAGCA<br>GCAGCGGAGCTGAAAGATATTTAACGATATCATCGCTGCAATCGGAGGATGAAGC<br>TGACTACTACTGCCAAACTTGGGGAACGGGGATGCTATGCTTCGGAGGAGGCAC<br>ACAATTGACGGCCCTTGGACAACCG (SEQ ID NO. 112) |
| TE02.2 | GCGGCCGCCATGAATTTTGGACTGAGGCTGATTTTCCTGGTGCTGACCCTGAAAG<br>GCGTCCAGTGTCAATTTGTACTGACGCAAAGCCCAAGCGCGAGCGCATCGCTGG<br>GAGCATCCGTCAAGCTCACATGCACGCTATCATCGGGCCATTCAAGCTATGCCAT<br>AGCATGGCATCACCAACAACCGGAGAAGGGACCTCGATATCTGATGAAGCTGAAT<br>AGCGACGGCTCCCACTCAAAGGGGGACGGAATCCCGGATAGATTTTCGGGCTCA<br>TCAAGCGGAGCGGAGCGATATCTCACGATCTCTAGCCTGCAAAGCGAGGATGAG<br>GCCGACTACTACTGCCAAACATGGGGGACGGGAATGCTATTCGGAGGAGGCACG<br>CAACTGACGGCGCTGGGGCAACCA (SEQ ID NO. 113) |
| TE02.3 | GCGGCCGCCATGAATTTTGGACTGAGGCTGATTTTCCTGGTGCTGACCCTGAAAG<br>GCGTCCAGTGTCAATTTGTGCTGACGCAATCACCATCGGCTTCGGCGAGCCTGG<br>GGGCATCTGTCAAGCTGACATGCACGCTGAGCTCCGGGCATTCATCATATGCCAT<br>CGCATGGCATCACCAACAACCCGAGAAGGGACCACGATATCTCATGAAGCTAAAC<br>TCCGACGGATCGCATTCGAAGGGGATGGAATACCCGACCGATTTTCGGGATCA<br>TCGAGCGGGGCGGAGAGATATTTGACGATCTCCTCTCTGCAAAGCGAGGACGAG<br>GCGGACTACTATTGCCAAACCTGGGGCACGGGAATGCTATGGTTTGGAGGAGGC<br>ACACAACTGACGGCGCTGGGCCAACCG (SEQ ID NO. 114) |
| TE03 | GCGGCCGCCATGAATTTTGGACTGAGGCTGATTTTCCTGGTGCTGACCCTGAAAG<br>GCGTCCAGTGTCAAGTAGTCCTGACTCAAAGCCCCCCGGCGAGCGCATCATTGG<br>GGGCGAGCGTCAAGCTGACATGCACGCTATCGAGCGGGCACTCTAGCTACGCGA<br>TAGCATGGCACCAACAACAACCGGAAAAGGGACCCCGATACTTGATGAAATTAAA<br>TAGCGACGGATCGCACTCTAAGGGAGACGGAATACCTGATAGATTTAGCGGGAG<br>CTCATCGGGGGCGGAGAGATACTTGACGATTAGCTCACTGCAATCGGAGGATGA<br>GGCGGACTACTATTGCCAAACATGGGGGACGGGATGCTGCTTCGGAGGAGGCAC<br>GCAACTGACCGCATTGGGACAACCA (SEQ ID NO. 115) |
| TE04 | GCGGCCGCCATGAATTTTGGACTGAGGCTGATTTTCCTGGTGCTGACCCTGAAAG<br>GCGTCCAGTGTCAAACCGTGGTGACACAAGAATCAAGTTTTAGCGTATCGCCGGG<br>AGGGACGGTGACGCTGACCTGCGGGCTATCATCTGGATCGGTATCAACATCCTA<br>CAATCCGAGCTGGTATCAACAAACGCCCGGACAAGCGCCACGAACCCTGATATAT<br>TCGACAAATACCCGATCATCTGGGGTGCCGGATAGATTTTCCGGCTCGATTCTGG<br>GAAACAAGGCTGCGCTGACGATAACCGGAGCTCAAGCCGACGATGAGAGCGATT<br>ATTATTGCGTGCTATACATGGGGAGCGGGATTATATTCGGATCTGGAACGAAAGT<br>CACGGTGCTAGGACAACCG (SEQ ID NO. 116) |
| TE07 | GCGGCCGCCATGAATTTTGGACTGAGGCTGATTTTCCTGGTGCTGACCCTGAAAG<br>GCGTCCAGTGTCAAACGGTCGTCACGCAAGAGCCATCCTTCTCGGTCTCGCCGG<br>GGGGGACGGTCACACTGACATGCGGGCTGAGCTCGGGATCGGTCTCAACGAGC<br>TACTACCCGAGCTGGTATCAACAAACACCGGGGCAAGCACCGCGGACGCTGATA<br>TATTCCACAAATACACGGAGCTCCGGTGTCCCGGAGAGATTCTCGGGATCAATAC<br>TGGGGAACAAGGCGGCTCTGACGATAACCGGAGCCCAAGCGGATGACGAATCG<br>GACTATTACTGCGTCCTATACATGGGCTCCGGCACATGCTGCTTTGGAGGAGGCA<br>CACAACTGACGGCGCTGGGACAACCT (SEQ ID NO. 117) |
| TE10 | GCGGCCGCCATGAATTTTGGACTGAGGCTGATTTTCCTGGTGCTGACCCTGAAAG<br>GCGTCCAGTGTCAGCCGGTTTTGACGCAATCTAGCAGCGCATCCGCTAGTCTTGG<br>AAGCTCCGTGAAGCTGACATGCACACTATCATCGGGGCATTCCTCCTACATAATT<br>GCATGGCATCAACAACAACCCGGCAAGGCCCCGAGATACTTAATGAAACTGAAG<br>GATCGGGATCATATAACAAAGGATCGGGGGTGCCGGATAGATTTAGCGGATCTAG |

TABLE 13-continued

VL nucleotide sequences of exemplified antibodies

| Antibody | DNA of VL |
| --- | --- |
|  | CTCTGGGGCTGACCGATACCTGACGATCTCTAATCTGCAATTTGAGGACGAGGCC<br>GATTACTACTGCGAAACATGGGATAGCAACACCCCACACGCGGTATTTGGAGGAG<br>GCACCCAATTGACCGCGCTAGGCCAACCA (SEQ ID NO. 118) |
| TM1 | GTCATCCAGATGACCCAGTCTCCATCCTCCCTGTCTGCATCTGTAGGAGACAGAG<br>TCACCATCACTTGCCGGGCAAGTCAGGGCATTAGAAATGATTTAGGCTGGTATCT<br>GCAGAAACCAGGGAAAGCCCCTGAGCTCCTGATCTATCCTGCATCCAGTTTACAA<br>AGTGGGGTCCCGTCAAGGTTCAGCGGCAGTGGATCTGGCACAGATTTCACTCTCA<br>CCATCAGCAGCCTGCAGCCTGAAGATTTTGCAACTTATTACTGTCTACAAGATTA<br>CAATTACCCGTTCACTTTTGGCCAGGGGACCAAGCTGGAGATCAAA<br>(SEQ ID NO. 119) |

Further Antibodies

IgG Production

Amino acid sequences were reverse translated into DNA and codon optimized for HEK expression. The optimized DNA sequences were chemically synthesized and cloned into a human SgG4 (S228P L235E mutant) expression vector. Transfection-grade DNA was prepared and used for the transient transfection of HEK cells. Produced antibodies were purified from the HEK culture supernatant by affinity chromatography (Protein A). The protein concentration was determined by UV/VIS spectrometry and purity was checked by reducing SDS-PAGE analysis.

TABLE 14

VH CDR Sequences of exemplified antibodies

| Antibody | CDR1 | CDR2 | CDR3 |
| --- | --- | --- | --- |
| TC03 | SYGI<br>(SEQ ID<br>NO. 4) | WISAYNGNT<br>NYAQKLQG<br>(SEQ ID<br>NO. 5) | WGRWL<br>AHDY<br>(SEQ ID<br>NO. 6) |
| TC04 | SYGI<br>(SEQ ID<br>NO. 4) | WISAYNGNT<br>NYAQKLQG<br>(SEQ ID<br>NO. 5) | WGRWL<br>AHDY<br>(SEQ ID<br>NO. 6) |
| TC05 | SYGI<br>(SEQ ID<br>NO. 4) | WISAYNGNT<br>NYAQKLQG<br>(SEQ ID<br>NO. 5) | WGRWL<br>AHDY<br>(SEQ ID<br>NO. 6) |

TABLE 15

VL CDR Sequences of exemplified antibodies

| Antibody | CDR1 | CDR2 | CDR3 |
| --- | --- | --- | --- |
| TC03 | SGDKLGNKNAY<br>(SEQ ID<br>NO. 17) | QSTRRPS<br>(SEQ ID<br>NO. 18) | QAWLSSSGWEV<br>(SEQ ID<br>NO. 166) |
| TC04 | SGDKLGNKNAY<br>(SEQ ID<br>NO. 17) | QSTRRPS<br>(SEQ ID<br>NO. 18) | QAWDSSSGWEV<br>(SEQ ID<br>NO. 167) |
| TC05 | SGDKLGNKNAY<br>(SEQ ID<br>NO. 17) | QSTRRPS<br>(SEQ ID<br>NO. 18) | QAWDSSSGWEV<br>(SEQ ID<br>NO. 19) |

TABLE 16

VH amino acid sequences of exemplified antibodies

| Antibody | AA of VH |
| --- | --- |
| TC03 | QIQLVQSGAEVKQPGASVSVSCAASGYTFTSYG<br>ISWVRQAPGQGLEWMGWISAYNGNTNYAQKLQG<br>RVTMTTDTSTSTAYMELSSLRSDDTAVYYCAR<br>WGRWLAHDYWGQGTLVTVSS<br>(SEQ ID NO. 168) |
| TC04 | QIQLVQSGAEVKQPGASVSVSCAASGYTFTSYG<br>ISWVRQAPGQGLEWMGWISAYNGNTNYAQKLQG<br>RVTMTTDTSTSTAYMELSSLRSDDTAVYYCAR<br>WGRWLAHDYWGQGTLVTVSS<br>(SEQ ID NO. 169) |
| TC05 | QIQLVQSGAEVKQPGASVSVSCAASGYTFTSYG<br>ISWVRQAPGQGLEWMGWISAYNGNTNYAQKLQG<br>RVTMTTDTSTSTAYMELSSLRSDDTA<br>VYYCARWGRWLAHDYWGQGTLVTVSS<br>(SEQ ID NO. 170) |

TABLE 17

VL amino acid sequences of exemplified antibodies

| Antibody | AA of VL |
| --- | --- |
| TC03 | QAVLTQPPSVSVSPGQTASITCSGD<br>KLGNKNAYWYQQKPGQSPVLVMYQS<br>TRRPSGIPERFSASNSGNTATLTIS<br>GTQAMDEADYYCQAWLSSSGWEVFG<br>GGTKLTVL<br>(SEQ ID NO. 171) |
| TC04 | QAVLTQPPSVSVSPGQTASITCSGD<br>KLGNKNAYWYQQKPGQSPVLVMYQS<br>TRRPSGIPERFSASNSGNTATLTIS<br>GTQAEDEADYYCQAWDSSSGWEVFG<br>GGTKLTVL<br>(SEQ ID NO. 172) |
| TC05 | QAVLTQPPSVSVSPGQTASITCSGD<br>KLGNKNAYWYQQKPGQSPVLVMYQS<br>TRRPSGIPERFSASNSGNTATLTIS<br>GTQAMDEADYYCQAWDSSSGWEVFG<br>GGTKLTVL<br>(SEQ ID NO. 173) |

TABLE 18

VH nucleotide sequences of exemplified antibodies

| Antibody | DNA of VH |
|---|---|
| TC03 | CAGATCCAGTTGGTGCAAAGTGGGGCTGAGGTAAAGCAGCCGGGT<br>GCAAGTGTGTCCGTAAGTTGTGCAGCCAGTGGCTACACCTTTACTA<br>GTTACGGAATTTCATGGGTGCGGCAAGCTCCCGGTCAGGGATTGG<br>AATGGATGGGATGGATTTCAGCATACAACGGGAACACAAATTACGC<br>TCAAAAATTGCAGGGTCGAGTTACCATGACTACAGACACGTCTACG<br>TCTACAGCTTACATGGAACTTTCCAGCCTGCGGTCCGACGACACCG<br>CAGTTTATTATTGCGCCCGCTGGGGGAGATGGCTCGCGCATGACT<br>ACTGGGGGCAGGGCACGCTGGTTACCGTTTCCTCAGCCTCCACCA<br>AGGGCCCATCCGTCTTCCCCCTGGCGCCCTGCTCCAGGAGCACCT<br>CCGAGAGCACAGCCGCCCTGGGCTGCCTGGTCAAGGACTACTTCC<br>CCGAACCGGTGACGGTGTCGTGGAACTCAGGCGCCCTGACCAGC<br>GGCGTGCACACCTTCCCGGCTGTCCTACAGTCCTCAGGACTCTACT<br>CCCTCAGCAGCGTGGTGACCGTGCCCTCCAGCAGCTTGGGCACGA<br>AGACCTACACCTGCAACGTAGATCACAAGCCCAGCAACACCAAGGT<br>GGACAAGAGAGTTGAGTCCAAATATGGTCCCCCATGCCCACCCTG<br>CCCAGCACCTGAGTTCGAGGGGGACCATCAGTCTTCCTGTTCCC<br>CCCAAAACCCAAGGACACTCTCATGATCTCCCGGACCCCTGAGGTC<br>ACGTGCGTGGTGGTGGACGTGAGCCAGGAAGACCCCGAGGTCCA<br>GTTCAACTGGTACGTGGATGGCGTGGAGGTGCATAATGCCAAGAC<br>AAAGCCGCGGGAGGAGCAGTTCAACAGCACGTACCGTGTGGTCAG<br>CGTCCTCACCGTCCTGCACCAGGACTGGCTGAACGGCAAGGAGTA<br>CAAGTGCAAGGTGTCCAACAAAGGCCTCCCGTCCTCCATCGAGAAA<br>ACCATCTCCAAAGCCAAAGGGCAGCCCCGAGAGCCACAGGTGTAC<br>ACCCTGCCCCCATCCCAGGAGGAGATGACCAAGAACCAGGTCAGC<br>CTGACCTGCCTGGTCAAAGGCTTCTACCCCAGCGACATCGCCGTG<br>GAGTGGGAGAGCAATGGGCAGCCGGAGAACAACTACAAGACCACG<br>CCTCCCGTGCTGGACTCCGACGGCTCCTTCTTCCTCTACAGCAGG<br>CTAACCGTGGACAAGAGCAGGTGGCAGGAGGGGAATGTCTTCTCA<br>TGCTCCGTGATGCATGAGGCTCTGCACAACCACTACACACAGAAGA<br>GTCTCTCCCTGTCTCTGGGTAAA (SEQ ID NO. 174) |
| TC04 | CAGATCCAGTTGGTGCAAAGTGGGGCTGAGGTAAAGCAGCCGGGT<br>GCAAGTGTGTCCGTAAGTTGTGCAGCCAGTGGCTACACCTTTACTA<br>GTTACGGAATTTCATGGGTGCGGCAAGCTCCCGGTCAGGGATTGG<br>AATGGATGGGATGGATTTCAGCATACAACGGGAACACAAATTACGC<br>TCAAAAATTGCAGGGTCGAGTTACCATGACTACAGACACGTCTACG<br>TCTACAGCTTACATGGAACTTTCCAGCCTGCGGTCCGACGACACCG<br>CAGTTTATTATTGCGCCCGCTGGGGGAGATGGCTCGCGCATGACT<br>ACTGGGGGCAGGGCACGCTGGTTACCGTTTCCTCAGCCTCCACCA<br>AGGGCCCATCCGTCTTCCCCCTGGCGCCCTGCTCCAGGAGCACCT<br>CCGAGAGCACAGCCGCCCTGGGCTGCCTGGTCAAGGACTACTTCC<br>CCGAACCGGTGACGGTGTCGTGGAACTCAGGCGCCCTGACCAGC<br>GGCGTGCACACCTTCCCGGCTGTCCTACAGTCCTCAGGACTCTACT<br>CCCTCAGCAGCGTGGTGACCGTGCCCTCCAGCAGCTTGGGCACGA<br>AGACCTACACCTGCAACGTAGATCACAAGCCCAGCAACACCAAGGT<br>GGACAAGAGAGTTGAGTCCAAATATGGTCCCCCATGCCCACCCTG<br>CCCAGCACCTGAGTTCGAGGGGGACCATCAGTCTTCCTGTTCCC<br>CCCAAAACCCAAGGACACTCTCATGATCTCCCGGACCCCTGAGGTC<br>ACGTGCGTGGTGGTGGACGTGAGCCAGGAAGACCCCGAGGTCCA<br>GTTCAACTGGTACGTGGATGGCGTGGAGGTGCATAATGCCAAGAC<br>AAAGCCGCGGGAGGAGCAGTTCAACAGCACGTACCGTGTGGTCAG<br>CGTCCTCACCGTCCTGCACCAGGACTGGCTGAACGGCAAGGAGTA<br>CAAGTGCAAGGTGTCCAACAAAGGCCTCCCGTCCTCCATCGAGAAA<br>ACCATCTCCAAAGCCAAAGGGCAGCCCCGAGAGCCACAGGTGTAC<br>ACCCTGCCCCCATCCCAGGAGGAGATGACCAAGAACCAGGTCAGC<br>CTGACCTGCCTGGTCAAAGGCTTCTACCCCAGCGACATCGCCGTG<br>GAGTGGGAGAGCAATGGGCAGCCGGAGAACAACTACAAGACCACG<br>CCTCCCGTGCTGGACTCCGACGGCTCCTTCTTCCTCTACAGCAGG<br>CTAACCGTGGACAAGAGCAGGTGGCAGGAGGGGAATGTCTTCTCA<br>TGCTCCGTGATGCATGAGGCTCTGCACAACCACTACACACAGAAGA<br>GTCTCTCCCTGTCTCTGGGTAAA (SEQ ID NO. 175) |
| TC05 | CAGATCCAGTTGGTGCAAAGTGGGGCTGAGGTAAAGCAGCCGGGT<br>GCAAGTGTGTCCGTAAGTTGTGCAGCCAGTGGCTACACCTTTACTA<br>GTTACGGAATTTCATGGGTGCGGCAAGCTCCCGGTCAGGGATTGG<br>AATGGATGGGATGGATTTCAGCATACAACGGGAACACAAATTACGC<br>TCAAAAATTGCAGGGTCGAGTTACCATGACTACAGACACGTCTACG<br>TCTACAGCTTACATGGAACTTTCCAGCCTGCGGTCCGACGACACCG<br>CAGTTTATTATTGCGCCCGCTGGGGGAGATGGCTCGCGCATGACT<br>ACTGGGGGCAGGGCACGCTGGTTACCGTTTCCTCAGCCTCCACCA<br>AGGGCCCATCCGTCTTCCCCCTGGCGCCCTGCTCCAGGAGCACCT<br>CCGAGAGCACAGCCGCCCTGGGCTGCCTGGTCAAGGACTACTTCC<br>CCGAACCGGTGACGGTGTCGTGGAACTCAGGCGCCCTGACCAGC<br>GGCGTGCACACCTTCCCGGCTGTCCTACAGTCCTCAGGACTCTACT<br>CCCTCAGCAGCGTGGTGACCGTGCCCTCCAGCAGCTTGGGCACGA<br>AGACCTACACCTGCAACGTAGATCACAAGCCCAGCAACACCAAGGT |

TABLE 18-continued

VH nucleotide sequences of exemplified antibodies

| Antibody | DNA of VH |
|---|---|
| | GGACAAGAGAGTTGAGTCCAAATATGGTCCCCCATGCCCACCCTG<br>CCCAGCACCTGAGTTCGAGGGGGGACCATCAGTCTTCCTGTTCCC<br>CCCAAAACCCAAGGACACTCTCATGATCTCCCGGACCCCTGAGGTC<br>ACGTGCGTGGTGGTGGACGTGAGCCAGGAAGACCCCGAGGTCCA<br>GTTCAACTGGTACGTGGATGGCGTGGAGGTGCATAATGCCAAGAC<br>AAAGCCGCGGGAGGAGCAGTTCAACAGCACGTACCGTGTGGTCAG<br>CGTCCTCACCGTCCTGCACCAGGACTGGCTGAACGGCAAGGAGTA<br>CAAGTGCAAGGTGTCCAACAAAGGCCTCCCGTCCTCCATCGAGAAA<br>ACCATCTCCAAAGCCAAAGGGCAGCCCCGAGAGCCACAGGTGTAC<br>ACCCTGCCCCCATCCCAGGAGGAGATGACCAAGAACCAGGTCAGC<br>CTGACCTGCCTGGTCAAAGGCTTCTACCCCAGCGACATCGCCGTG<br>GAGTGGGAGAGCAATGGGCAGCCGGAGAACAACTACAAGACCACG<br>CCTCCCGTGCTGGACTCCGACGGCTCCTTCTTCCTCTACAGCAGG<br>CTAACCGTGGACAAGAGCAGGTGGCAGGAGGGGAATGTCTTCTCA<br>TGCTCCGTGATGCATGAGGCTCTGCACAACCACTACACACAGAAGA<br>GTCTCTCCCTGTCTCTGGGTAAA (SEQ ID NO. 176) |

TABLE 19

VL nucleotide sequences of exemplified antibodies

| Antibody | DNA of VH |
|---|---|
| TC03 | CAGGCGGTGCTTACTCAGCCCCCAAGTGTGTCTGTTTCCCCCGGT<br>CAGACTGCGTCTATAACCTGCTCCGGGGATAAACTCGGCAACAAGA<br>ATGCGTACTGGTACCAACAGAAGCCGGGACAGAGCCCAGTCTTGG<br>TCATGTACCAATCCACCCGGAGACCTAGCGGCATTCCAGAGCGCTT<br>TAGTGCATCTAATTCTGGCAATACGGCGACGTTGACCATCAGTGGT<br>ACACAAGCGATGGACGAGGCAGATTACTACTGTCAGGCATGGCTG<br>TCATCATCCGGGTGGGAGGTGTTTGGCGGCGGAACAAAACTCACT<br>GTCCTAGGTCAGCCCAAGGCTGCACCAAGTGTCACTCTGTTCCCG<br>CCCTCCTCTGAGGAGCTTCAAGCCAACAAGGCCACACTGGTGTGT<br>CTCATAAGTGACTTCTACCCGGGAGCCGTGACAGTGGCCTGGAAG<br>GCAGATAGCAGCCCCGTCAAGGCGGGAGTGGAGACCACCACACC<br>CTCCAAACAAAGCAACAACAAGTACGCGGCCAGCAGCTATCTGAG<br>CCTGACGCCTGAGCAGTGGAAGTCCCACAGAAGCTACAGCTGCCA<br>GGTCACGCATGAAGGGAGCACCGTGGAGAAGACAGTGGCCCCTAC<br>AGAATGTTCA (SEQ ID NO. 177) |
| TC04 | CAGGCCGTCTTGACTCAACCACCCTCCGTTAGTGTCTCCCCCGGC<br>CAGACGGCGAGTATCACCTGTAGTGGTGATAAGCTGGGCAATAAG<br>AATGCTTACTGGTACCAGCAAAAACCCGGACAGAGCCCAGTGCTG<br>GTGATGTATCAGTCTACAAGACGACCTAGCGGCATCCCAGAAAGGT<br>TTTCTGCCAGCAATTCTGGCAATACGGCGACGCTGACTATTAGTGG<br>CACACAAGCAGAGGATGAGGCGGACTATTACTGCCAAGCATGGGA<br>CAGTAGTAGTGGTTGGGAAGTCTTCGGGGGCGGCACTAAGCTCAC<br>CGTCCTAGGTCAGCCCAAGGCTGCACCAAGTGTCACTCTGTTCCC<br>GCCCTCCTCTGAGGAGCTTCAAGCCAACAAGGCCACACTGGTGTG<br>TCTCATAAGTGACTTCTACCCGGGAGCCGTGACAGTGGCCTGGAA<br>GGCAGATAGCAGCCCCGTCAAGGCGGGAGTGGAGACCACCACAC<br>CCTCCAAACAAAGCAACAACAAGTACGCGGCCAGCAGCTATCTGA<br>GCCTGACGCCTGAGCAGTGGAAGTCCCACAGAAGCTACAGCTGCC<br>AGGTCACGCATGAAGGGAGCACCGTGGAGAAGACAGTGGCCCCTA<br>CAGAATGTTCA (SEQ ID NO. 178) |
| TC05 | CAAGCTGTATTGACACAACCTCCTAGTGTCAGTGTAAGCCCTGGTC<br>AAAACTGCCTCCATTACTTGCTCTGGCGACAAGCTCGGAAATAAGAA<br>CGCGTACTGGTACCAACAGAAGCCCGGACAGTCACCTGTGCTTGT<br>TATGTATCAAAGCACCAGGAGACCTTCAGGGATACCAGAAAGGTTT<br>AGTGCGTCTAATTCCGGGAATACCGCGACACTGACGATAAGCGGC<br>ACTCAGGCTATGGACGAAGCGGATTACTACTGTCAGGCATGGGATT<br>CATCATCAGGTTGGGAAGTATTCGGGGCGGTACAAAATTGACGG<br>TCCTAGGTCAGCCCAAGGCTGCACCAAGTGTCACTCTGTTCCCGC<br>CCTCCTCTGAGGAGCTTCAAGCCAACAAGGCCACACTGGTGTGTCT<br>CATAAGTGACTTCTACCCGGGAGCCGTGACAGTGGCCTGGAAGGC<br>AGATAGCAGCCCCGTCAAGGCGGGAGTGGAGACCACCACACCCTC<br>CAAACAAAGCAACAACAAGTACGCGGCCAGCAGCTATCTGAGCCT<br>GACGCCTGAGCAGTGGAAGTCCCACAGAAGCTACAGCTGCCAGGT<br>CACGCATGAAGGGAGCACCGTGGAGAAGACAGTGGCCCCTACAGA<br>ATGTTCA (SEQ ID NO. 179) |

TABLE 20

Constant region amino acid sequences

| Constant region | AA |
|---|---|
| Human IgG4 heavy chain P01861.1 | ASTKGPSVFPLAPCSRSTSESTAALGCLVKDYFPEPVTVSWNSGALTSG VHTFPAVLQSSGLYSLSSVVTVPSSSLGTKTYTCNVDHKPSNTKVDKRVE SKYGPPCPSCPAPEFLGGPSVFLFPPKPKDTLMISRTPEVTCVVVDVSQE DPEVQFNWYVDGVEVHNAKTKPREEQFNSTYRVVSVLTVLHQDWLNGK EYKCKVSNKGLPSSIEKTISKAKGQPREPQVYTLPPSQEEMTKNQVSLTC LVKGFYPSDIAVEWESNGQPENNYKTTPPVLDSDGSFFLYSRLTVDKSR WQEGNVFSCSVMHEALHNHYTQKSLSLSLGK (SEQ ID NO: 120) |
| Human IgG2 heavy chain P01859 | ASTKGPSVFPLAPCSRSTSESTAALGCLVKDYFPEPVTVSWNSGALTSG VHTFPAVLQSSGLYSLSSVVTVPSSNFGTQTYTCNVDHKPSNTKVDKTVE RKCCVECPPCPAPPVAGPSVFLFPPKPKDTLMISRTPEVTCVVVDVSHED PEVQFNWYVDGVEVHNAKTKPREEQFNSTFRVVSVLTVVHQDWLNGKE YKCKVSNKGLPAPIEKTISKTKGQPREPQVYTLPPSREEMTKNQVSLTCL VKGFYPSDISVEWESNGQPENNYKTTPPMLDSDGSFFLYSKLTVDKSRW QQGNVFSCSVMHEALHNHYTQKSLSLSPGK (SEQ ID NO. 121) |
| Human light chain, lambda 1 P0CG04 | GQPKANPTVTLFPPSSEELQANKATLVCLISDFYPGAVTVAWKADGSPVK AGVETTKPSKQSNNKYAASSYLSLTPEQWKSHRSYSCQVTHEGSTVEKT VAPTECS (SEQ ID NO. 122) |
| Human light chain, lambda 2 P0DOY2 | GQPKAAPSVTLFPPSSEELQANKATLVCLISDFYPGAVTVAWKADSSPVK AGVETTTPSKQSNNKYAASSYLSLTPEQWKSHRSYSCQVTHEGSTVEKT VAPTECS (SEQ ID NO. 123) |
| Human light chain, kappa P01834 | RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC (SEQ ID NO. 124) |

All studies were performed using the fully human IgG4 antibodies.

Example 1: Affinity Measurement

Octet BLI-Based Analysis

Antibodies possessed high affinity to the target, TMEM. The binding affinity measurements were performed using an Octet instrument (Octet BMIA), which is a Biolayer Interferometry (BLI) platform based on Biomolecular Interaction Analysis. To establish the assay, the target monoclonal antibody (30 µg/ml in PBS) was immobilized via Fc on the Anti-Mouse IgG Fc Capture (AMC) or Anti-Human IgG Fc Capture (AMC) biosensors and the interaction with the antigen, human and murine Ecto-TMEM219 (Genescript's customized protein service) at 150 nM was measured.

The affinity measurement of the anti-TMEM mAbs for the target human and murine Ecto-TMEM219 are reported in Table 21.

TABLE 21

Affinity measurement of exemplified antibodies

| Antibody | hEcto-TMEM KD (M) | mEcto-TMEM KD (M) |
|---|---|---|
| TC01 | $2 \times 10^{-8}$ | $3 \times 10^{-8}$ |
| TM1 | $<10^{-12}$ | $<10^{-12}$ |
| TE08 | $<10^{-12}$ | Not done |
| TE09 | $<10^{-12}$ | Not done |
| TE10 | $<10^{-12}$ | Not done |

Newly generated anti-TMEM mAbs show good human antigen binding affinity with KD below $2 \times 10^{-8}$ M. The antibodies also show murine cross reactivity. This data confirmed that mice can be considered a relevant animal species for testing of the monoclonal antibodies during preclinical development.

Measurement of the Antibody Binding Activity by ELISA

The binding activity of the purified IgG4 (TC03, TC04, TC05) to the recombinant ectoTMEM protein was measured by ELISA. In brief, ectoTMEM was diluted in PBS to 5 µg/ml and coated onto 96-well ELISA plates (100 µl/well) for 1 h at RT. After blocking and washing of the plates, an antibody dilution series was added to the plates and incubated for 1 h at RT. After washing of the plates, bound antibodies were detected via a secondary anti-human-Fc HRP-conjugated antibody. After another washing step, TMB reaction was performed, stopped with sulfuric acid and absorbance was measured. Based on the absorbance readings, an EC50 of the saturating antibodies was calculated.

The EC50 of the anti-TMEM mAbs for the target human Ecto-TMEM219 are reported in Table 22.

TABLE 22

EC50 of exemplified antibodies

| Antibody | hEcto-TMEM EC50 (ng/mL) |
|---|---|
| TC03 | 64.7 |
| TC04 | 89.8 |
| TC05 | 79.1 |

Example 2: Anti-TMEM mAbs Efficacy in IBD Mouse Model Following Intraperitoneal (IP) Administration The model of colitis induced by Dextran sulfate sodium (DSS) in C57BL/6J mice is a validated animal model to evaluate and also to confirm the anti-inflammatory and wound healing properties of drugs in IBD. DSS (oral administration in the drinking water) induces prominent diarrhea followed by inflammation. This model is well characterized, reliable, reproducible and accepted by regulatory authorities. [See, e.g., Eichele and Kharbanda, "Dextran sodium sulfate colitis murine model: an indispensable tool for advancing our understanding of inflammatory bowel disease pathogenesis," World J. Gastroenterol. 23(33):6016-6028 (2017)]. This study was performed in C57BL/6J mice. In this particular genetic background, mice develop acute colitis when analyzed 3 days after the last DSS administration or a chronic-like inflammation when analyzed 7 days after the last DSS administration.

The anti-inflammatory and wound healing effects were evaluated at the clinical and histological levels using a validated clinical score, the Disease Activity Index (DAI) (table 23) and a validated score for histological analysis (Table 24).

Animals

Male C57BL/6J mice were supplied by Charles River Laboratories, l'Arbresle, France. The mice were housed at 20±5° C. and provided with water and food ad libitum. All experimental protocols were performed in accredited facilities at Institut Pasteur from Lille according to governmental guidelines.

Establishment of DSS-Induced Mice Colitis Model and Treatment

Acute colitis was induced by feeding mice with 2.5% (w/v) DSS (45 kD; TDB Consultancy AB, Uppsala, Sweden, Batch number DB001-41) dissolved in drinking water for 5 days. The mice were randomly divided into five groups: control group; DSS+vehicle; DSS+Humira (adalimumab) 0.3 mg/mouse (Abbvie, 1108722), DSS+TM1 0.5 mg/mice and DSS+TC01 0.5 mg/mouse. To assess the effects of anti-TMEM mAb on DSS-induced acute colitis in C57BL/6J mice, the mice were treated daily by intraperitoneal administration with indicated dose of anti-TMEM mAbs starting 3 days before colitis induction and were performed until euthanasia occurring 7 days after the last DSS administration. The experimental timelines of the animal model are described in FIG. 1.

The therapeutic properties of the TMEM mAbs were compared to those of positive control Humira (adalimumab) which is approved for treatment of both Crohn's disease and ulcerative colitis. (Taghipour N. et al Gastroenterol Hepatol Bed Bench 2016; 9(1):45-52).

Because the DSS murine model requires that each of the antibodies—TMEM mAbs and positive control Humira—cross-react with the murine ortholog of its cognate human antigen (TMEM219 and TNFα, respectively)—relative efficacy in humans cannot be gauged.

Clinical Scoring

In all groups, mice weight, stool consistency and blood in stool were recorded daily. The disease activity index (DAI) scores were based on changes in body weight, consistency of stool, and hemoccult bleeding according to a standard scoring system. These parameters were assessed on a scale as described in the Table 23. The DAI data are presented as an average score of these parameters taken daily. Animals were sacrificed by cervical dislocation under anesthesia. At euthanasia, colons were carefully dissected, and colon weight and size were measured. The presence of Occult Blood (OB) is recorded using the hemoccult method.

TABLE 23

Parameters assessed for DAI score

| Disease Activity Index | Parameters | Scores |
|---|---|---|
| (DAI) | Weight loss | 0: no; 1: <10%; 2: ≥10% |
| (0-5) | Stool consistency | 0: regular; 1: soft; 2: diarrhea |
| | Blood occurrence | 0: absence; 1: presence |

Figure 2:
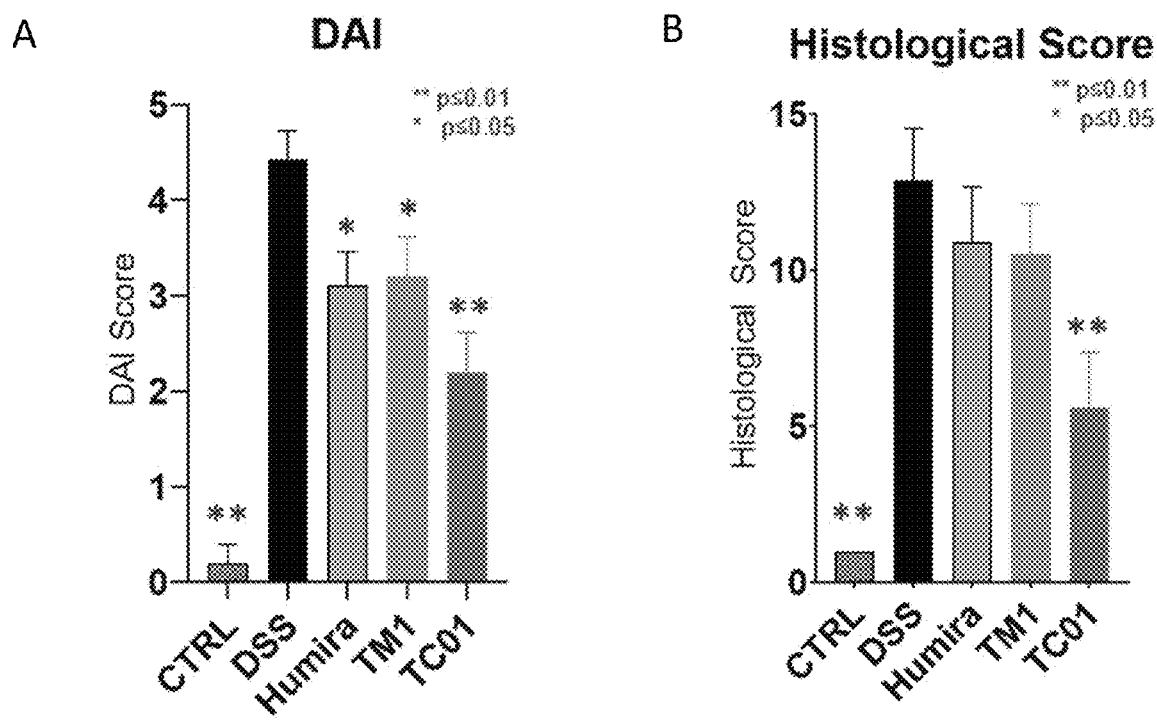
FIG. 2. (A) Disease activity index (DAI), a scoring system used to determine the severity of colitis in mice and (B) Histological Score an examination used to evaluate the severity and extent of inflammation, the intensity of cellular infiltrate in the mucosa, its extension in sub-mucosa layers, the presence of epithelial lesions and the mucosa regeneration was evaluated 7 days after the last administration of DSS during the wound healing/beginning of the chronic phase. The values are the means±SEM. *p≤0.05, **p≤0.01 vs. DSS group.

As shown on FIG. 2A, seven days after the last administration of DSS, the DAI score was significantly increased compared to healthy control group (group receiving vehicle only) in the group of DSS mice receiving the vehicle (p value=0.0012), indicating the severity of the colitis. A significant decrease in the DAI score was recorded in colitic mice receiving TCO1 (p value=0.002), TM1 (p value=0.05) and Humira (p value=0.02) compared to DSS mice receiving only the vehicle. This result indicates a strong anti-inflammatory effect of the newly generated anti-TMEM mAbs.

Assessment of Histological Colon Lesions

To assess the level of inflammation and the tissue regeneration, the colon samples were embedded in paraffin and analyzed. For the histological evaluation, sections of colonic tissues (4 m) were stained with May-Grunwald-Giemsa and evaluated. A multiparametric scoring (0 to 18), as described in Dieleman et al. 1998 (Table 24), was performed blindly by two investigators. The histological examination graded the severity and extent of inflammation, the intensity of cellular infiltrate in the mucosa, its extension in sub-mucosa layers, the presence of epithelial lesions and the tissue regeneration. Paraffin-embedded colon samples were further examined to detect apoptosis by immunofluorescence staining of deoxynucleotidyl transferase-mediated deoxyuridine triphosphate (TUNEL) using the TUNEL Assay Kit (Sigma, ref 11684795910) according to the manufacturers protocol. The TUNEL method is an effective method for measuring the DNA fragments resulting from the apoptotic activation of intracellular endonucleases. Whilst, to determine the level of cell proliferation an immunofluorescence staining of Proliferating cell nuclear antigen (PCNA) was performed using the PCNA assay kit (Novus, NB600-1331) according to the manufacturer's protocol. PCNA is a cell cycle related protein that is maximally elevated in late G1 and S-phase of proliferating cells. The sections were counterstained by nuclear staining using DAPI. The localized fluorescence was detected by fluorescence microscopy.

TABLE 24

Multiparametric scoring system for histological assessment colonic lesions

| Parameter | Score | Description |
|---|---|---|
| Severity of inflammation | 0 | None |
| | 1 | Slight |
| | 2 | Moderate |
| | 3 | Severe |
| Extent | 0 | None |
| | 1 | Mucosa |
| | 2 | Mucosa and submucosa |
| | 3 | Transmural |
| Regeneration | 4 | No tissue repair |
| | 3 | Surface epithelium not intact |
| | 2 | Regeneration with crypt depletion |
| | 1 | Almost complete regeneration |
| | 0 | Complete regeneration or normal tissue |

TABLE 24-continued

Multiparametric scoring system for
histological assessment colonic lesions

| Parameter | Score | Description |
|---|---|---|
| Crypt damage | 0 | None |
| | 1 | Basal 1/3 damaged |
| | 2 | Basal 2/3 damaged |
| | 3 | Only surface epithelium intact |
| | 4 | Entire crypt and epithelium lost |
| Percentage involvement | 1 | 1-25% |
| | 2 | 26-50% |
| | 3 | 51-75% |
| | 4 | 76-100% |

Figure 3:
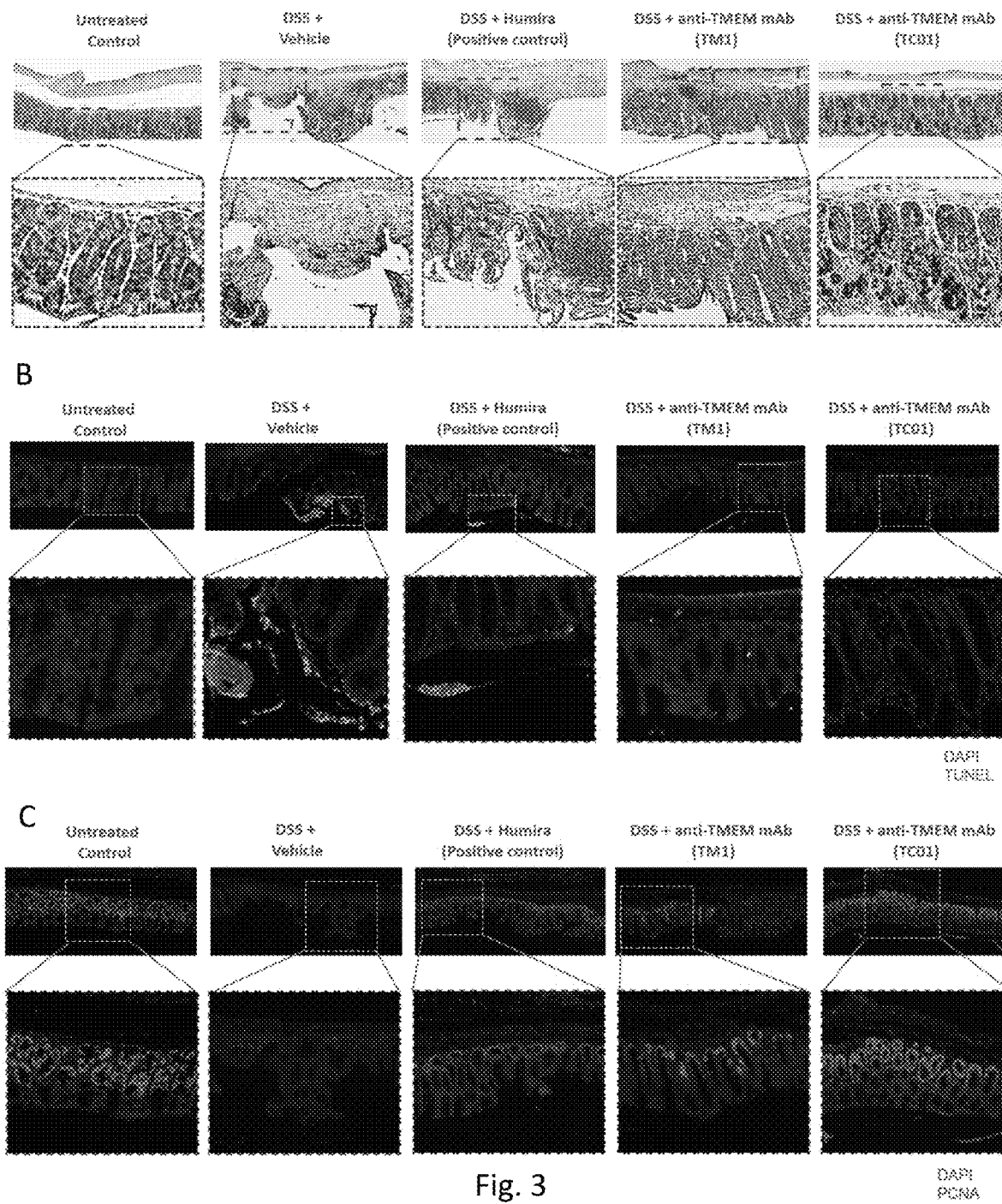
FIG. 3. Paraffin sections of colons obtained at euthanasia, i.e 7 days after the last administration of DSS, were stained with (A) May-Grunwald-Giemsa for the histological examination. (B) The apoptotic cells were detected with TUNEL assay and counterstained with DAPI. (C) Cell proliferation was detected with PCNA assay and counterstained with DAPI.

As shown on FIG. 21B, seven days after the last DSS administration, the histological score in each group was quantified from May-Grunwald-Giemsa stained sections (FIG. 3A). A sustained and significant colonic inflammation was still recorded at histological level in the groups of DSS mice receiving the vehicle compared to the healthy control group without colitis (p value=0.002). Following IP administration of TC01 at 0.5 mg/mice a significant improvement (p value=0.01) of the level of inflammation and mucosa regeneration at the histological level compared to colitic mice receiving the vehicle was observed. Besides, the IP administration of TM1 at 0.5 mg/mice showed an improvement of the level of inflammation and mucosa regeneration at the histological level compared to colitic mice receiving the vehicle.

TC01 and TM1 inhibits DSS-induced intestinal cells apoptosis in mice as shown in sections from colonic tissue stained with TUNEL staining kit, a method for detecting DNA fragmentation generated during apoptosis (FIG. 3B). The sections were counterstained with DAPI to provide nuclear staining. TUNEL positive cells in TC01 and TM1 group were lower compared to the DSS group.

The expression of PCNA was inhibited in the group of mice treated with DSS, indicating the severity of the colitis. Whilst, in the TC01 and TM1 treated group, the expression of PCNA in the colon is maintained and is comparable to the expression in the control group control that did not received DSS, as shown in sections from colonic tissue stained with PCNA staining kit (FIG. 3C).

The sections were counterstained with DAPI to provide nuclear staining.

Statistical Analysis

All comparisons were analysed using the Permutation Test for two independent samples. Statistics have been calculated using the GraphPad Prism version 7.0 (GraphPad Software, San Diego, CA). Differences were considered statistically significant if the p value was <0.05.

Example 3: Anti-TMEM mAbs Efficacy in T1D Mouse Model Following Intraperitoneal (IP) Administration Animals Female non-obese diabetic (NOD) mice (10 weeks old) were obtained from the Charles River Laboratories, Calco, Varese, Italy (stock #613). All mice were cared for and used in accordance with Italian law on animal care N° 116/1992 and the European Communities Council Directive EEC/609/86.

Diabetes Monitoring and Treatment

Overt diabetes (the most advanced stage, characterized by elevated fasting blood glucose concentration and classical symptoms) was defined as blood glucose levels above 250 mg/dL for three consecutive measurements. Glycemia was monitored twice a week. We set up the following treatment groups:
1) Untreated
2) Ecto-TMEM219 0.1 mg/day (i.p) for 10 days
3) Anti-TMEM219 TM1 0.5 mg/day (i.p) for 10 days
4) Anti-TMEM219 TC01 0.5 mg/day (i.p) for 10 days
Ecto-TMEM and antibody were dissolved in PBS.

N=10 mice were included in each group of treatment. Treatment started when mice were 10 weeks old at day 1. Mice were followed up for up to 22 weeks of age. Mice were harvested when diabetes was assessed or at week 22. Plasma samples and pancreas were collected for ex vivo analysis. The experimental timelines are described in FIG. 1.

Insulitis Scoring and Pancreatic Islet Histopathology

Insulitis scoring was performed on 5-μm-thick formalin-fixed, paraffin-embedded, hematoxylin and eosin (H&E) and Insulin stained pancreatic sections as previously described (Vergani A et al. Diabetes 2010; Ben Nasr M et al. Sci Transl Med 2017). Insulitis scoring was performed on hematoxylin and eosin (H&E)-stained pancreatic sections. A score of 0 to 4 was assigned based on islet infiltration by an experienced pathologist. Insulitis scores were graded as follows: grade 0, normal islets; grade 1, mild mononuclear infiltration (25%) at the periphery; grade 2, 25-50% of the islets infiltrated; grade 3, (50% of the islets infiltrated); grade 4, islets completely infiltrated with no residual parenchyma remaining. At least 30 islets per group were analyzed and pooled from sections obtained from different mice.

Statistical Analysis

Data are presented as mean and standard error of the mean (SEM) unless otherwise reported. The statistical significance of differences was tested with two-tailed t-test (Mann-Whitney test). Diabetes incidence among different groups was analyzed with the log-rank (Mantel-Cox) test. Statistical analysis was conducted using GraphPad Prism version 7.0 (GraphPad Software, La Jolla, CA). All statistical tests were performed at the 5% significance level.

Figure 4:
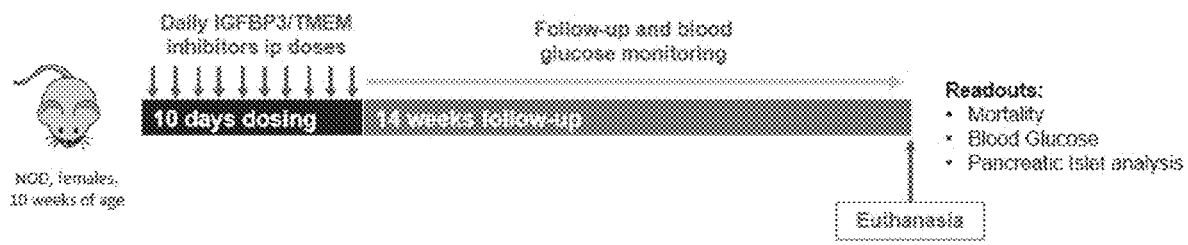
FIG. 4. Effect of newly generated anti-TMEM219 mAbs on diabetes onset in T1D mice model. Experimental timelines of NOD mice study.
Figure 5:
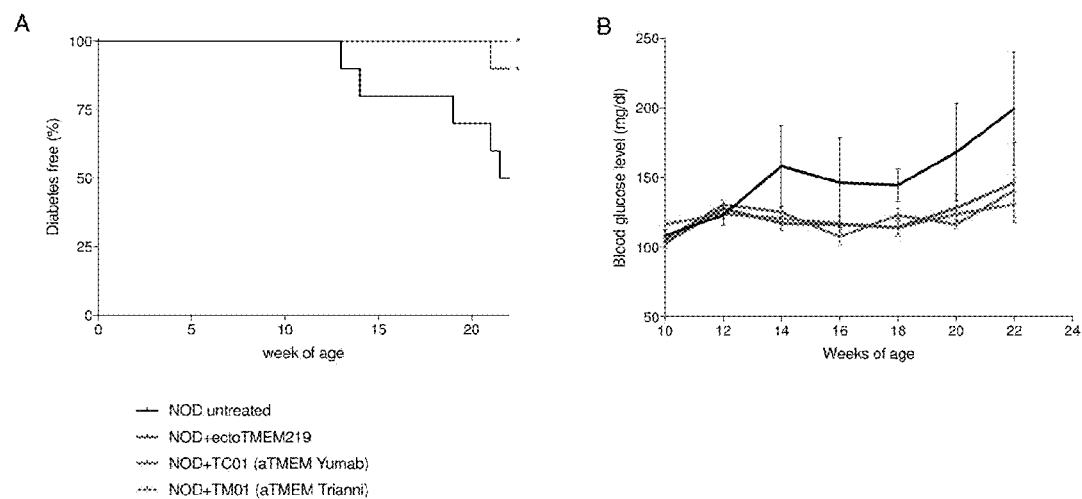
FIG. 5. (A) Anti-TMEM219 mAbs effect in preventing diabetes onset in NOD mice at 22 weeks of age and (B) in preserving blood glucose levels. Diabetes prevention obtained by the use of anti-TMEM219 mAbs was observed in 100% of mice. *p<0.05 by Mantel-Cox analysis vs. untreated. Diabetes-free are the normoglycemic mice. Blood glucose >250 mg/dl for three consecutive measurements defined diabetes onset. Diabetes-free mice do not have Blood glucose >250 mg/dl for three consecutive measurements.

As shown in FIGS. 4 and 5, the inventors assessed whether 10 day-administration of newly generated anti-TMEM219 mAbs prevent clinical diabetes onset in NOD mice, a mouse model selective to study autoimmune type 1 diabetes (T1D). Remarkably, Anti-TMEM219 mAbs maintain blood glucose level under control over time and are effective in preventing diabetes onset in T1D NOD mouse model. Interestingly, 100% of mice treated with the antibodies TM1 and TC01 were free from diabetes at week 22 as compared to 50% of untreated controls (p<0.05 all vs. untreated).

Figure 6:
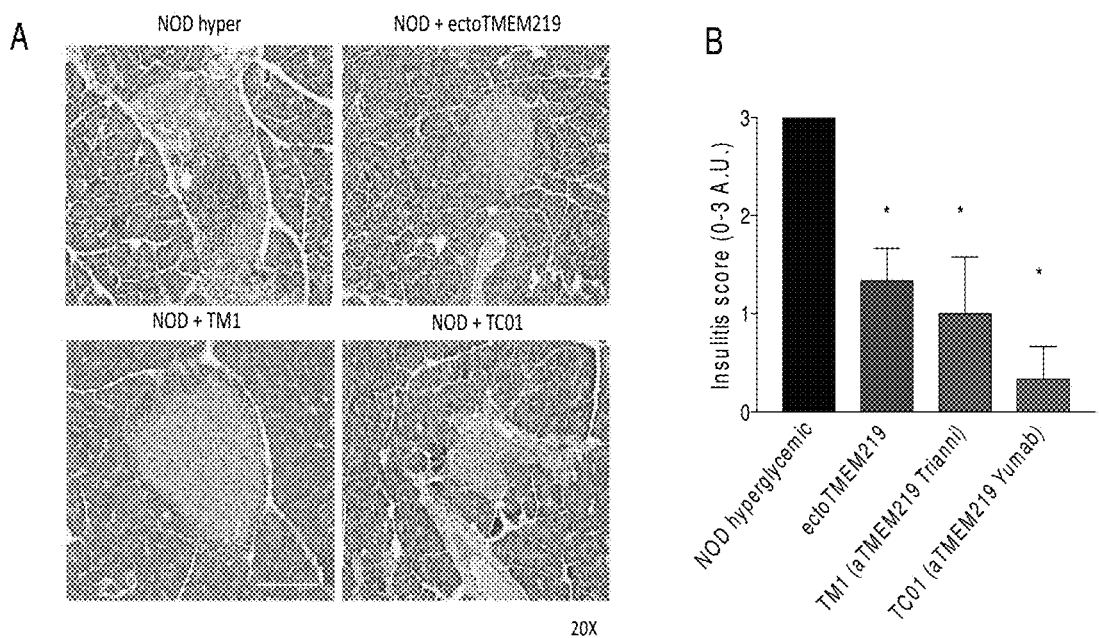
FIG. 6. Serial paraffin sections of pancreatic tissue obtained at euthanasia were prepared, stained with H&E and islet area and morphology were analyzed microscopically. (A) Representative images are shown; original magnification 20×. (B) Insulitis scores are shown. In (B), the extent of cell infiltration was scored from 0 through 4. Insulitis was scored by examining a minimum of 30 islets per animal. *p<0.05 by Mann Whitney test all vs. untreated.
Figure 7:
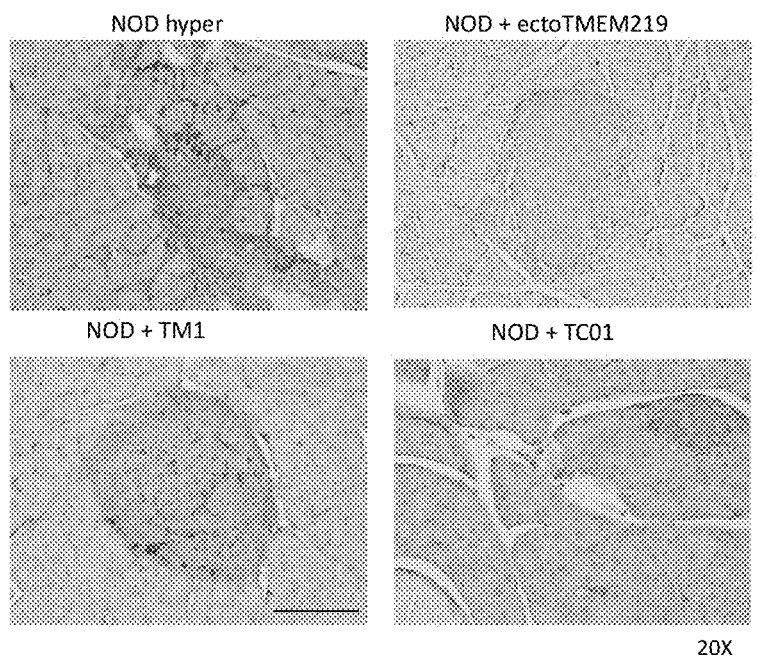
FIG. 7. Serial paraffin sections of pancreatic tissue obtained at euthanasia were prepared showing immunohistochemical staining for insulin (brown color). Representative images are shown, original magnification 20×.

Next, pancreatic tissue sections of NOD mice obtained from untreated mice, TM1-treated, TC01-treated and Ecto-TMEM219-treated mice were analyzed for islet infiltration (insulitis), islet area and morphology (FIG. 6A) and insulin staining (FIG. 7). Both TM1 and TC01-treated groups showed good islet morphology, in addition, area appeared slightly increased in TM1-treated mice, suggesting that treatment with anti-TMEM mAbs prevents islet destruction, enabling normal function of beta cells. Moreover, TM1 and TC01-treated mice showed a well-preserved insulin positivity as compared to untreated controls, further supporting that the function of the islets was preserved. Indeed, islet infiltration was strikingly decreased in treated mice, as compared to untreated mice, thus supporting the protective role of the antibodies (FIG. 7). Then the present data show the efficacy of anti-TMEM monoclonal antibodies for the prevention and/or treatment of diabetes.

Figure 8:
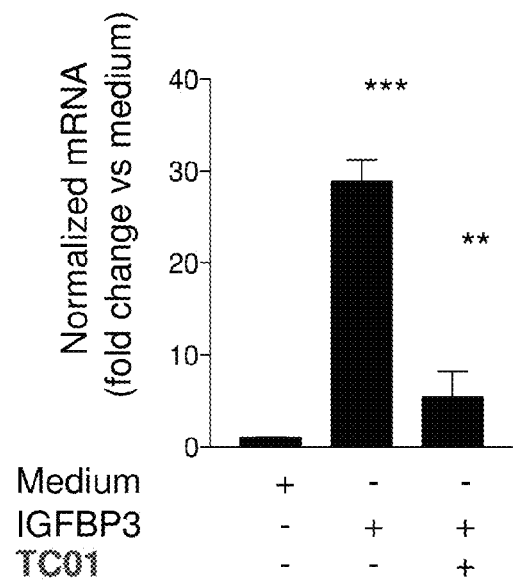
FIG. 8. Effects of anti-TMEM219 mAbs in downregulating CASP8 expression in beta cell line exposed to IGFBP3.
Figure 9:
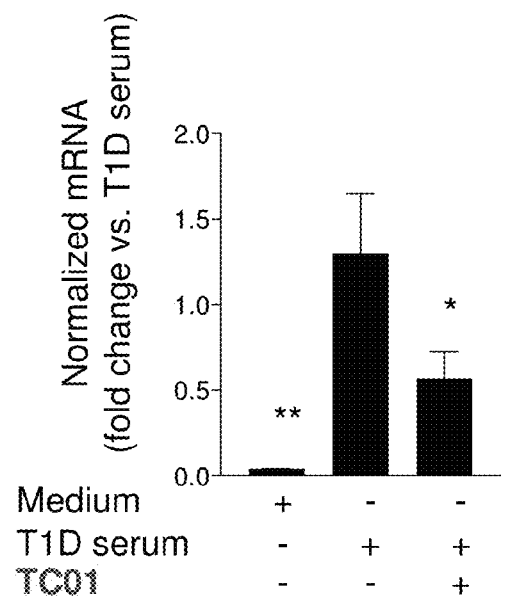
FIG. 9. Effects of anti-TMEM219 mAbs in downregulating CASP8 expression in beta cell line exposed to T1D serum enriched in IGFBP3.

Example 4: Newly Generated Monoclonal Anti-TMEM219 Antibodies Inhibits Apoptosis in a Human Beta Cell Line In order to confirm that the newly generated monoclonal anti-TMEM219 antibodies may prevent the pro-apoptotic effects of IGFBP3 on TMEM219-expressing cells within the pancreas, we further tested them in vitro in a beta cell line, the Betalox-5. Upregulation of CASP8 induced by IGFBP3 exposure was counteracted by the newly generated anti-TMEM219 mAb, with nearly 30% of CASP8 reduction. Moreover, exposure of beta cells to pooled T1D serum enriched in IGFBP3 increased CASP8 expression and anti-TMEM219 mAb was able to counterbalance this effect by reducing CASP8 of at least 30%, thus supporting the beneficial effects of these newly generated monoclonal anti-TMEM219 antibodies in preventing pancreatic beta cells apoptosis (FIGS. 8 and 9).

Figure 10:
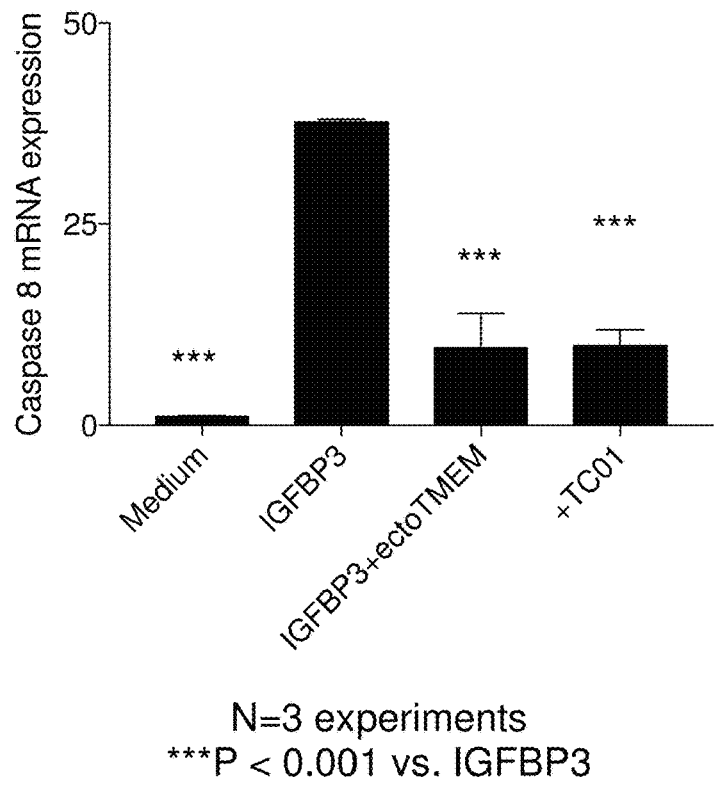
FIG. 10. Effects of anti-TMEM219 mAbs in downregulating CASP8 expression in human islets exposed to IGFBP3.
Figure 11:
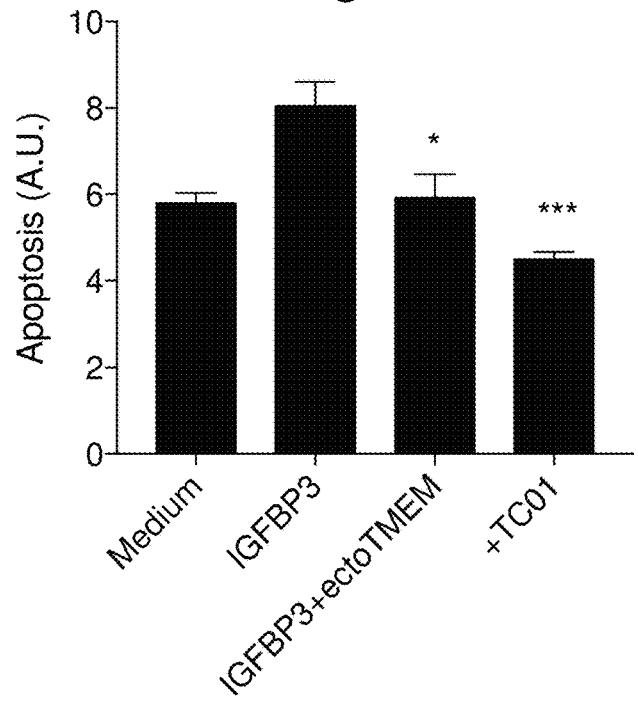
FIG. 11. Effects of anti-TMEM219 mAbs in reducing apoptosis in human islets exposed to IGFBP3.
Figure 12:
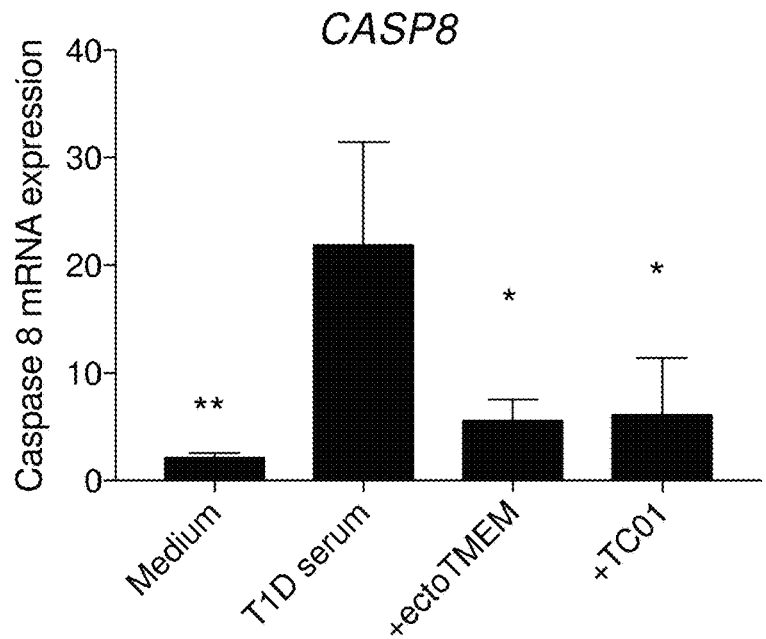
FIG. 12. Effects of anti-TMEM219 mAbs in downregulating CASP8 expression in human islets exposed to T1D serum.
Figure 13:
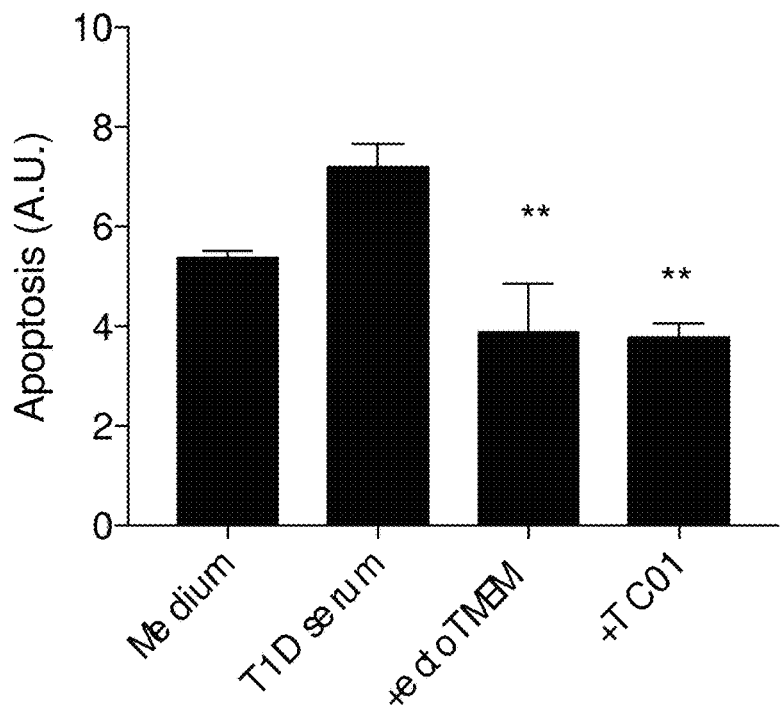
FIG. 13. Effects of anti-TMEM219 mAbs in reducing apoptosis in human islets exposed to T1D serum.

Example 5: Newly Generated Monoclonal Anti-TMEM219 Antibodies Inhibit Apoptosis in Human Islets In order to confirm that the newly generated monoclonal anti-TMEM219 antibodies may prevent the pro-apoptotic effects of IGFBP3 on TMEM219-expressing cells within the pancreas, we further tested them in vitro in human islets (Celprogen). Upregulation of CASP8 as well as apoptosis induced by IGFBP3 exposure were counteracted by the newly generated anti-TMEM219 mAb (FIGS. 10 and 11), with a reduction of 40% of CASP8 and 30% of apoptosis. Interestingly, exposure of human islets to pooled T1D serum naturally enriched in IGFBP3 increased CASP8 expression and apoptosis and anti-TMEM219 mAb was able to counterbalance this effect by decreasing both CASP8 and apoptosis by nearly 50%, thus supporting the beneficial effects of the newly generated monoclonal anti-TMEM219 antibodies in preventing islets apoptosis (FIGS. 12 and 13).

Figure 14:
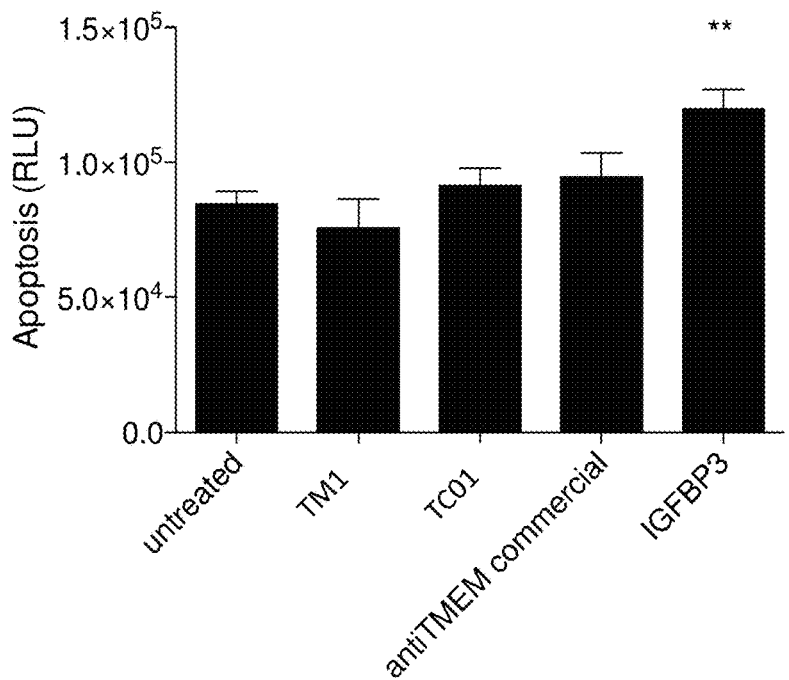
FIG. 14. Effects of anti-TMEM219 mAbs on apoptosis of beta cell line.
Figure 15:
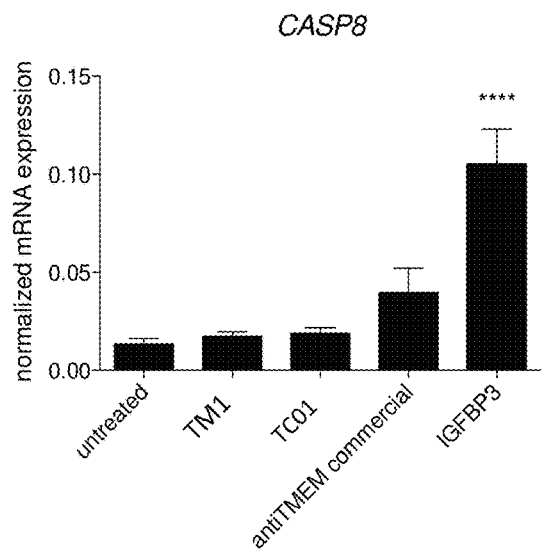
FIG. 15. Effects of anti-TMEM219 mAbs on CASP8 mRNA expression in beta cell line.

Example 6: Newly Generated Monoclonal Anti-TMEM219 Antibodies are not Toxic for Beta Cells To demonstrate that the newly generated monoclonal anti-TMEM219 antibodies do not activate TMEM219 downstream signaling thus inducing cell apoptosis in absence of IGFBP3 ligation, we performed two major assays. First, we demonstrated that antiTMEM219-treated beta cells do not undergo apoptosis as compared to those challenged with IGFBP3, which induces an increase of nearly 30% of cell death (FIG. 14). Next, we assessed CASP8 mRNA expression and demonstrated an upregulation in beta cells cultured with IGFBP3 as expected (nearly 70%) while CASP8 remained unaltered in anti-TMEM219-cultured beta cells (FIG. 15). These data altogether support the absence of any toxic/apoptotic effect of anti-TMEM219 mAbs.

Example 7: Anti-TMEM219 mAbs Effects in Streptozotocin-Induced Beta Cell Death Diabetes Model We further tested the effect of IGFBP3/TMEM219 pharmacological blockade through anti-TMEM219 mAbs in a second model of beta cell destruction and diabetes, a multiple low dose of streptozotocin (ldSTZ, 50 mg/Kg for 5 days).

The chemically induced diabetes with Streptozotocin injection is employed to assess the effects of a targeting strategy primarily on the beta cell mass. It is associated with the development of mild inflammation but no autoimmune response such as that observed in the NOD mouse occurs. Therefore, the success of a compound in preserving the blood glucose level resides mainly in preserving the beta cell mass from damage and in maintaining insulin secretion.

Figure 16:
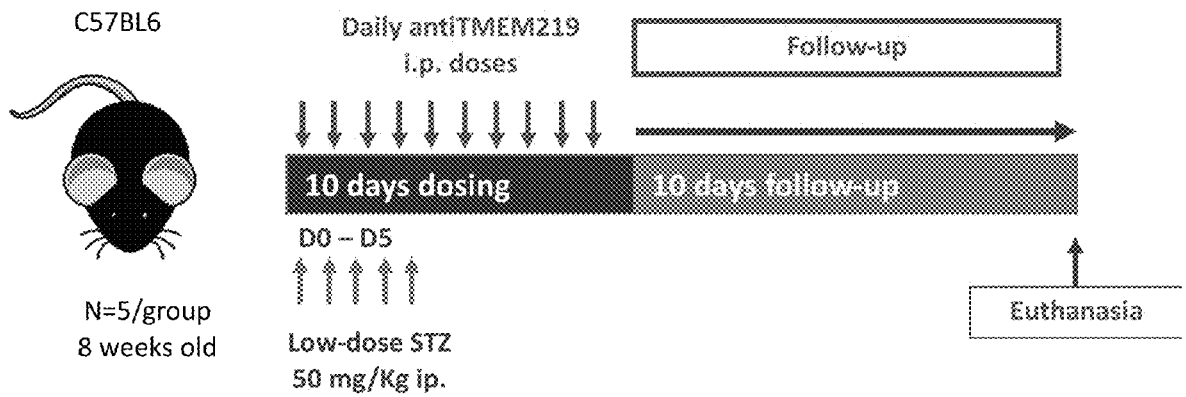
FIG. 16. Effect of newly generated anti-TMEM219 mAbs on diabetes onset in diabetes mice model. Experimental timelines of Low dose streptozotocin model of diabetes.
Figure 17:
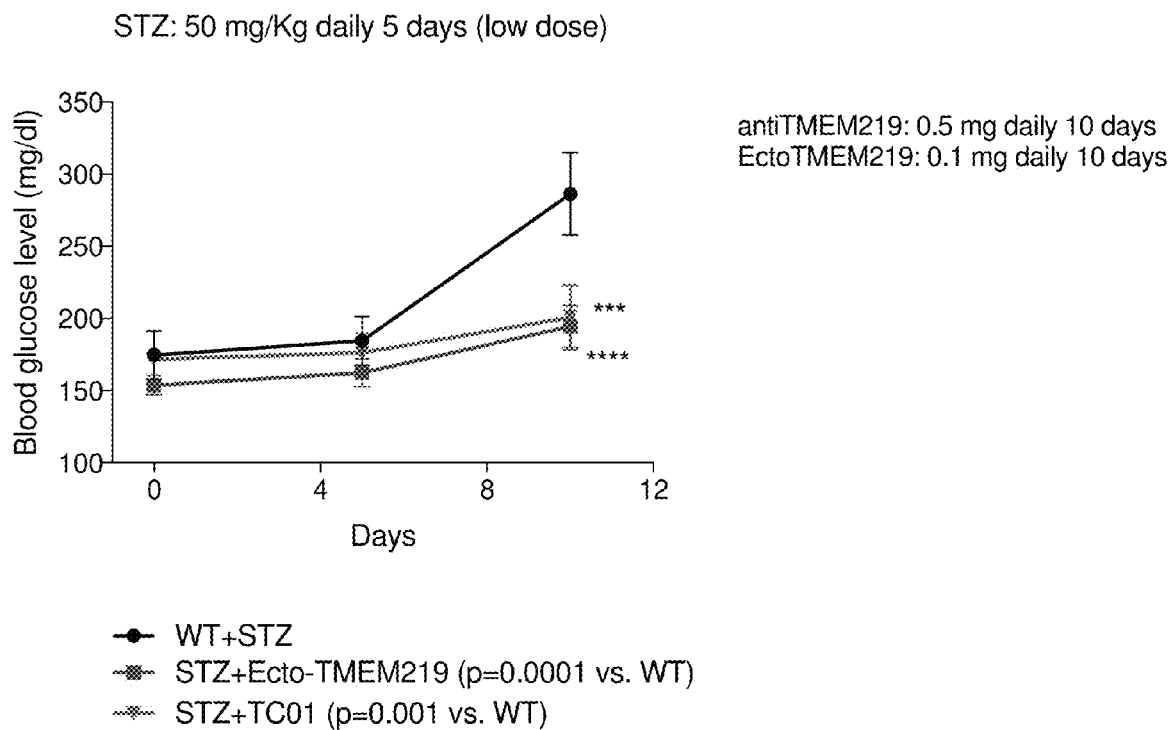
FIG. 17. Line graph showing blood glucose level measured in B6 mice injected with multiple low-dose of streptozotocin (IdSTZ, 50 mg/Kg) and treated with anti-TMEM219 mAbs or left untreated (n=5).
Figure 18:
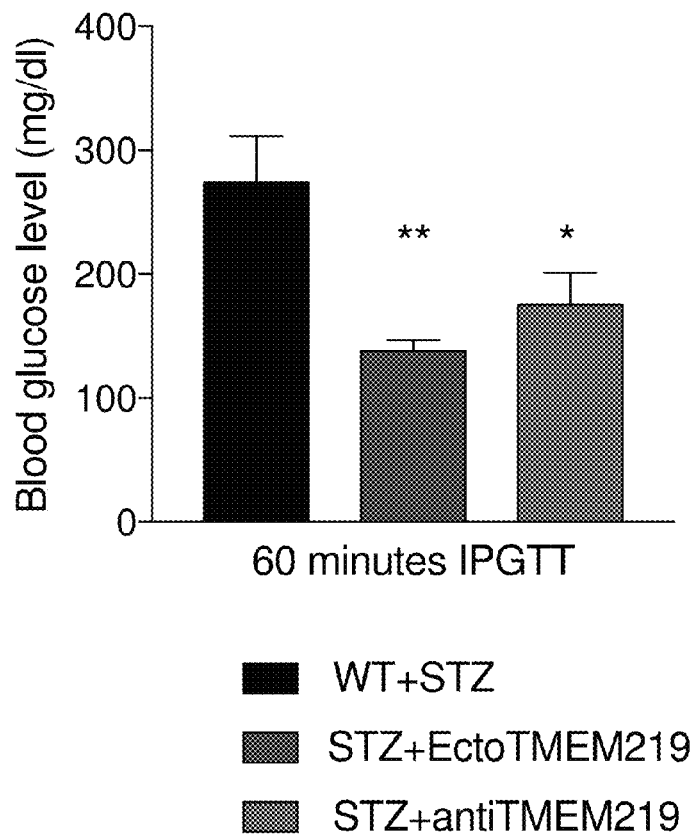
FIG. 18. Blood glucose measured at 60 minutes during the IPGTT (1 g/Kg) in B6 mice injected with Id-STZ with/without anti-TMEM219 mAbs at day 10 (n=5). *p<0.05, **p<0.01.
Figure 19:
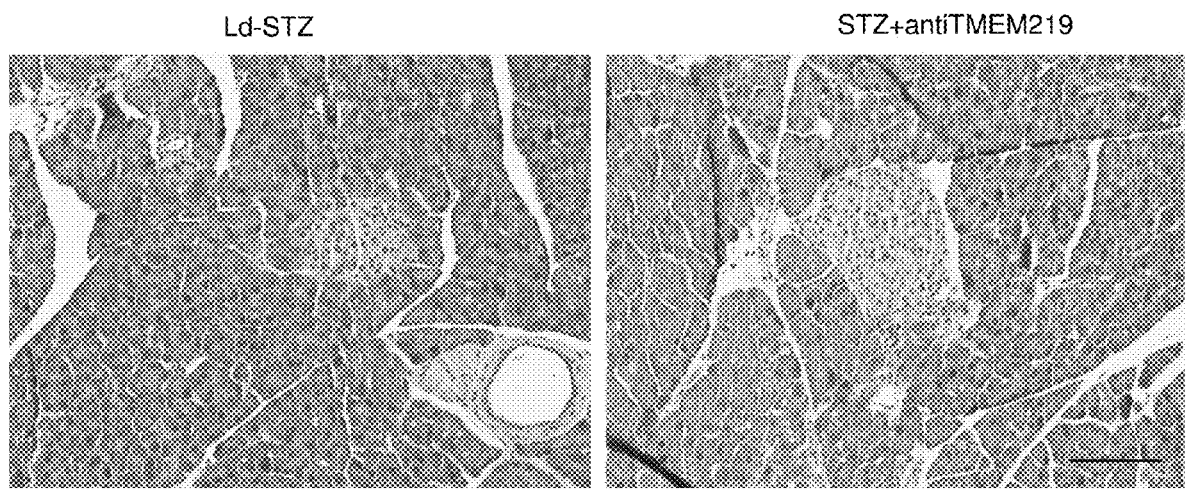
FIG. 19. Representative H&E staining in serial pancreatic islet tissue sections obtained from B6 mice injected with IdSTZ and treated with/without anti-TMEM219 mAb (n=3). 20× original magnification, scale bar, 100 μm.

Streptozotocin induces beta cell death such as that observed in diabetes when administered by using a low-dose regimen of 50 mg/Kg for 5 consecutive days and diabetes/hyperglycemia usually develop within the first 2 weeks from the administration (FIG. 16). Therefore, we administered low-dose STZ for 5 days to B6 mice, who simultaneously received anti-TMEM219 mAbs at a dose of 0.5 mg/day for 10 days. Anti-TMEM219 mAbs treatment successfully preserved blood glucose levels in treated mice as compared to untreated animals (FIG. 17), with an improvement also of the blood glucose level detected at 60 minutes during the intraperitoneal glucose tolerance test (IPGTT), (FIG. 18). Morphology analysis also revealed that islet number and area was well-preserved in animals treated with anti-TMEM219 mAbs as compared to untreated mice (FIG. 19). Overall, this confirms that anti-TMEM219 may preserve beta cell mass and maintain blood glucose level also in a model of beta cell destruction thus highlighting the benefit of this strategy in protecting islets from diabetes-induced beta cell loss and dysfunction.

The anti-TMEM219 antibodies such as TC01 are effective in protecting beta cell from injury and preventing their loss, further preserving their ability to respond to glucose stimulation. Also, no inflammation is detectable in islets of mice treated with anti-TMEM219 TC01, thus confirming the protective effect on islet morphology.

Methods for Examples 4-7

Recombinant Proteins and Interventional Studies
Recombinant human IGFBP3 (Life Technologies, 10430H07H5), 50 ng/ml (IGFBP3) and ecto-TMEM219, 130 ng/ml were added to cultures at day +1 from mini-guts culture. Newly generated anti-TMEM219 monoclonal antibodies were added at 1:1 molecular ratio as compared to IGFBP3 at 10 µg/ml concentration.
Beta Cell Line (Beta-Lox5)
Cells were cultured with DMEM 10% FBS, 0.02% BSA, 15 mM HEPES, NEA 1×, 1 g/L Glucose, PEN/STREP. Cells are usually seeded into 35-mm wells at a density of 10,000 cells/well. Cells are passaged at 80% confluency. Cells were cultured cultured for 3 days with/without recombinant proteins/Antibodies as described in the Recombinant proteins and interventional studies section.
Human Islets
Human pancreatic islets of Langherans (#35002-04) isolated from healthy subjects were also purchased from a commercial source (Celprogen, Torrance, CA) and cultured with standard medium and 10% FBS as per the manufacturer's instructions. To mimic diabetic conditions, human diabetic serum obtained from established T1D (n=5/group) was added in place of regular FBS at a concentration of 10% to human islets/beta cell lines.
Islet/Beta Cells Cell Death
To assess apoptosis/cell death in purified human islets and in beta cell lines we employed a photometric enzyme immunoassay (Roche Diagnostics GmbH, 11544675001, Mannheim, Germany), which quantifies in vitro the histoneassociated DNA fragments after induced cell stress on cell cytoplasmic lysates and cell supernatants.

STZ-Induced Diabetes Studies

Diabetes was chemically induced by injecting low dose streptozotocin (50 mg/Kg, administered i.p.; Sigma Aldrich S0130) for 5 consecutive days, and glycemia was monitored for the next 15 days. A control group consisting of wild-type B6 mice was injected with low dose streptozotocin as well and monitored accordingly. Anti-TMEM219 mAbs and ecto-TMEM219 were also administered i.p. from day 0 to day 10 at a dose of 0.5 mg/day and 0.1 mg/day respectively, and glycemia was monitored for the following 15 days. An intraperitoneal glucose tolerance test (IPGTT) was performed at the end by injecting glucose 1 Kg/g in mice after overnight starvation and glycemia was monitored at 0, 30, 60 and 120 minutes.

Statistical Analysis

Data are presented as mean and standard error of the mean (SEM). The statistical significance of differences was tested with two-tailed t-test. Significance between the two groups was determined by two-tailed unpaired Student's t test. For multiple comparisons, the ANOVA test with Bonferroni correction was employed. Graphs were generated using GraphPad Prism version 5.0 (GraphPad Software, La Jolla, CA). All statistical tests were performed at the 5% significance level.

REFERENCES

1. Baxter R C. J Cell Commun Signal. 2013; 7(3):179-89.
2. Oh Y, et al., Prog Growth Factor Res. 1995; 6(2-4):503-12.
3. Ingermann A R, et al. JBC. 2010; 285(39):30233-46.
4. D'Addio F, et al. Cell stem cell. 2015; 17(4):486-98.
5. Brennand K, and Melton D. J. of cellular and molecular med.. 2009; 13(3):472-87.
6. Yi P, Park J S, and Melton D A. Cell. 2014; 159(3):467-8.
7. Ben Nasr M, et al., Pharmacological res.: the official journal of the Italian Pharmacological Society. 2015; 98:31-8.
8. Keenan H A, et al. Diabetes. 2010; 59(11):2846-53.
9. Meier J J, et al., Diabetologia. 2005; 48(11):2221-8.
10. Atkinson M A, et al., Diabetes care. 2015; 38(6):979-88.
11. Nguyen K H, et al., Endocrinology. 2011; 152(6):2184-96.
12. Yakar S, et al., FASEB J. 2009; 23(3):709-19.
13. Drogan D, et al., Am J Epidemiol. 2016; 183(6):553-60.
14. Peet A, et al., Eur J Endocrinol. 2015; 173(2):129-37.
15. Kaplan G G. Nat Rev Gastroenterol Hepatol. 2015; 12(12):720-7.
16. Cui S, and Chang P Y. World J Gastroenterol. 2016; 22(31):7099-110.
17. Yancu D, et al., J Gastroenterol Hepatol. 2017; 32(1):146-53.
18. Jung P, et al., Nature Medecine 2011; 17:1225-1227.
19. George M J, et al., Curr Diab Rep 2013; 13(1):72-80.
21. Marsha J D. Am Health Drug Benefits 2011; 4(5):312-322
22. Dhingra A K et al., Antiinflamm Antiallergy Agents Med Chem. 2015; 14(2):81-97.
23. Pithadia A B, SunitaJ. Pharmacoligal rep 2011; 63:629-642
24. Zhe Wang, et al., Expert Opin Drug Deliv. 2010 February; 7(2):159-71
25. Sumit G, Wei W, Tsutomu and Satoshi O, Antibodies 2013; 2: 452-500;
26. Beck A, et al., Nat Rev Imm 2010; 10: 345-352
27. Huch M, et al., Nature 2013; 494 (7436): 247-250
28. Mahe M M, et al., Curr Protoc Mouse Biol 2013; 3: 217-240
29. Shimkets R A, Gene Expression Profiling. Meth. in Mol. Biology; 258. Humana Press
30. Raghavachari N, et al., Gene Expression Analaysis, Meth. in Mol. Biol; 1783. Humana Press
31. Kurien B T, et al., Western Blotting, Methods in Molecular Biology; 1312. Humana Press
32. Hnasko R, ELISA, Methods in Molecular Blology, 1318. Humana Press
33. Lipton M S, et al., Mass Spec. of Proteins and Peptides, Meth. in Mol. Biol., 492. Humana Press
34. Brady H, Apoptosis Meth. and Protocols, Meth. in Mol. Biol., 282. Humana Press
35. Cheryl L et al., Protein-Protein interactions, Meth. in Mol. Biol., 1278. Humana Press

---

The invention claimed is:

1. An antibody or antigen-binding fragment thereof comprising three heavy chain variable region (VH) CDRs and three light chain variable region (VL) CDRs, wherein
   (a) the three VH CDRs respectively have the sequences of SEQ ID NO:4, SEQ ID NO:5, and SEQ ID NO:6, and the three VL CDRs respectively have the sequences of SEQ ID NO:17, SEQ ID NO:18, and SEQ ID NO:19; or
   (b) the three VH CDRs respectively have the sequences of SEQ ID NO:4, SEQ ID NO:5, and SEQ ID NO:6, and the three VL CDRs respectively have the sequences of SEQ ID NO:17, SEQ ID NO:18, and SEQ ID NO:166,
   wherein the antibody or antigen-binding fragment thereof is capable of binding to transmembrane protein 219 (TMEM219).

2. The antibody or antigen binding fragment thereof of claim 1, wherein the three VH CDRs respectively have the sequences of SEQ ID NO:4, SEQ ID NO:5, and SEQ ID NO:6, and the three VL CDRs respectively have the sequences of SEQ ID NO:17, SEQ ID NO:18, and SEQ ID NO:19.

3. The antibody or antigen binding fragment thereof of claim 2, comprising a VH having the sequence of SEQ ID NO:33.

4. A pharmaceutical composition comprising:
   (a) the antibody or antigen-binding fragment thereof of claim 3, and
   (b) a pharmaceutically acceptable carrier.

5. The antibody or antigen binding fragment thereof of claim 2, comprising a VL having the sequence of SEQ ID NO:39.

6. A pharmaceutical composition comprising:
   (a) the antibody or antigen-binding fragment thereof of claim 5, and
   (b) a pharmaceutically acceptable carrier.

7. The antibody or antigen binding fragment thereof of claim 2, comprising a VH having the sequence of SEQ ID NO:33 and a VL having the sequence of SEQ ID NO:39.

8. A pharmaceutical composition comprising:
   (a) the antibody or antigen-binding fragment thereof of claim 7, and
   (b) a pharmaceutically acceptable carrier.

9. The antibody or antigen binding fragment thereof of claim 2, wherein the antibody is a monoclonal antibody.

10. The monoclonal antibody of claim 9, wherein the antibody is a human or humanized antibody.

11. A pharmaceutical composition comprising:
    (a) the monoclonal antibody of claim 10, and
    (b) a pharmaceutically acceptable carrier.

12. The monoclonal antibody of claim 9, wherein the antibody is an IgG1, IgG2 or IgG4 antibody.

13. The IgG2 antibody of claim 12, wherein the IgG2 antibody is a IgG2 kappa antibody or an IgG2 lambda antibody.

14. A pharmaceutical composition comprising:
    (a) the IgG2 antibody of claim 13, and
    (b) a pharmaceutically acceptable carrier.

15. The IgG4 antibody of claim 12, wherein the IgG4 antibody is a IgG4 kappa antibody or an IgG4 lambda antibody.

16. A pharmaceutical composition comprising:
    (a) the IgG4 antibody of claim 15, and
    (b) a pharmaceutically acceptable carrier.

17. The IgG4 antibody of claim 12, wherein the IgG4 antibody comprises S228P and L235E mutations.

18. A pharmaceutical composition comprising:
    (a) the IgG4 antibody of claim 17, and
    (b) a pharmaceutically acceptable carrier.

19. A pharmaceutical composition comprising:
    (a) the monoclonal antibody of claim 12, and
    (b) a pharmaceutically acceptable carrier.

20. A pharmaceutical composition comprising:
    (a) the monoclonal antibody of claim 9, and
    (b) a pharmaceutically acceptable carrier.

21. A pharmaceutical composition comprising:
    (a) the antibody or antigen-binding fragment thereof of claim 2, and
    (b) a pharmaceutically acceptable carrier.

22. A pharmaceutical composition comprising:
    (a) the antibody or antigen-binding fragment thereof of claim 1,
    and
    (b) a pharmaceutically acceptable carrier,
    wherein the antibody or antigen-binding fragment thereof is capable of binding to TMEM219.

* * * * *

SEQUENCE LISTING

```
Sequence total quantity: 179
SEQ ID NO: 1            moltype = AA  length = 5
FEATURE                 Location/Qualifiers
REGION                  1..5
                        note = synthetic
source                  1..5
                        mol_type = protein
                        organism = synthetic construct
SEQUENCE: 1
SYAIS                                                                    5

SEQ ID NO: 2            moltype = AA  length = 17
FEATURE                 Location/Qualifiers
REGION                  1..17
                        note = synthetic
source                  1..17
                        mol_type = protein
                        organism = synthetic construct
SEQUENCE: 2
GIIPIFGTAN YAQKFQG                                                       17

SEQ ID NO: 3            moltype = AA  length = 18
FEATURE                 Location/Qualifiers
REGION                  1..18
                        note = synthetic
```

-continued

| | | |
|---|---|---|
| source | 1..18<br>mol_type = protein<br>organism = synthetic construct | |
| SEQUENCE: 3 | | |
| GDIAAAGRKG LPIYYMDV | | 18 |
| | | |
| SEQ ID NO: 4<br>FEATURE<br>REGION | moltype = AA   length = 4<br>Location/Qualifiers<br>1..4<br>note = synthetic | |
| source | 1..4<br>mol_type = protein<br>organism = synthetic construct | |
| SEQUENCE: 4 | | |
| SYGI | | 4 |
| | | |
| SEQ ID NO: 5<br>FEATURE<br>REGION | moltype = AA   length = 17<br>Location/Qualifiers<br>1..17<br>note = synthetic | |
| source | 1..17<br>mol_type = protein<br>organism = synthetic construct | |
| SEQUENCE: 5 | | |
| WISAYNGNTN YAQKLQG | | 17 |
| | | |
| SEQ ID NO: 6<br>FEATURE<br>REGION | moltype = AA   length = 9<br>Location/Qualifiers<br>1..9<br>note = synthetic | |
| source | 1..9<br>mol_type = protein<br>organism = synthetic construct | |
| SEQUENCE: 6 | | |
| WGRWLAHDY | | 9 |
| | | |
| SEQ ID NO: 7<br>FEATURE<br>REGION | moltype = AA   length = 12<br>Location/Qualifiers<br>1..12<br>note = synthetic | |
| source | 1..12<br>mol_type = protein<br>organism = synthetic construct | |
| SEQUENCE: 7 | | |
| PSGYYIYDAF DI | | 12 |
| | | |
| SEQ ID NO: 8<br>FEATURE<br>REGION | moltype = AA   length = 5<br>Location/Qualifiers<br>1..5<br>note = synthetic | |
| source | 1..5<br>mol_type = protein<br>organism = synthetic construct | |
| SEQUENCE: 8 | | |
| SYGIS | | 5 |
| | | |
| SEQ ID NO: 9<br>FEATURE<br>REGION | moltype = AA   length = 8<br>Location/Qualifiers<br>1..8<br>note = synthetic | |
| source | 1..8<br>mol_type = protein<br>organism = synthetic construct | |
| SEQUENCE: 9 | | |
| DLGWPDDY | | 8 |
| | | |
| SEQ ID NO: 10<br>FEATURE<br>REGION | moltype = AA   length = 5<br>Location/Qualifiers<br>1..5<br>note = synthetic | |
| source | 1..5<br>mol_type = protein<br>organism = synthetic construct | |
| SEQUENCE: 10 | | |
| DYGMS | | 5 |
| | | |
| SEQ ID NO: 11<br>FEATURE<br>REGION | moltype = AA   length = 17<br>Location/Qualifiers<br>1..17 | |

```
                          note = synthetic
source                    1..17
                          mol_type = protein
                          organism = synthetic construct
SEQUENCE: 11
GINWNGGSTG YADSVKG                                                     17

SEQ ID NO: 12             moltype = AA  length = 16
FEATURE                   Location/Qualifiers
REGION                    1..16
                          note = synthetic
source                    1..16
                          mol_type = protein
                          organism = synthetic construct
SEQUENCE: 12
DRLRYCSSTS CYIPDY                                                      16

SEQ ID NO: 13             moltype = AA  length = 19
FEATURE                   Location/Qualifiers
REGION                    1..19
                          note = synthetic
source                    1..19
                          mol_type = protein
                          organism = synthetic construct
SEQUENCE: 13
VGSTYDFWSG AYYYYGMDV                                                   19

SEQ ID NO: 14             moltype = AA  length = 11
FEATURE                   Location/Qualifiers
REGION                    1..11
                          note = synthetic
source                    1..11
                          mol_type = protein
                          organism = synthetic construct
SEQUENCE: 14
QASQDISNYL N                                                           11

SEQ ID NO: 15             moltype = AA  length = 7
FEATURE                   Location/Qualifiers
REGION                    1..7
                          note = synthetic
source                    1..7
                          mol_type = protein
                          organism = synthetic construct
SEQUENCE: 15
AASSLQS                                                                7

SEQ ID NO: 16             moltype = AA  length = 8
FEATURE                   Location/Qualifiers
REGION                    1..8
                          note = synthetic
source                    1..8
                          mol_type = protein
                          organism = synthetic construct
SEQUENCE: 16
QQSYSTPT                                                               8

SEQ ID NO: 17             moltype = AA  length = 11
FEATURE                   Location/Qualifiers
REGION                    1..11
                          note = synthetic
source                    1..11
                          mol_type = protein
                          organism = synthetic construct
SEQUENCE: 17
SGDKLGNKNA Y                                                           11

SEQ ID NO: 18             moltype = AA  length = 7
FEATURE                   Location/Qualifiers
REGION                    1..7
                          note = synthetic
source                    1..7
                          mol_type = protein
                          organism = synthetic construct
SEQUENCE: 18
QSTRRPS                                                                7

SEQ ID NO: 19             moltype = AA  length = 11
FEATURE                   Location/Qualifiers
```

```
REGION                  1..11
                        note = synthetic
source                  1..11
                        mol_type = protein
                        organism = synthetic construct
SEQUENCE: 19
QAWDSSSGWE V                                                                    11

SEQ ID NO: 20           moltype = AA  length = 12
FEATURE                 Location/Qualifiers
REGION                  1..12
                        note = synthetic
source                  1..12
                        mol_type = protein
                        organism = synthetic construct
SEQUENCE: 20
GASQSVSSSY LA                                                                   12

SEQ ID NO: 21           moltype = AA  length = 7
FEATURE                 Location/Qualifiers
REGION                  1..7
                        note = synthetic
source                  1..7
                        mol_type = protein
                        organism = synthetic construct
SEQUENCE: 21
DASSRAT                                                                          7

SEQ ID NO: 22           moltype = AA  length = 9
FEATURE                 Location/Qualifiers
REGION                  1..9
                        note = synthetic
source                  1..9
                        mol_type = protein
                        organism = synthetic construct
SEQUENCE: 22
HQYNNWPRT                                                                        9

SEQ ID NO: 23           moltype = AA  length = 13
FEATURE                 Location/Qualifiers
REGION                  1..13
                        note = synthetic
source                  1..13
                        mol_type = protein
                        organism = synthetic construct
SEQUENCE: 23
SGSSSNIGSN YVY                                                                  13

SEQ ID NO: 24           moltype = AA  length = 7
FEATURE                 Location/Qualifiers
REGION                  1..7
                        note = synthetic
source                  1..7
                        mol_type = protein
                        organism = synthetic construct
SEQUENCE: 24
RNNQRPS                                                                          7

SEQ ID NO: 25           moltype = AA  length = 11
FEATURE                 Location/Qualifiers
REGION                  1..11
                        note = synthetic
source                  1..11
                        mol_type = protein
                        organism = synthetic construct
SEQUENCE: 25
AAWDDSLNGV V                                                                    11

SEQ ID NO: 26           moltype = AA  length = 17
FEATURE                 Location/Qualifiers
REGION                  1..17
                        note = synthetic
source                  1..17
                        mol_type = protein
                        organism = synthetic construct
SEQUENCE: 26
KSSQSVLDSS NNKNYVA                                                              17

SEQ ID NO: 27           moltype = AA  length = 7
```

```
FEATURE                 Location/Qualifiers
REGION                  1..7
                        note = synthetic
source                  1..7
                        mol_type = protein
                        organism = synthetic construct
SEQUENCE: 27
WASTRES                                                                 7

SEQ ID NO: 28           moltype = AA  length = 9
FEATURE                 Location/Qualifiers
REGION                  1..9
                        note = synthetic
source                  1..9
                        mol_type = protein
                        organism = synthetic construct
SEQUENCE: 28
QQYYTTRWT                                                               9

SEQ ID NO: 29           moltype = AA  length = 11
FEATURE                 Location/Qualifiers
REGION                  1..11
                        note = synthetic
source                  1..11
                        mol_type = protein
                        organism = synthetic construct
SEQUENCE: 29
RASQGIRNDL G                                                            11

SEQ ID NO: 30           moltype = AA  length = 7
FEATURE                 Location/Qualifiers
REGION                  1..7
                        note = synthetic
source                  1..7
                        mol_type = protein
                        organism = synthetic construct
SEQUENCE: 30
DASNLET                                                                 7

SEQ ID NO: 31           moltype = AA  length = 9
FEATURE                 Location/Qualifiers
REGION                  1..9
                        note = synthetic
source                  1..9
                        mol_type = protein
                        organism = synthetic construct
SEQUENCE: 31
QQYDNLPLT                                                               9

SEQ ID NO: 32           moltype = AA  length = 127
FEATURE                 Location/Qualifiers
REGION                  1..127
                        note = synthetic
source                  1..127
                        mol_type = protein
                        organism = synthetic construct
SEQUENCE: 32
QVQLVQSGAE VKRPGSSVKV SCKASGGTFS SYAISWVRQA PGQGLEWMGG IIPIFGTANY        60
AQKFQGRVTI TADESTSTAY MELSNLRSED TAVYYCARGD IAAAGRKGLP IYYMDVWGKG        120
TTVTVSS                                                                 127

SEQ ID NO: 33           moltype = AA  length = 118
FEATURE                 Location/Qualifiers
REGION                  1..118
                        note = synthetic
source                  1..118
                        mol_type = protein
                        organism = synthetic construct
SEQUENCE: 33
QIQLVQSGAE VKKPGASVKV SCKASGYTFT SYGISWVRQA PGQGLEWMGW ISAYNGNTNY        60
AQKLQGRVTM TTDTSTSTAY MELRSLRSDD TAVYYCARWG RWLAHDYWGQ GTLVTVSS         118

SEQ ID NO: 34           moltype = AA  length = 121
FEATURE                 Location/Qualifiers
REGION                  1..121
                        note = synthetic
source                  1..121
                        mol_type = protein
                        organism = synthetic construct
```

```
SEQUENCE: 34
QMQLVQSGAE VKKPGSSVKV SCKASGGTFS SYAISWVRQA PGQGLEWMGG IIPIFGTANY    60
AQKFQGRVTI TADESTSTAY MELSSLRSED TAVYYCASPS GYYIYDAFDI WGQGTMVTVS   120
S                                                                  121

SEQ ID NO: 35           moltype = AA  length = 117
FEATURE                 Location/Qualifiers
REGION                  1..117
                        note = synthetic
source                  1..117
                        mol_type = protein
                        organism = synthetic construct
SEQUENCE: 35
QVQLVQSGAE VKKPGASVKV SCKASGYTFT SYGISWVRQA PGQGLEWMGW ISAYNGNTNY    60
AQKLQGRVTM TTDTSTSTAY MELRSLRSDD TAVYYCARDL GWPDDYWGQG TLVTVSS      117

SEQ ID NO: 36           moltype = AA  length = 125
FEATURE                 Location/Qualifiers
REGION                  1..125
                        note = synthetic
source                  1..125
                        mol_type = protein
                        organism = synthetic construct
SEQUENCE: 36
EVQLLESGGG VVRPGGSLRL SCAASGFTFD DYGMSWVRQA PGKGLEWVSG INWNGGSTGY    60
ADSVKGRFTI SRDNSKNTLY LQMNSLRAED TAAYYCAKDR LRYCSSTSCY IPDYWGQGTL   120
VTVSS                                                              125

SEQ ID NO: 37           moltype = AA  length = 128
FEATURE                 Location/Qualifiers
REGION                  1..128
                        note = synthetic
source                  1..128
                        mol_type = protein
                        organism = synthetic construct
SEQUENCE: 37
QVQLVQSGAE VKKPGASVKV SCKASGYTFT SYGISWVRQA PGQGLEWMGW ISAYNGNTNY    60
AQKLQGRVTM TTDTSTSTAY MELRSLRSDD TAVYYCARVG STYDFWSGAY YYYGMDVWGQ   120
GTTVTVSS                                                           128

SEQ ID NO: 38           moltype = AA  length = 106
FEATURE                 Location/Qualifiers
REGION                  1..106
                        note = synthetic
source                  1..106
                        mol_type = protein
                        organism = synthetic construct
SEQUENCE: 38
DIQMTQSPSS LSASVGDRVT ITCQASQDIS NYLNWYQQKP GKAPKLLIYA ASSLQSGVPS    60
RFSGSGSGTD FTLTISSLQP EDFATYYCQQ SYSTPTFGQG TKLEIK                  106

SEQ ID NO: 39           moltype = AA  length = 108
FEATURE                 Location/Qualifiers
REGION                  1..108
                        note = synthetic
source                  1..108
                        mol_type = protein
                        organism = synthetic construct
SEQUENCE: 39
QAVLTQPPSV SVSPGQTASI TCSGDKLGNK NAYWYQQKPG QSPVLVMYQS TRRPSGIPER    60
FSASNSGNTA TLTISGTQAM DEADYYCQAW DSSSGWEVFG GGTKLTVL                108

SEQ ID NO: 40           moltype = AA  length = 108
FEATURE                 Location/Qualifiers
REGION                  1..108
                        note = synthetic
source                  1..108
                        mol_type = protein
                        organism = synthetic construct
SEQUENCE: 40
ETTLTQSPAT LSLSPGERAT LSCGASQSVS SSYLAWYQQK PGLAPRLLIY DASSRATGIP    60
DRFSGSGSGT DFTLTISRLE PEDFAVYYCH QYNNWPRTFG QGTKVEIK                108

SEQ ID NO: 41           moltype = AA  length = 110
FEATURE                 Location/Qualifiers
REGION                  1..110
                        note = synthetic
source                  1..110
                        mol_type = protein
```

```
                        organism = synthetic construct
SEQUENCE: 41
QPVLTQPPSA SGTPGQRVTI SCSGSSSNIG SNYVYWYQQL PGTAPKLLIY RNNQRPSGVP    60
DRFSGSKSGT SASLAISGLR SEDEADYYCA AWDDSLNGVV FGGGTKLTVL              110

SEQ ID NO: 42           moltype = AA   length = 113
FEATURE                 Location/Qualifiers
REGION                  1..113
                        note = synthetic
source                  1..113
                        mol_type = protein
                        organism = synthetic construct
SEQUENCE: 42
DIQMTQSPDS LAVSLGERAT INCKSSQSVL DSSNNKNYVA WFQQKPGQPP KLLIYWASTR    60
ESGVPDRFSG SGSGTDFTLT ISSLQAEDVA VYYCQQYYTT RWTFGQGTKV EIK           113

SEQ ID NO: 43           moltype = AA   length = 107
FEATURE                 Location/Qualifiers
REGION                  1..107
                        note = synthetic
source                  1..107
                        mol_type = protein
                        organism = synthetic construct
SEQUENCE: 43
DIVMTQSPSS LSASVGDRVT ITCRASQGIR NDLGWYQQKP GKAPKLLIYD ASNLETGVPS    60
RFSGSGSGTD FTFTISSLQP EDIATYYCQQ YDNLPLTFGG GTKVEIK                  107

SEQ ID NO: 44           moltype = AA   length = 381
FEATURE                 Location/Qualifiers
REGION                  1..381
                        note = synthetic
source                  1..381
                        mol_type = protein
                        organism = synthetic construct
SEQUENCE: 44
CAGGTCCAGC TGGTACAGTC TGGGGCTGAG GTGAAGAGGC CTGGGTCCTC GGTGAAGGTC    60
TCCTGCAAGG CTTCTGGAGG CACCTTCAGC AGCTATGCTA TCAGCTGGGT GCGACAGGCC    120
CCTGGACAAG GGCTTGAGTG GATGGGAGGG ATCATCCCTA TCTTTGGTAC AGCAAACTAC    180
GCACAGAAGT TCCAGGGCAG AGTCACGATT ACCGCGGACG AATCCACGAG CACAGCCTAC    240
ATGGAGCTGA GCAACCTGAG ATCTGAGGAC ACGGCCGTGT ATTACTGTGC GAGAGGGGAT    300
ATAGCAGCAG CTGGTAGGAA AGGACTGCCC ATCTACTACA TGGACGTCTG GGGCAAAGGG    360
ACCACGGTCA CCGTCTCCTC A                                              381

SEQ ID NO: 45           moltype = DNA   length = 354
FEATURE                 Location/Qualifiers
misc_feature            1..354
                        note = synthetic
source                  1..354
                        mol_type = other DNA
                        organism = synthetic construct
SEQUENCE: 45
caaatccagc tggtacagtc tggggctgag gtgaagaagc ctggggcctc agtgaaggtc    60
tcctgcaagg cttctggtta cacctttacc agctacggta tcagctgggt gcgacaggcc    120
cctggacaag gacttgagtg gatgggatgg atcagcgctt acaatggtaa cacaaactat    180
gcacagaagc tccagggcag agtcaccatg accacagaca catccacgag cacagcctac    240
atggagctga ggagcctgag atctgacgac acggccgtgt attactgtgc gaggtggggt    300
aggtggctgg ctcatgacta ctggggccag gaaccctggt caccgtctct ctca          354

SEQ ID NO: 46           moltype = DNA   length = 363
FEATURE                 Location/Qualifiers
misc_feature            1..363
                        note = synthetic
source                  1..363
                        mol_type = other DNA
                        organism = synthetic construct
SEQUENCE: 46
cagatgcagc tggtgcagtc tggggctgag gtgaagaagc ctgggtcctc ggtgaaggtc    60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagcccaagt    300
ggttattata tttatgatgc ttttgatatc tggggccaag gacaatggtc accgtctct     360
tca                                                                   363

SEQ ID NO: 47           moltype = DNA   length = 351
FEATURE                 Location/Qualifiers
misc_feature            1..351
                        note = synthetic
source                  1..351
```

```
                        mol_type = other DNA
                        organism = synthetic construct
SEQUENCE: 47
caggtccagc tggtgcagtc tggagctgag gtgaagaagc ctggggcctc agtgaaggtc    60
tcctgcaagg cttctggtta cacctttacc agctatggta tcagctgggt gcgacaggcc   120
cctggacaag ggcttgagtg gatgggatgg atcagcgctt acaatggtaa cacaaactat   180
gcacagaagc tccagggcag agtcaccatg accacagaca catccacgag cacagcctac   240
atggagctga ggagcctgag atctgacgac acggccgtgt attactgtgc gagagatctc   300
ggctggccag atgactactg gggccaggga accctggtca ccgtctcctc a            351

SEQ ID NO: 48           moltype = DNA  length = 375
FEATURE                 Location/Qualifiers
misc_feature            1..375
                        note = synthetic
source                  1..375
                        mol_type = other DNA
                        organism = synthetic construct
SEQUENCE: 48
gaagtgcagt tgttggagtc tgggggaggt gtggtacggc ctgggggtc cctgagactc     60
tcctgtgcag cctctggatt cacctttgat gattatggca tgagctgggt ccgccaagct   120
ccagggaagg ggctggagtg ggtctctggt attaattgga tggtggtag cacaggttat   180
gcagactccg tgaagggccg attcaccatc tccagagaca attccaagaa cacgctgtat   240
ctgcaaatga acagcctgag agctgaggac acggctgcgt attactgtgc gaaagatcga   300
ctaagatatt gtagtagtac cagctgctat atccctgact actggggcca gggaaccctg   360
gtcaccgtct cctca                                                    375

SEQ ID NO: 49           moltype = DNA  length = 384
FEATURE                 Location/Qualifiers
misc_feature            1..384
                        note = synthetic
source                  1..384
                        mol_type = other DNA
                        organism = synthetic construct
SEQUENCE: 49
caggtgcagc tggtgcagtc tggagctgag gtgaagaagc ctggggcctc agtgaaggtc    60
tcctgcaagg cttctggtta cacctttacc agctatggta tcagctgggt gcgacaggcc   120
cctggacaag ggcttgagtg gatgggatgg atcagcgctt acaatggtaa cacaaactat   180
gcacagaagc tccagggcag agtcaccatg accacagaca catccacgag cacagcctac   240
atggagctga ggagcctgag atctgacgac acggccgtgt attactgtgc gagagtaggg   300
agcacttacg attttttggag tggcgcctac tactactacg gtatggacgt ctggggccaa   360
gggaccacgg tcaccgtctc ctca                                          384

SEQ ID NO: 50           moltype = DNA  length = 318
FEATURE                 Location/Qualifiers
misc_feature            1..318
                        note = synthetic
source                  1..318
                        mol_type = other DNA
                        organism = synthetic construct
SEQUENCE: 50
gacatccaga tgacccagtc tccatcctcc ctgtctgcat ctgtaggaga cagagtcacc    60
atcacttgcc aggcgagtca ggacattagc aactacttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctacttt tggccagggg   300
accaagctgg agatcaaa                                                 318

SEQ ID NO: 51           moltype = DNA  length = 324
FEATURE                 Location/Qualifiers
misc_feature            1..324
                        note = synthetic
source                  1..324
                        mol_type = other DNA
                        organism = synthetic construct
SEQUENCE: 51
caggcagtgc tgactcagcc accctcagtg tccgtgtccc caggacagac agccagcatc    60
acctgctctg gagataaatt gggaaataaa aatgcttatt ggtatcagca gaagccaggc   120
cagtcccctg tactggtcat gtatcaaagt accagacggc cctcagggat ccctgagcga   180
ttctctgcct ccaactctgg gaacacagcc actctgacca tcagcgggac ccaggctatg   240
gatgaggctg actattactg tcaggcgtgg gacagcagta gtggatggga ggtattcggc   300
ggagggacca agctgaccgt ccta                                          324

SEQ ID NO: 52           moltype = DNA  length = 324
FEATURE                 Location/Qualifiers
misc_feature            1..324
                        note = synthetic
source                  1..324
                        mol_type = other DNA
                        organism = synthetic construct
```

```
SEQUENCE: 52
gaaacgacac tcacgcagtc tccagccacc ctgtctttgt ctccagggga aagagccacc    60
ctctcctgcg gggccagtca gagtgttagc agcagctact tagcctggta ccagcagaaa   120
cctggcctgg cgcccaggct cctcatctat gatgcatcca gcagggccac tggcatccca   180
gacaggttca gtggcagtgg gtctgggaca gacttcactc tcaccatcag cagactggag   240
cctgaagatt ttgcagttta ttactgtcac cagtataata actggcctag gacgttcggc   300
caagggacca aggtggaaat caaa                                           324

SEQ ID NO: 53            moltype = DNA   length = 330
FEATURE                  Location/Qualifiers
misc_feature             1..330
                         note = synthetic
source                   1..330
                         mol_type = other DNA
                         organism = synthetic construct
SEQUENCE: 53
cagcctgtgc tgactcagcc accctcagcg tctgggaccc ccgggcagag ggtcaccatc    60
tcttgttctg gaagcagctc caacatcgga agtaattatg tatactggta ccagcagctc   120
ccaggaacgg ccccccaaact cctcatctat aggaataatc agcggccctc aggggtccct   180
gaccgattct ctggctccaa gtctggcacc tcagcctccc tggccatcag tgggctccgg   240
tccgaggatg aggctgatta ttattgtgca gcatgggatg acagcctgaa tggtgtggta   300
ttcggcggag ggaccaagct gaccgtccta                                     330

SEQ ID NO: 54            moltype = DNA   length = 339
FEATURE                  Location/Qualifiers
misc_feature             1..339
                         note = synthetic
source                   1..339
                         mol_type = other DNA
                         organism = synthetic construct
SEQUENCE: 54
gacatccaga tgacccagtc tccggactcc ctggctgtgt ctctgggcga gagggccacc    60
atcaactgca gtccagcca gagtgttttg gacagctcca acaataaaaa ttatgtcgct   120
tggttccagc agaaaccagg acagcctcct aagctgctca tttactgggc ctctacccgg   180
gaatccgggg tccctgaccg attcagtggc agcggttctg ggacagattt cactctcacc   240
atcagcagcc tgcaggctga agatgtggca gtttattact gtcagcaata ttatactact   300
cggtggacgt tcggccaagg gaccaaggtg gaaatcaaa                           339

SEQ ID NO: 55            moltype = DNA   length = 321
FEATURE                  Location/Qualifiers
misc_feature             1..321
                         note = synthetic
source                   1..321
                         mol_type = other DNA
                         organism = synthetic construct
SEQUENCE: 55
gacatcgtga tgacccagtc tccatcctcc ctgtctgcat ctgtaggaga cagagtcacc    60
atcacttgcc gggcaagtca gggcattaga aatgatttag gctggtatca gcaaaaacca   120
gggaaagccc ctaaactcct gatctacgat gcatccaatt tggaaacagg ggtcccatca   180
aggttcagtg gaagtggatc tgggacagat tttactttca ccatcagcag cctgcagcct   240
gaagatattg caacatatta ctgtcaacag tatgataacc tcccgctcac tttcggcgga   300
gggaccaagg tggagatcaa a                                              321

SEQ ID NO: 56            moltype = AA   length = 8
FEATURE                  Location/Qualifiers
REGION                   1..8
                         note = synthetic
source                   1..8
                         mol_type = protein
                         organism = synthetic construct
SEQUENCE: 56
GFTFSRHG                                                               8

SEQ ID NO: 57            moltype = AA   length = 8
FEATURE                  Location/Qualifiers
REGION                   1..8
                         note = synthetic
source                   1..8
                         mol_type = protein
                         organism = synthetic construct
SEQUENCE: 57
IWYDGRNK                                                               8

SEQ ID NO: 58            moltype = AA   length = 17
FEATURE                  Location/Qualifiers
REGION                   1..17
                         note = synthetic
source                   1..17
                         mol_type = protein
```

```
                        organism = synthetic construct
SEQUENCE: 58
AREGITMVRG VIPLFDY                                                      17

SEQ ID NO: 59           moltype = AA  length = 8
FEATURE                 Location/Qualifiers
REGION                  1..8
                        note = synthetic
source                  1..8
                        mol_type = protein
                        organism = synthetic construct
SEQUENCE: 59
GFTFSRYG                                                                 8

SEQ ID NO: 60           moltype = AA  length = 8
FEATURE                 Location/Qualifiers
REGION                  1..8
                        note = synthetic
source                  1..8
                        mol_type = protein
                        organism = synthetic construct
SEQUENCE: 60
IWYDGSYK                                                                 8

SEQ ID NO: 61           moltype = AA  length = 13
FEATURE                 Location/Qualifiers
REGION                  1..13
                        note = synthetic
source                  1..13
                        mol_type = protein
                        organism = synthetic construct
SEQUENCE: 61
ARFGILTGYY FDY                                                          13

SEQ ID NO: 62           moltype = AA  length = 8
FEATURE                 Location/Qualifiers
REGION                  1..8
                        note = synthetic
source                  1..8
                        mol_type = protein
                        organism = synthetic construct
SEQUENCE: 62
GFTFSSYA                                                                 8

SEQ ID NO: 63           moltype = AA  length = 8
FEATURE                 Location/Qualifiers
REGION                  1..8
                        note = synthetic
source                  1..8
                        mol_type = protein
                        organism = synthetic construct
SEQUENCE: 63
ISGSGYST                                                                 8

SEQ ID NO: 64           moltype = AA  length = 13
FEATURE                 Location/Qualifiers
REGION                  1..13
                        note = synthetic
source                  1..13
                        mol_type = protein
                        organism = synthetic construct
SEQUENCE: 64
AKGKVGPTYA FDL                                                          13

SEQ ID NO: 65           moltype = AA  length = 8
FEATURE                 Location/Qualifiers
REGION                  1..8
                        note = synthetic
source                  1..8
                        mol_type = protein
                        organism = synthetic construct
SEQUENCE: 65
GFTFSSYG                                                                 8

SEQ ID NO: 66           moltype = AA  length = 8
FEATURE                 Location/Qualifiers
REGION                  1..8
                        note = synthetic
source                  1..8
```

```
                        mol_type = protein
                        organism = synthetic construct
SEQUENCE: 66
IWYDGSNK                                                              8

SEQ ID NO: 67           moltype = AA   length = 9
FEATURE                 Location/Qualifiers
REGION                  1..9
                        note = synthetic
source                  1..9
                        mol_type = protein
                        organism = synthetic construct
SEQUENCE: 67
AREGRGMDV                                                             9

SEQ ID NO: 68           moltype = AA   length = 8
FEATURE                 Location/Qualifiers
REGION                  1..8
                        note = synthetic
source                  1..8
                        mol_type = protein
                        organism = synthetic construct
SEQUENCE: 68
GFTFSTYG                                                              8

SEQ ID NO: 69           moltype = AA   length = 8
FEATURE                 Location/Qualifiers
REGION                  1..8
                        note = synthetic
source                  1..8
                        mol_type = protein
                        organism = synthetic construct
SEQUENCE: 69
IWYDGYNK                                                              8

SEQ ID NO: 70           moltype = AA   length = 13
FEATURE                 Location/Qualifiers
REGION                  1..13
                        note = synthetic
source                  1..13
                        mol_type = protein
                        organism = synthetic construct
SEQUENCE: 70
EGWFGKLLSA LDI                                                       13

SEQ ID NO: 71           moltype = AA   length = 7
FEATURE                 Location/Qualifiers
REGION                  1..7
                        note = synthetic
source                  1..7
                        mol_type = protein
                        organism = synthetic construct
SEQUENCE: 71
SGHSSYA                                                               7

SEQ ID NO: 72           moltype = AA   length = 7
FEATURE                 Location/Qualifiers
REGION                  1..7
                        note = synthetic
source                  1..7
                        mol_type = protein
                        organism = synthetic construct
SEQUENCE: 72
LNSDGSH                                                               7

SEQ ID NO: 73           moltype = AA   length = 9
FEATURE                 Location/Qualifiers
REGION                  1..9
                        note = synthetic
source                  1..9
                        mol_type = protein
                        organism = synthetic construct
SEQUENCE: 73
QTWGTGMLC                                                             9

SEQ ID NO: 74           moltype = AA   length = 9
FEATURE                 Location/Qualifiers
REGION                  1..9
                        note = synthetic
```

```
source                    1..9
                          mol_type = protein
                          organism = synthetic construct
SEQUENCE: 74
QTWGTGMLF                                                                    9

SEQ ID NO: 75             moltype = AA  length = 9
FEATURE                   Location/Qualifiers
REGION                    1..9
                          note = synthetic
source                    1..9
                          mol_type = protein
                          organism = synthetic construct
SEQUENCE: 75
QTWGTGMLW                                                                    9

SEQ ID NO: 76             moltype = AA  length = 8
FEATURE                   Location/Qualifiers
REGION                    1..8
                          note = synthetic
source                    1..8
                          mol_type = protein
                          organism = synthetic construct
SEQUENCE: 76
QTWGTGCC                                                                     8

SEQ ID NO: 77             moltype = AA  length = 9
FEATURE                   Location/Qualifiers
REGION                    1..9
                          note = synthetic
source                    1..9
                          mol_type = protein
                          organism = synthetic construct
SEQUENCE: 77
SGSVSTSYN                                                                    9

SEQ ID NO: 78             moltype =   length =
SEQUENCE: 78
000

SEQ ID NO: 79             moltype = AA  length = 9
FEATURE                   Location/Qualifiers
REGION                    1..9
                          note = synthetic
source                    1..9
                          mol_type = protein
                          organism = synthetic construct
SEQUENCE: 79
VLYMGSGII                                                                    9

SEQ ID NO: 80             moltype = AA  length = 9
FEATURE                   Location/Qualifiers
REGION                    1..9
                          note = synthetic
source                    1..9
                          mol_type = protein
                          organism = synthetic construct
SEQUENCE: 80
SGSVSTSYY                                                                    9

SEQ ID NO: 81             moltype = AA  length = 10
FEATURE                   Location/Qualifiers
REGION                    1..10
                          note = synthetic
source                    1..10
                          mol_type = protein
                          organism = synthetic construct
SEQUENCE: 81
VLYMGSGTCC                                                                  10

SEQ ID NO: 82             moltype = AA  length = 7
FEATURE                   Location/Qualifiers
REGION                    1..7
                          note = synthetic
source                    1..7
                          mol_type = protein
                          organism = synthetic construct
SEQUENCE: 82
SGHSSYI                                                                      7
```

```
SEQ ID NO: 83          moltype = AA   length = 7
FEATURE                Location/Qualifiers
REGION                 1..7
                       note = synthetic
source                 1..7
                       mol_type = protein
                       organism = synthetic construct
SEQUENCE: 83
LEGSGSY                                                                   7

SEQ ID NO: 84          moltype = AA   length = 11
FEATURE                Location/Qualifiers
REGION                 1..11
                       note = synthetic
source                 1..11
                       mol_type = protein
                       organism = synthetic construct
SEQUENCE: 84
ETWDSNTPHA V                                                             11

SEQ ID NO: 85          moltype = AA   length = 6
FEATURE                Location/Qualifiers
REGION                 1..6
                       note = synthetic
source                 1..6
                       mol_type = protein
                       organism = synthetic construct
SEQUENCE: 85
QGIRND                                                                    6

SEQ ID NO: 86          moltype =      length =
SEQUENCE: 86
000

SEQ ID NO: 87          moltype = AA   length = 9
FEATURE                Location/Qualifiers
REGION                 1..9
                       note = synthetic
source                 1..9
                       mol_type = protein
                       organism = synthetic construct
SEQUENCE: 87
LQDYNYPFT                                                                 9

SEQ ID NO: 88          moltype = AA   length = 124
FEATURE                Location/Qualifiers
REGION                 1..124
                       note = synthetic
source                 1..124
                       mol_type = protein
                       organism = synthetic construct
SEQUENCE: 88
QVQLVESGGG VVQPGRSLRL SCAASGFTFS RHGMHWVRQA PGKGLEWVAV IWYDGRNKYY         60
ADSVKGRFTI SRDNSKNTLY LQMNSLRVED TAVYYCAREG ITMVRGVIPL FDYWGQGTLV        120
TVSS                                                                    124

SEQ ID NO: 89          moltype = AA   length = 124
FEATURE                Location/Qualifiers
REGION                 1..124
                       note = synthetic
source                 1..124
                       mol_type = protein
                       organism = synthetic construct
SEQUENCE: 89
QVQLVESGGG VVQPGRSLRL SCAASGFTFS RHGMHWVRQA PGKGLEWVAV IWYDGRNKYY         60
ADSVKGRFTI SRDNSKNTLY LQMNSLRVED TAVYYCAREG ITMVRGVIPL FDYWGQGTLV        120
TVSS                                                                    124

SEQ ID NO: 90          moltype = AA   length = 124
FEATURE                Location/Qualifiers
REGION                 1..124
                       note = synthetic
source                 1..124
                       mol_type = protein
                       organism = synthetic construct
SEQUENCE: 90
QVQLVESGGG VVQPGRSLRL SCAASGFTFS RHGMHWVRQA PGKGLEWVAV IWYDGRNKYY         60
ADSVKGRFTI SRDNSKNTLY LQMNSLRVED TAVYYCAREG ITMVRGVIPL FDYWGQGTLV        120
```

```
                                                     -continued

TVSS                                                                   124

SEQ ID NO: 91           moltype = AA  length = 120
FEATURE                 Location/Qualifiers
REGION                  1..120
                        note = synthetic
source                  1..120
                        mol_type = protein
                        organism = synthetic construct
SEQUENCE: 91
QVQLVESGGG VVQPGRSLRL SCAASGFTFS RYGMHWVRQA PGKGLEWVAV IWYDGSYKYY        60
ADSIKGRFTV SRDNSKNTLY LQMNSLRAED TALYYCARFG ILTGYYFDYW GQGTLVTVSS       120

SEQ ID NO: 92           moltype = AA  length = 124
FEATURE                 Location/Qualifiers
REGION                  1..124
                        note = synthetic
source                  1..124
                        mol_type = protein
                        organism = synthetic construct
SEQUENCE: 92
QVQLVESGGG VVQPGRSLRL SCAASGFTFS RHGMHWVRQA PGKGLEWVAV IWYDGRNKYY        60
ADSVKGRFTI SRDNSKNTLY LQMNSLRVED TAVYYCAREG ITMVRGVIPL FDYWGQGTLV      120
TVSS                                                                   124

SEQ ID NO: 93           moltype = AA  length = 120
FEATURE                 Location/Qualifiers
REGION                  1..120
                        note = synthetic
source                  1..120
                        mol_type = protein
                        organism = synthetic construct
SEQUENCE: 93
EVQLLESGGG LVQPGGSLRL SCAASGFTFS SYAMSWVRQA PGEGLEWVSG ISGSGYSTYS        60
ADSVKGRFTI FKDNSKNTLY LQINSLRAED TAVYYCAKGK VGPTYAFDLW GQGTMVTVSS      120

SEQ ID NO: 94           moltype = AA  length = 116
FEATURE                 Location/Qualifiers
REGION                  1..116
                        note = synthetic
source                  1..116
                        mol_type = protein
                        organism = synthetic construct
SEQUENCE: 94
QVQLVESGGG VVQPGRSLRL SCAASGFTFS SYGMHWVRQA PGKGLEWVAV IWYDGSNKYY        60
ADSVKGRFTI SRDNSKNTLY LQMNSLRAED TAVYYCAREG RGMDVWGQGT TVTVSS          116

SEQ ID NO: 95           moltype = AA  length = 122
FEATURE                 Location/Qualifiers
REGION                  1..122
                        note = synthetic
source                  1..122
                        mol_type = protein
                        organism = synthetic construct
SEQUENCE: 95
QVQLVESGGG VVQPGRSLRL SCAASGFTFS TYGIHWVRQA PGKGLEWVAV IWYDGYNKYY        60
VDSVKGRFTI SRDNSENTVY LQMNSLRTED TAVYYCAREG WFGKLLSALD IWGQGTMVTV      120
SS                                                                     122

SEQ ID NO: 96           moltype = AA  length = 112
FEATURE                 Location/Qualifiers
REGION                  1..112
                        note = synthetic
source                  1..112
                        mol_type = protein
                        organism = synthetic construct
SEQUENCE: 96
QFVLTQSPSA SASLGASVKL TCTLSSGHSS YAIAWHHQQP EKGPRYLMKL NSDGSHSKGD        60
GIPDRFSGSS SGAERYLTIS SLQSEDEADY YCQTWGTGML CFGGGTQLTA LR              112

SEQ ID NO: 97           moltype = AA  length = 111
FEATURE                 Location/Qualifiers
REGION                  1..111
                        note = synthetic
source                  1..111
                        mol_type = protein
                        organism = synthetic construct
SEQUENCE: 97
QFVLTQSPSA SASLGASVKL TCTLSSGHSS YAIAWHHQQP EKGPRYLMKL NSDGSHSKGD        60
```

```
GIPDRFSGSS SGAERYLTIS SLQSEDEADY YCQTWGTGML FGGGTQLTAL R            111

SEQ ID NO: 98           moltype = AA   length = 112
FEATURE                 Location/Qualifiers
REGION                  1..112
                        note = synthetic
source                  1..112
                        mol_type = protein
                        organism = synthetic construct
SEQUENCE: 98
QPVLTQSPSA SASLGASVKL TCTLSSGHSS YAIAWHHQQP EKGPRYLMKL NSDGHSKGD     60
GIPDRFSGSS SGAERYLTIS SLQSEDEADY YCQTWGTGML WFGGGTQLTA LR           112

SEQ ID NO: 99           moltype = AA   length = 111
FEATURE                 Location/Qualifiers
REGION                  1..111
                        note = synthetic
source                  1..111
                        mol_type = protein
                        organism = synthetic construct
SEQUENCE: 99
QVVLTQSPPA SASLGASVKL TCTLSSGHSS YAIAWHQQQP EKGPRYLMKL NSDGHSKGD     60
GIPDRFSGSS SGAERYLTIS SLQSEDEADY YCQTWGTGCC FGGGTQLTAL R            111

SEQ ID NO: 100          moltype = AA   length = 109
FEATURE                 Location/Qualifiers
REGION                  1..109
                        note = synthetic
source                  1..109
                        mol_type = protein
                        organism = synthetic construct
SEQUENCE: 100
QTVVTQESSF SVSPGGTVTL TCGLSSGSVS TSYNPSWYQQ TPGQAPRTLI YSTNTRSSGV    60
PDRFSGSILG NKAALTITGA QADDESDYYC VLYMGSIIF GSGTKVTVL                109

SEQ ID NO: 101          moltype = AA   length = 111
FEATURE                 Location/Qualifiers
REGION                  1..111
                        note = synthetic
source                  1..111
                        mol_type = protein
                        organism = synthetic construct
SEQUENCE: 101
QTVVTQEPSF SVSPGGTVTL TCGLSSGSVS TSYYPSWYQQ TPGQAPRTLI YSTNTRSSGV    60
PERFSGSILG NKAALTITGA QADDESDYYC VLYMGSGTCC FGGGTQLTAL R            111

SEQ ID NO: 102          moltype = AA   length = 113
FEATURE                 Location/Qualifiers
REGION                  1..113
                        note = synthetic
source                  1..113
                        mol_type = protein
                        organism = synthetic construct
SEQUENCE: 102
QPVLTQSSSA SASLGSSVKL TCTLSSGHSS YIIAWHQQQP GKAPRYLMKL EGSGSYNKGS    60
GVPDRFSGSS SGADRYLTIS NLQFEDEADY YCETWDSNTP HAVFGGGTQL TAL          113

SEQ ID NO: 103          moltype = AA   length = 107
FEATURE                 Location/Qualifiers
REGION                  1..107
                        note = synthetic
source                  1..107
                        mol_type = protein
                        organism = synthetic construct
SEQUENCE: 103
VIQMTQSPSS LSASVGDRVT ITCRASQGIR NDLGWYLQKP GKAPELLIYP ASSLQSGVPS    60
RFSGSGSGTD FTLTISSLQP EDFATYYCLQ DYNYPFTFGQ GTKLEIK                 107

SEQ ID NO: 104          moltype = AA   length = 372
FEATURE                 Location/Qualifiers
REGION                  1..372
                        note = synthetic
source                  1..372
                        mol_type = protein
                        organism = synthetic construct
SEQUENCE: 104
CAGGTCCAAC TCGTCGAGAG CGGAGGAGGA GTCGTCCAAC CCGGAAGGAG CTTGCGGCTA    60
TCATGCGCGG CATCCGGCTT CACATTTTCC CGGCACGGGA TGCACTGGGT CAGGCAAGCA   120
CCCGGCAAGG GGCTAGAATG GGTCGCGGTC ATCTGGTATG ATGGAAGGAA CAAATACTAT   180
```

```
GCCGACTCAG TCAAGGGGCG ATTTACAATT TCGCGAGACA ACTCCAAGAA TACGCTATAC    240
CTGCAAATGA ACTCGCTGAG GGTCGAGGAC ACGGCGGTTT ATTACTGCGC GAGGGAGGGG    300
ATAACTATGG TCAGAGGAGT CATTCCGCTA TTTGACTATT GGGGGCAGGG TACCTTAGTC    360
ACGGTCTCGA GC                                                       372

SEQ ID NO: 105          moltype = DNA   length = 372
FEATURE                 Location/Qualifiers
misc_feature            1..372
                        note = synthetic
source                  1..372
                        mol_type = other DNA
                        organism = synthetic construct
SEQUENCE: 105
caggtccaac tcgtcgagag cggaggagga gtcgtccaac ccggaaggag cttgcggcta    60
tcatgcgcgg catccggctt cacatttttcc cggcacggga tgcactgggt caggcaagca    120
cccggcaagg ggctagaatg ggtcgcggtc atctggtatg atggaaggaa caaatactat    180
gccgactcag tcaaggggcg atttacaatt tcgcgagaca actccaagaa tacgctatac    240
ctgcaaatga actcgctgag ggtcgaggac acggcggttt attactgcgc gagggagggg    300
ataactatgg tcagaggagt cattccgcta tttgactatt gggggcaggg taccttagtc    360
acggtctcga gc                                                       372

SEQ ID NO: 106          moltype = DNA   length = 372
FEATURE                 Location/Qualifiers
misc_feature            1..372
                        note = synthetic
source                  1..372
                        mol_type = other DNA
                        organism = synthetic construct
SEQUENCE: 106
caggtccaac tcgtcgagag cggaggagga gtcgtccaac ccggaaggag cttgcggcta    60
tcatgcgcgg catccggctt cacatttttcc cggcacggga tgcactgggt caggcaagca    120
cccggcaagg ggctagaatg ggtcgcggtc atctggtatg atggaaggaa caaatactat    180
gccgactcag tcaaggggcg atttacaatt tcgcgagaca actccaagaa tacgctatac    240
ctgcaaatga actcgctgag ggtcgaggac acggcggttt attactgcgc gagggagggg    300
ataactatgg tcagaggagt cattccgcta tttgactatt gggggcaggg taccttagtc    360
acggtctcga gc                                                       372

SEQ ID NO: 107          moltype = DNA   length = 360
FEATURE                 Location/Qualifiers
misc_feature            1..360
                        note = synthetic
source                  1..360
                        mol_type = other DNA
                        organism = synthetic construct
SEQUENCE: 107
caggtccaac tcgttgaatc cggggggggga gtcgtccaac cggggagaag cctgcggcta    60
agctgcgcgg cttcgggatt cacattctct cgatacggga tgcactgggt caggcaagca    120
ccggggaagg gcttggaatg ggtcgccgtc atatggtacg acggatcata taaatattat    180
gctgactcta taagggggcg attcacggtt agccgagaca actccaaaaa cacgctatac    240
ctgcaaatga actcactgcg agctgaagat acggcgctat attattgcgc ccgattcgga    300
atcctgaccg gatattattt tgactactgg gggcagggta ccctagtcac ggtctcgagc    360

SEQ ID NO: 108          moltype = DNA   length = 372
FEATURE                 Location/Qualifiers
misc_feature            1..372
                        note = synthetic
source                  1..372
                        mol_type = other DNA
                        organism = synthetic construct
SEQUENCE: 108
caggtccaac tcgtcgagag cggaggagga gtcgtccaac ccggaaggag cttgcggcta    60
tcatgcgcgg catccggctt cacatttttcc cggcacggga tgcactgggt caggcaagca    120
cccggcaagg ggctagaatg ggtcgcggtc atctggtatg atggaaggaa caaatactat    180
gccgactcag tcaaggggcg atttacaatt tcgcgagaca actccaagaa tacgctatac    240
ctgcaaatga actcgctgag ggtcgaggac acggcggttt attactgcgc gagggagggg    300
ataactatgg tcagaggagt cattccgcta tttgactatt gggggcaggg taccttagtc    360
acggtctcga gc                                                       372

SEQ ID NO: 109          moltype = DNA   length = 360
FEATURE                 Location/Qualifiers
misc_feature            1..360
                        note = synthetic
source                  1..360
                        mol_type = other DNA
                        organism = synthetic construct
SEQUENCE: 109
gaagtccaac tgctggaatc gggcggggggg ctggtccaac ccggaggatc attgaggcta    60
tcatgcgccg cttccggctt tacatttagc tcatacgcaa tgtcatgggt ccgacaagct    120
ccgggggagg gactggaatg ggtctctggg atttcgggct ctggatactc cacatatagc    180
```

```
gcggactcag tcaaggggag attcacgatt tttaaggata actccaagaa tacattatat    240
ctgcaaataa actcgctgag ggcggaggat accgccgttt attactgcgc caaagggaaa    300
gtcgggccaa cttacgcatt cgacctatgg gggcagggta ccatggtcac ggtctcgagc    360
```

SEQ ID NO: 110                 moltype = DNA   length = 348
FEATURE                    Location/Qualifiers
misc_feature         1..348
                           note = synthetic
source                     1..348
                           mol_type = other DNA
                           organism = synthetic construct
SEQUENCE: 110
```
caagtgcaac tcgtggaatc gggcggaggg gtggtgcaac cgggaagatc actgcgacta    60
tcatgcgccg catcgggatt tacatttagc agctacggga tgcactgggt ccgccaagca    120
cccggaaaag ggctgaatgg ggtcgcggtg atttggtacg atggctcgaa taaatactat    180
gctgactcgg tgaagggccg attcacaatc tcgcgggaca actccaaaaa cacactatat    240
ctgcaaatga actcactgcg ggcggaggat accgcgtat attactgcgc gagggagggg    300
cgcggaatgg atgtatgggg gcagggtacc acggtgaccg tctcgagc    348
```

SEQ ID NO: 111                 moltype = DNA   length = 366
FEATURE                    Location/Qualifiers
misc_feature         1..366
                           note = synthetic
source                     1..366
                           mol_type = other DNA
                           organism = synthetic construct
SEQUENCE: 111
```
caggtgcagc tggtggagtc tgggggaggc gtggtccagc ctggggggtc cctgagactc    60
tcctgtgcag catctggatt caccttcagt acctatggca tacactgggt ccgccaggct    120
ccaggcaagg ggctggagtg ggtggcagtt atatggtatg atggatataa taaatactat    180
gtagactccg tgaagggccg attcaccatc tccagagaca attccgagaa cacggtgtat    240
ctgcagatga acagcctgag aaccgaggac acggctgttt attactgtgc gagagaagga    300
tggttcggga aattattatc cgctcttgat atctggggcc aagggacaat ggtcaccgtc    360
tcttca    366
```

SEQ ID NO: 112                 moltype = DNA   length = 408
FEATURE                      Location/Qualifiers
misc_feature         1..408
                           note = synthetic
source                     1..408
                           mol_type = other DNA
                           organism = synthetic construct
SEQUENCE: 112
```
gcggccgcca tgaattttgg actgaggctg attttcctgg tgctgaccct gaaaggcgtc    60
cagtgtcaat ttgtgctgac gcaatcgcca tcgctagtg catcactggg ggcgagcgtt    120
aaattgacat gcacgctatc gagcggacac tcatcatatg ccattgcatg caccaccaa    180
caaccggaaa aggggccacg atatctaatg aagctaaact ctgacggatc gcattcgaaa    240
ggggatggga ttcccgaccg attctcggga agcagcagcg gagctgaaag atatttaacg    300
atatcatcgc tgcaatcgga ggatgaagct gactactact gccaaacttg gggaacgggg    360
atgctatgct tcggaggagg cacacaattg acggcccttg gacaaccg    408
```

SEQ ID NO: 113                 moltype = DNA   length = 405
FEATURE                      Location/Qualifiers
misc_feature         1..405
                           note = synthetic
source                     1..405
                           mol_type = other DNA
                           organism = synthetic construct
SEQUENCE: 113
```
gcggccgcca tgaattttgg actgaggctg attttcctgg tgctgaccct gaaaggcgtc    60
cagtgtcaat ttgtactgac gcaaagccca agcgcgagcg catcgctggg agcatccgtc    120
aagctcacat gcacgctatc atcgggccat tcaagctatg ccatagcatg gcatcaccaa    180
caaccggaga agggaccctcg atatctgatg aagctgaata gcgacggctc ccactcaaag    240
ggggacggaa tcccggatag attttcgggc tcatcagagc ggagcg atatctcacg    300
atctctagcc tgcaaagcga ggatgaggcc gactactact gccaaacatg ggggacggga    360
atgctattcg gaggaggcac gcaactgacg gcgctgggc aacca    405
```

SEQ ID NO: 114                 moltype = DNA   length = 408
FEATURE                      Location/Qualifiers
misc_feature         1..408
                           note = synthetic
source                     1..408
                           mol_type = other DNA
                           organism = synthetic construct
SEQUENCE: 114
```
gcggccgcca tgaattttgg actgaggctg attttcctgg tgctgaccct gaaaggcgtc    60
cagtgtcaat ttgtgctgac gcaatcacca tcggcttcgg cgagcctggg ggcatctgtc    120
aagctgacat gcacgctgag ctccgggcat tcatcatatg ccatcgcatg gcatcaccaa    180
caacccgaga agggaccacg atatctcatg aagctaaact ccgacggatc gcattcgaag    240
```

```
ggggatggaa tacccgaccg attttcggga tcatcgagcg gggcggagag atatttgacg    300
atctcctctc tgcaaagcga ggacgaggcg gactactatt gccaaacctg gggcacggga    360
atgctatggt ttggaggagg cacacaactg acgcgctggg ccaaccg                  408

SEQ ID NO: 115          moltype = DNA   length = 405
FEATURE                 Location/Qualifiers
misc_feature            1..405
                        note = synthetic
source                  1..405
                        mol_type = other DNA
                        organism = synthetic construct
SEQUENCE: 115
gcggccgcca tgaattttgg actgaggctg attttcctgg tgctgaccct gaaaggcgtc    60
cagtgtcaag tagtcctgac tcaaagcccc ccggcgagcg catcattggg ggcgagcgtc    120
aagctgacat gcacgctatc gagcgggcac tctagctacg cgatagcatg gcaccaacaa    180
caaccggaaa agggacccg atacttgatg aaattaaata gcgacggatc gcactctaag    240
ggagacggaa tacctgatag attagcgggg agctcatcgg gggcggagag atacttgacg   300
attagctcac tgcaatcgga ggatgaggcg gactactatt gccaaacatg ggggacggga   360
tgctgcttcg gaggaggcac gcaactgacc gcattggac aacca                    405

SEQ ID NO: 116          moltype = DNA   length = 402
FEATURE                 Location/Qualifiers
misc_feature            1..402
                        note = synthetic
source                  1..402
                        mol_type = other DNA
                        organism = synthetic construct
SEQUENCE: 116
gcggccgcca tgaattttgg actgaggctg attttcctgg tgctgaccct gaaaggcgtc    60
cagtgtcaaa ccgtggtgac acaagaatca agttttagcg tatcgccggg agggacgggtg   120
acgctgacct gcgggctatc atctggatcg gtatcaacat cctacaatcc gagctggtat   180
caacaaacgc ccggacaagc gccacgaacc ctgatatatt cgacaaatac ccgatcatct   240
ggggtgccgg atagattttc cggctcgatt ctgggaaaca aggctgcgct gacgataacc   300
ggagctcaag ccgacgatga gagcgattat tattgcgtgc tatacatggg gagcgggatt   360
atattcggat ctgaacgaa agtcacggtg ctaggacaac cg                       402

SEQ ID NO: 117          moltype = DNA   length = 405
FEATURE                 Location/Qualifiers
misc_feature            1..405
                        note = synthetic
source                  1..405
                        mol_type = other DNA
                        organism = synthetic construct
SEQUENCE: 117
gcggccgcca tgaattttgg actgaggctg attttcctgg tgctgaccct gaaaggcgtc    60
cagtgtcaaa cggtcgtcac gcaagagcca tccttctcgg tctcgccggg ggggacggtc    120
acactgacat gcgggctgag ctcgggatcg gtctcaacga gctactaccc gagctggtat   180
caacaaacac cggggcaagc accgcgacg ctgatatatt ccacaaatac acggagctcc    240
ggtgtcccgg agagattctc gggatcaata ctggggaaca aggcggctct gacgataacc   300
ggagcccaag cggatgacga atcggactat tactgcgtcc tatacatggg ctccggcaca   360
tgctgctttg gaggaggcac acaactgacg gcgctggac aacct                    405

SEQ ID NO: 118          moltype = DNA   length = 414
FEATURE                 Location/Qualifiers
misc_feature            1..414
                        note = synthetic
source                  1..414
                        mol_type = other DNA
                        organism = synthetic construct
SEQUENCE: 118
gcggccgcca tgaattttgg actgaggctg attttcctgg tgctgaccct gaaaggcgtc    60
cgtgtcagc cggttttgac gcaatctagc agcgcatccg ctagtcttgg aagctccgtg    120
aagctgacat gcacactatc atcggggcat tcctcctaca taattgcatg gcatcaacaa   180
caaccggca aggccccgag atacttaatg aaactggaag gatcggggatc atataacaaa   240
ggatcggggg tgccggatag atttagcgga tctagctctg ggctgaccgg atacctgacg   300
atctctaatc tgcaatttga ggacgaggcc gattactact gcgaaacatg ggatagcaac   360
accccacacg cggtatttgg aggaggcacc caattgaccg cgctaggcca acca          414

SEQ ID NO: 119          moltype = DNA   length = 321
FEATURE                 Location/Qualifiers
misc_feature            1..321
                        note = synthetic
source                  1..321
                        mol_type = other DNA
                        organism = synthetic construct
SEQUENCE: 119
gtcatccaga tgacccagtc tccatcctcc ctgtctgcat ctgtaggaga cagagtcacc    60
atcacttgcc gggcaagtca ggcattaga aatgattag ctggtatct gcagaaacca      120
gggaaagccc ctgagctcct gatctatcct gcatccagtt tacaaagtgg ggtcccgtca   180
```

```
aggttcagcg gcagtggatc tggcacagat ttcactctca ccatcagcag cctgcagcct    240
gaagattttg caacttatta ctgtctacaa gattacaatt acccgttcac ttttggccag    300
gggaccaagc tggagatcaa a                                              321

SEQ ID NO: 120          moltype = AA   length = 327
FEATURE                 Location/Qualifiers
REGION                  1..327
                        note = synthetic
source                  1..327
                        mol_type = protein
                        organism = synthetic construct
SEQUENCE: 120
ASTKGPSVFP LAPCSRSTSE STAALGCLVK DYFPEPVTVS WNSGALTSGV HTFPAVLQSS     60
GLYSLSSVVT VPSSSLGTKT YTCNVDHKPS NTKVDKRVES KYGPPCPSCP APEFLGGPSV    120
FLFPPKPKDT LMISRTPEVT CVVVDVSQED PEVQFNWYVD GVEVHNAKTK PREEQFNSTY    180
RVVSVLTVLH QDWLNGKEYK CKVSNKGLPS SIEKTISKAK GQPREPQVYT LPPSQEEMTK    240
NQVSLTCLVK GFYPSDIAVE WESNGQPENN YKTTPPVLDS DGSFFLYSRL TVDKSRWQEG    300
NVFSCSVMHE ALHNHYTQKS LSLSLGK                                        327

SEQ ID NO: 121          moltype = AA   length = 326
FEATURE                 Location/Qualifiers
REGION                  1..326
                        note = synthetic
source                  1..326
                        mol_type = protein
                        organism = synthetic construct
SEQUENCE: 121
ASTKGPSVFP LAPCSRSTSE STAALGCLVK DYFPEPVTVS WNSGALTSGV HTFPAVLQSS     60
GLYSLSSVVT VPSSNFGTQT YTCNVDHKPS NTKVDKTVER KCCVECPPCP APPVAGPSVF    120
LFPPKPKDTL MISRTPEVTC VVVDVSHEDP EVQFNWYVDG VEVHNAKTKP REEQFNSTFR    180
VVSVLTVVHQ DWLNGKEYKC KVSNKGLPAP IEKTISKTKG QPREPQVYTL PPSREEMTKN    240
QVSLTCLVKG FYPSDISVEW ESNGQPENNY KTTPPMLDSD GSFFLYSKLT VDKSRWQQGN    300
VFSCSVMHEA LHNHYTQKSL SLSPGK                                         326

SEQ ID NO: 122          moltype = AA   length = 106
FEATURE                 Location/Qualifiers
REGION                  1..106
                        note = synthetic
source                  1..106
                        mol_type = protein
                        organism = synthetic construct
SEQUENCE: 122
GQPKANPTVT LFPPSSEELQ ANKATLVCLI SDFYPGAVTV AWKADGSPVK AGVETTKPSK     60
QSNNKYAASS YLSLTPEQWK SHRSYSCQVT HEGSTVEKTV APTECS                   106

SEQ ID NO: 123          moltype = AA   length = 106
FEATURE                 Location/Qualifiers
REGION                  1..106
                        note = synthetic
source                  1..106
                        mol_type = protein
                        organism = synthetic construct
SEQUENCE: 123
GQPKAAPSVT LFPPSSEELQ ANKATLVCLI SDFYPGAVTV AWKADSSPVK AGVETTTPSK     60
QSNNKYAASS YLSLTPEQWK SHRSYSCQVT HEGSTVEKTV APTECS                   106

SEQ ID NO: 124          moltype = AA   length = 107
FEATURE                 Location/Qualifiers
REGION                  1..107
                        note = synthetic
source                  1..107
                        mol_type = protein
                        organism = synthetic construct
SEQUENCE: 124
RTVAAPSVFI FPPSDEQLKS GTASVVCLLN NFYPREAKVQ WKVDNALQSG NSQESVTEQD     60
SKDSTYSLSS TLTLSKADYE KHKVYACEVT HQGLSSPVTK SFNRGEC                  107

SEQ ID NO: 125          moltype = AA   length = 162
FEATURE                 Location/Qualifiers
REGION                  1..162
                        note = synthetic
source                  1..162
                        mol_type = protein
                        organism = synthetic construct
SEQUENCE: 125
THRTGLRSPD IPQDWVSFLR SFGQLTLCPR NGTVTGKWRG SHVVGLLTTL NFGDGPDRNK     60
TRTFQATVLG SQMGLKGSSA GQLVLITARV TTERTAGTCL YFSAVPGILP SSQPPISCSE    120
EGAGNATLSP RMGEECVSVW SHEGLVLTKL LTSEELALCG SR                       162
```

```
SEQ ID NO: 126            moltype = AA  length = 161
FEATURE                   Location/Qualifiers
REGION                    1..161
                          note = synthetic
source                    1..161
                          mol_type = protein
                          organism = synthetic construct
SEQUENCE: 126
THTTGLRSPD IPQDWVSFLR SFGQLSLCPM NETVTGTWQG PHVVGLLTTL NFGDGPDRNK    60
TQTFQAKIHG SQIGLTGSSA GESVLVTARV ASGRTPGTCL YFSGVPKVLP SSQPPISCSE   120
EGVGNATLSP VMGEECVRVW SHERLVLTEL LTSEELALCG S                      161

SEQ ID NO: 127            moltype = AA  length = 30
FEATURE                   Location/Qualifiers
REGION                    1..30
                          note = synthetic
source                    1..30
                          mol_type = protein
                          organism = synthetic construct
SEQUENCE: 127
QIQLVQSGAE VKKPGASVKV SCKASGYTFT                                    30

SEQ ID NO: 128            moltype = AA  length = 14
FEATURE                   Location/Qualifiers
REGION                    1..14
                          note = synthetic
source                    1..14
                          mol_type = protein
                          organism = synthetic construct
SEQUENCE: 128
WVRQAPGQGL EWMG                                                     14

SEQ ID NO: 129            moltype = AA  length = 32
FEATURE                   Location/Qualifiers
REGION                    1..32
                          note = synthetic
source                    1..32
                          mol_type = protein
                          organism = synthetic construct
SEQUENCE: 129
RVTMTTDTST STAYMELRSL RSDDTAVYYC AR                                 32

SEQ ID NO: 130            moltype = AA  length = 11
FEATURE                   Location/Qualifiers
REGION                    1..11
                          note = synthetic
source                    1..11
                          mol_type = protein
                          organism = synthetic construct
SEQUENCE: 130
WGQGTLVTVS S                                                        11

SEQ ID NO: 131            moltype = AA  length = 25
FEATURE                   Location/Qualifiers
REGION                    1..25
                          note = synthetic
source                    1..25
                          mol_type = protein
                          organism = synthetic construct
SEQUENCE: 131
QIQLVQSGAE VKKPGASVKV SCKAS                                         25

SEQ ID NO: 132            moltype = AA  length = 8
FEATURE                   Location/Qualifiers
REGION                    1..8
                          note = synthetic
source                    1..8
                          mol_type = protein
                          organism = synthetic construct
SEQUENCE: 132
GYTFTSYG                                                             8

SEQ ID NO: 133            moltype = AA  length = 17
FEATURE                   Location/Qualifiers
REGION                    1..17
                          note = synthetic
source                    1..17
                          mol_type = protein
                          organism = synthetic construct
```

```
SEQUENCE: 133
ISWVRQAPGQ GLEWMGW                                                  17

SEQ ID NO: 134          moltype = AA  length = 8
FEATURE                 Location/Qualifiers
REGION                  1..8
                        note = synthetic
source                  1..8
                        mol_type = protein
                        organism = synthetic construct
SEQUENCE: 134
ISAYNGNT                                                            8

SEQ ID NO: 135          moltype = AA  length = 38
FEATURE                 Location/Qualifiers
REGION                  1..38
                        note = synthetic
source                  1..38
                        mol_type = protein
                        organism = synthetic construct
SEQUENCE: 135
NYAQKLQGRV TMTTDTSTST AYMELRSLRS DDTAVYYC                            38

SEQ ID NO: 136          moltype = AA  length = 11
FEATURE                 Location/Qualifiers
REGION                  1..11
                        note = synthetic
source                  1..11
                        mol_type = protein
                        organism = synthetic construct
SEQUENCE: 136
ARWGRWLAHD Y                                                        11

SEQ ID NO: 137          moltype = AA  length = 11
FEATURE                 Location/Qualifiers
REGION                  1..11
                        note = synthetic
source                  1..11
                        mol_type = protein
                        organism = synthetic construct
SEQUENCE: 137
WGQGTLVTVS S                                                        11

SEQ ID NO: 138          moltype = AA  length = 29
FEATURE                 Location/Qualifiers
REGION                  1..29
                        note = synthetic
source                  1..29
                        mol_type = protein
                        organism = synthetic construct
SEQUENCE: 138
QIQLVQSGAE VKKPGASVKV SCKASGYTF                                     29

SEQ ID NO: 139          moltype = AA  length = 7
FEATURE                 Location/Qualifiers
REGION                  1..7
                        note = synthetic
source                  1..7
                        mol_type = protein
                        organism = synthetic construct
SEQUENCE: 139
GYTFTSY                                                             7

SEQ ID NO: 140          moltype = AA  length = 10
FEATURE                 Location/Qualifiers
REGION                  1..10
                        note = synthetic
source                  1..10
                        mol_type = protein
                        organism = synthetic construct
SEQUENCE: 140
GYTFTSYGIS                                                          10

SEQ ID NO: 141          moltype = AA  length = 6
FEATURE                 Location/Qualifiers
REGION                  1..6
                        note = synthetic
source                  1..6
                        mol_type = protein
```

```
                                organism = synthetic construct
SEQUENCE: 141
TSYGIS                                                                        6

SEQ ID NO: 142          moltype = AA   length = 19
FEATURE                 Location/Qualifiers
REGION                  1..19
                        note = synthetic
source                  1..19
                        mol_type = protein
                        organism = synthetic construct
SEQUENCE: 142
GISWVRQAPG QGLEWMGWI                                                         19

SEQ ID NO: 143          moltype = AA   length = 11
FEATURE                 Location/Qualifiers
REGION                  1..11
                        note = synthetic
source                  1..11
                        mol_type = protein
                        organism = synthetic construct
SEQUENCE: 143
WVRQAPGQGL E                                                                 11

SEQ ID NO: 144          moltype = AA   length = 6
FEATURE                 Location/Qualifiers
REGION                  1..6
                        note = synthetic
source                  1..6
                        mol_type = protein
                        organism = synthetic construct
SEQUENCE: 144
SAYNGN                                                                        6

SEQ ID NO: 145          moltype = AA   length = 10
FEATURE                 Location/Qualifiers
REGION                  1..10
                        note = synthetic
source                  1..10
                        mol_type = protein
                        organism = synthetic construct
SEQUENCE: 145
WISAYNGNTN                                                                   10

SEQ ID NO: 146          moltype = AA   length = 13
FEATURE                 Location/Qualifiers
REGION                  1..13
                        note = synthetic
source                  1..13
                        mol_type = protein
                        organism = synthetic construct
SEQUENCE: 146
WMGWISAYNG NTN                                                               13

SEQ ID NO: 147          moltype = AA   length = 41
FEATURE                 Location/Qualifiers
REGION                  1..41
                        note = synthetic
source                  1..41
                        mol_type = protein
                        organism = synthetic construct
SEQUENCE: 147
TNYAQKLQGR VTMTTDTSTS TAYMELRSLR SDDTAVYYCA R                                 41

SEQ ID NO: 148          moltype = AA   length = 39
FEATURE                 Location/Qualifiers
REGION                  1..39
                        note = synthetic
source                  1..39
                        mol_type = protein
                        organism = synthetic construct
SEQUENCE: 148
YAQKLQGRVT MTTDTSTSTA YMELRSLRSD DTAVYYCAR                                    39

SEQ ID NO: 149          moltype = AA   length = 37
FEATURE                 Location/Qualifiers
REGION                  1..37
                        note = synthetic
source                  1..37
```

```
                        mol_type = protein
                        organism = synthetic construct
SEQUENCE: 149
YAQKLQGRVT MTTDTSTSTA YMELRSLRSD DTAVYYC                              37

SEQ ID NO: 151          moltype = AA   length = 10
FEATURE                 Location/Qualifiers
REGION                  1..10
                        note = synthetic
source                  1..10
                        mol_type = protein
                        organism = synthetic construct
SEQUENCE: 150
ARWGRWLAHD                                                            10

SEQ ID NO: 151          moltype = AA   length = 12
FEATURE                 Location/Qualifiers
REGION                  1..12
                        note = synthetic
source                  1..12
                        mol_type = protein
                        organism = synthetic construct
SEQUENCE: 151
YWGQGTLVTV SS                                                         12

SEQ ID NO: 152          moltype = AA   length = 22
FEATURE                 Location/Qualifiers
REGION                  1..22
                        note = synthetic
source                  1..22
                        mol_type = protein
                        organism = synthetic construct
SEQUENCE: 152
QAVLTQPPSV SVSPGQTASI TC                                              22

SEQ ID NO: 153          moltype = AA   length = 28
FEATURE                 Location/Qualifiers
REGION                  1..28
                        note = synthetic
source                  1..28
                        mol_type = protein
                        organism = synthetic construct
SEQUENCE: 153
QAVLTQPPSV SVSPGQTASI TCSGDKLG                                        28

SEQ ID NO: 154          moltype = AA   length = 25
FEATURE                 Location/Qualifiers
REGION                  1..25
                        note = synthetic
source                  1..25
                        mol_type = protein
                        organism = synthetic construct
SEQUENCE: 154
QAVLTQPPSV SVSPGQTASI TCSGD                                           25

SEQ ID NO: 155          moltype = AA   length = 7
FEATURE                 Location/Qualifiers
REGION                  1..7
                        note = synthetic
source                  1..7
                        mol_type = protein
                        organism = synthetic construct
SEQUENCE: 155
NKNAYWY                                                                7

SEQ ID NO: 156          moltype = AA   length = 6
FEATURE                 Location/Qualifiers
REGION                  1..6
                        note = synthetic
source                  1..6
                        mol_type = protein
                        organism = synthetic construct
SEQUENCE: 156
KLGNKN                                                                 6

SEQ ID NO: 157          moltype = AA   length = 9
FEATURE                 Location/Qualifiers
REGION                  1..9
                        note = synthetic
```

```
source                    1..9
                          mol_type = protein
                          organism = synthetic construct
SEQUENCE: 157
QQKPGQSPV                                                                  9

SEQ ID NO: 158            moltype = AA   length = 17
FEATURE                   Location/Qualifiers
REGION                    1..17
                          note = synthetic
source                    1..17
                          mol_type = protein
                          organism = synthetic construct
SEQUENCE: 158
AYWYQQKPGQ SPVLVMY                                                        17

SEQ ID NO: 159            moltype = AA   length = 10
FEATURE                   Location/Qualifiers
REGION                    1..10
                          note = synthetic
source                    1..10
                          mol_type = protein
                          organism = synthetic construct
SEQUENCE: 159
LVMYQSTRRP                                                                10

SEQ ID NO: 160            moltype = AA   length = 32
FEATURE                   Location/Qualifiers
REGION                    1..32
                          note = synthetic
source                    1..32
                          mol_type = protein
                          organism = synthetic construct
SEQUENCE: 160
GIPERFSASN SGNTATLTIS GTQAMDEADY YC                                       32

SEQ ID NO: 161            moltype = AA   length = 33
FEATURE                   Location/Qualifiers
REGION                    1..33
                          note = synthetic
source                    1..33
                          mol_type = protein
                          organism = synthetic construct
SEQUENCE: 161
SGIPERFSAS NSGNTATLTI SGTQAMDEAD YYC                                      33

SEQ ID NO: 162            moltype = AA   length = 37
FEATURE                   Location/Qualifiers
REGION                    1..37
                          note = synthetic
source                    1..37
                          mol_type = protein
                          organism = synthetic construct
SEQUENCE: 162
TRRPSGIPER FSASNSGNTA TLTISGTQAM DEADYYC                                  37

SEQ ID NO: 163            moltype = AA   length = 10
FEATURE                   Location/Qualifiers
REGION                    1..10
                          note = synthetic
source                    1..10
                          mol_type = protein
                          organism = synthetic construct
SEQUENCE: 163
QAWDSSSGWE                                                                10

SEQ ID NO: 164            moltype = AA   length = 10
FEATURE                   Location/Qualifiers
REGION                    1..10
                          note = synthetic
source                    1..10
                          mol_type = protein
                          organism = synthetic construct
SEQUENCE: 164
FGGGTKLTVL                                                                10

SEQ ID NO: 165            moltype = AA   length = 11
FEATURE                   Location/Qualifiers
REGION                    1..11
```

```
                        note = synthetic
source                  1..11
                        mol_type = protein
                        organism = synthetic construct
SEQUENCE: 165
VFGGGTKLTV L                                                            11

SEQ ID NO: 166          moltype = AA   length = 11
FEATURE                 Location/Qualifiers
REGION                  1..11
                        note = synthetic
source                  1..11
                        mol_type = protein
                        organism = synthetic construct
SEQUENCE: 166
QAWLSSSGWE V                                                            11

SEQ ID NO: 167          moltype = AA   length = 11
FEATURE                 Location/Qualifiers
REGION                  1..11
                        note = synthetic
source                  1..11
                        mol_type = protein
                        organism = synthetic construct
SEQUENCE: 167
QAWDSSSGWE V                                                            11

SEQ ID NO: 168          moltype = AA   length = 118
FEATURE                 Location/Qualifiers
REGION                  1..118
                        note = synthetic
source                  1..118
                        mol_type = protein
                        organism = synthetic construct
SEQUENCE: 168
QIQLVQSGAE VKQPGASVSV SCAASGYTFT SYGISWVRQA PGQGLEWMGW ISAYNGNTNY        60
AQKLQGRVTM TTDTSTSTAY MELSSLRSDD TAVYYCARWG RWLAHDYWGQ GTLVTVSS        118

SEQ ID NO: 169          moltype = AA   length = 118
FEATURE                 Location/Qualifiers
REGION                  1..118
                        note = synthetic
source                  1..118
                        mol_type = protein
                        organism = synthetic construct
SEQUENCE: 169
QIQLVQSGAE VKQPGASVSV SCAASGYTFT SYGISWVRQA PGQGLEWMGW ISAYNGNTNY        60
AQKLQGRVTM TTDTSTSTAY MELSSLRSDD TAVYYCARWG RWLAHDYWGQ GTLVTVSS        118

SEQ ID NO: 170          moltype = AA   length = 118
FEATURE                 Location/Qualifiers
REGION                  1..118
                        note = synthetic
source                  1..118
                        mol_type = protein
                        organism = synthetic construct
SEQUENCE: 170
QIQLVQSGAE VKQPGASVSV SCAASGYTFT SYGISWVRQA PGQGLEWMGW ISAYNGNTNY        60
AQKLQGRVTM TTDTSTSTAY MELSSLRSDD TAVYYCARWG RWLAHDYWGQ GTLVTVSS        118

SEQ ID NO: 171          moltype = AA   length = 108
FEATURE                 Location/Qualifiers
REGION                  1..108
                        note = synthetic
source                  1..108
                        mol_type = protein
                        organism = synthetic construct
SEQUENCE: 171
QAVLTQPPSV SVSPGQTASI TCSGDKLGNK NAYWYQQKPG QSPVLVMYQS TRRPSGIPER        60
FSASNSGNTA TLTISGTQAM DEADYYCQAW LSSSGWEVFG GGTKLTVL                  108

SEQ ID NO: 172          moltype = AA   length = 108
FEATURE                 Location/Qualifiers
REGION                  1..108
                        note = synthetic
source                  1..108
                        mol_type = protein
                        organism = synthetic construct
SEQUENCE: 172
```

```
QAVLTQPPSV SVSPGQTASI TCSGDKLGNK NAYWYQQKPG QSPVLVMYQS TRRPSGIPER    60
FSASNSGNTA TLTISGTQAE DEADYYCQAW DSSSGWEVFG GGTKLTVL              108

SEQ ID NO: 173          moltype = AA  length = 108
FEATURE                 Location/Qualifiers
REGION                  1..108
                        note = synthetic
source                  1..108
                        mol_type = protein
                        organism = synthetic construct
SEQUENCE: 173
QAVLTQPPSV SVSPGQTASI TCSGDKLGNK NAYWYQQKPG QSPVLVMYQS TRRPSGIPER    60
FSASNSGNTA TLTISGTQAM DEADYYCQAW DSSSGWEVFG GGTKLTVL              108

SEQ ID NO: 174          moltype = DNA  length = 1335
FEATURE                 Location/Qualifiers
misc_feature            1..1335
                        note = synthetic
source                  1..1335
                        mol_type = other DNA
                        organism = synthetic construct
SEQUENCE: 174
cagatccagt tggtgcaaag tggggctgag gtaaagcagc cgggtgcaag tgtgtccgta    60
agttgtgcag ccagtggcta cacctttact agttacggaa tttcatgggt gcggcaagct   120
cccggtcagg gattggaatg gatgggatgg atttcagcat acaacgggaa cacaaattac   180
gctcaaaaat tgcagggtcg agttaccatg actacagaca cgtctacgtc tacagcttac   240
atggaacttt ccagcctgcg gtccgacgac accgcagttt attattgcgc ccgctggggg   300
agatggctcg cgcatgacta ctgggggcag ggcacgctgg ttaccgtttc ctcagcctcc   360
accaagggcc catccgtctt cccccctggcg ccctgctcca ggagcacctc cgagagcaca   420
gccgccctgg gctgcctggt caaggactac ttccccgaac cggtgacggt gtcgtggaac   480
tcaggcgccc tgaccagcgg cgtgcacacc ttccggctg tcctacagtc ctcaggactc   540
tactccctca gcagcgtggt gaccgtgccc tccagcagct tgggcacgaa gacctacacc   600
tgcaacgtag atcacaagcc cagcaacacc aaggtggaca gagagttga gtccaaatat   660
ggtcccccat gcccacctg cccagcacct gagttcgagg gggaccatc agtcttcctg   720
ttcccccaa aacccaagga cactctcatg atctcccgga ccctgaggt cacgtgcgtg   780
gtggtggacg tgagccagga agaccccgag gtccagttca ctggtacgt ggatggcgtg   840
gaggtgcata atgccaagac aaagccgcgg gaggagcagt tcaacagcac gtaccgtgtg   900
gtcagcgtcc tcaccgtcct gcaccaggac tggctgaacg gcaaggagta caagtgcaag   960
gtgtccaaca aaggcctccc gtcctccatc gagaaaacca tctccaaagc caaagggcag  1020
ccccgagagc cacaggtgta caccctgccc ccatcccagg aggagatgac caagaaccag  1080
gtcagcctga cctgcctggt caaaggcttc taccccagcg acatcgccgt ggagtgggag  1140
agcaatgggc agccggagaa caactacaag accacgcctc ccgtgctgga ctccgacggc  1200
tccttcttcc tctacagcag gctaaccgtg gacaagagca ggtggcagga ggggaatgtc  1260
ttctcatgct ccgtgatgca tgaggctctg cacaaccact acacacagaa gagtctctcc  1320
ctgtctctgg gtaaa                                                   1335

SEQ ID NO: 175          moltype = DNA  length = 1335
FEATURE                 Location/Qualifiers
misc_feature            1..1335
                        note = synthetic
source                  1..1335
                        mol_type = other DNA
                        organism = synthetic construct
SEQUENCE: 175
cagatccagt tggtgcaaag tggggctgag gtaaagcagc cgggtgcaag tgtgtccgta    60
agttgtgcag ccagtggcta cacctttact agttacggaa tttcatgggt gcggcaagct   120
cccggtcagg gattggaatg gatgggatgg atttcagcat acaacgggaa cacaaattac   180
gctcaaaaat tgcagggtcg agttaccatg actacagaca cgtctacgtc tacagcttac   240
atggaacttt ccagcctgcg gtccgacgac accgcagttt attattgcgc ccgctggggg   300
agatggctcg cgcatgacta ctgggggcag ggcacgctgg ttaccgtttc ctcagcctcc   360
accaagggcc catccgtctt cccccctggcg ccctgctcca ggagcacctc cgagagcaca   420
gccgccctgg gctgcctggt caaggactac ttccccgaac cggtgacggt gtcgtggaac   480
tcaggcgccc tgaccagcgg cgtgcacacc ttccggctg tcctacagtc ctcaggactc   540
tactccctca gcagcgtggt gaccgtgccc tccagcagct tgggcacgaa gacctacacc   600
tgcaacgtag atcacaagcc cagcaacacc aaggtggaca gagagttga gtccaaatat   660
ggtcccccat gcccacctg cccagcacct gagttcgagg gggaccatc agtcttcctg   720
ttcccccaa aacccaagga cactctcatg atctcccgga ccctgaggt cacgtgcgtg   780
gtggtggacg tgagccagga agaccccgag gtccagttca ctggtacgt ggatggcgtg   840
gaggtgcata atgccaagac aaagccgcgg gaggagcagt tcaacagcac gtaccgtgtg   900
gtcagcgtcc tcaccgtcct gcaccaggac tggctgaacg gcaaggagta caagtgcaag   960
gtgtccaaca aaggcctccc gtcctccatc gagaaaacca tctccaaagc caaagggcag  1020
ccccgagagc cacaggtgta caccctgccc ccatcccagg aggagatgac caagaaccag  1080
gtcagcctga cctgcctggt caaaggcttc taccccagcg acatcgccgt ggagtgggag  1140
agcaatgggc agccggagaa caactacaag accacgcctc ccgtgctgga ctccgacggc  1200
tccttcttcc tctacagcag gctaaccgtg gacaagagca ggtggcagga ggggaatgtc  1260
ttctcatgct ccgtgatgca tgaggctctg cacaaccact acacacagaa gagtctctcc  1320
ctgtctctgg gtaaa                                                   1335

SEQ ID NO: 176          moltype = DNA  length = 1335
```

```
FEATURE              Location/Qualifiers
misc_feature         1..1335
                     note = synthetic
source               1..1335
                     mol_type = other DNA
                     organism = synthetic construct
SEQUENCE: 176
cagatccagt tggtgcaaag tggggctgag gtaaagcagc cgggtgcaag tgtgtccgta    60
agttgtgcag ccagtggcta cacctttact agttacgtaa tttcatgggt gcggcaagct   120
cccggtcagg gattggaatg gatgggatgg atttcagcat acaacgggaa cacaaattac   180
gctcaaaaat tgcagggtcg agttaccatg actacagaca cgtctacgtc tacagcttac   240
atggaacttt ccagcctgcg gtccgacgac accgcagttt attattgcgc ccgctggggg   300
agatggctcg cgcatgacta ctgggggcag ggcacgctgg ttaccgtttc ctcagcctcc   360
accaagggcc catccgtctt cccccctggcg ccctgctcca cgagagcaca               420
gccgccctgg gctgcctggt caaggactac ttccccgaac cggtgacggt gtcgtggaac   480
tcaggcgccc tgaccagcgg cgtgcacacc ttccggctg tcctacagtc tcaggactc    540
tactccctca gcagcgtggt gaccgtgccc tccagcagct gggcacgaa gacctacacc    600
tgcaacgtag atcacaagcc cagcaacacc aaggtggaca agagagttga gtccaaatat   660
ggtcccccat gcccaccctg cccagcacct gagttcgagg ggggaccatc agtcttcctg   720
ttccccccaa acccaaggga cactctcatg atctcccgga cccctgaggt cacgtgcgtg   780
gtggtggacg tgagccagga agaccccgag gtccagttca actggtacgt ggatggcgtg   840
gaggtgcata atgccaagac aaagccgcgg gaggagcagt tcaacagcac gtaccgtgtg   900
gtcagcgtcc tcaccgtcct gcaccaggac tggctgaacg gcaaggagta caagtgcaag   960
gtgtccaaca aggcctcccg tcctccatc gagaaaacca ctccaaagc caagggcag     1020
cccgagagc cacaggtgta cccctgccc catcccagg aggagatgac caagaaccag    1080
gtcagcctga cctgcctggt caaggcttc taccccagcg acatcgccgt ggagtgggag   1140
agcaatgggc agccggagaa caactacaag accacgcctc ccgtgctgga ctccgacggc   1200
tccttcttcc tctacagcag gctaaccgtg gacaagagca ggtggcagga ggggaatgtc   1260
ttctcatgct ccgtgatgca tgaggctctg cacaaccact acacacagaa gagtctctcc   1320
ctgtctctgg gtaaa                                                   1335

SEQ ID NO: 177       moltype = DNA  length = 642
FEATURE              Location/Qualifiers
misc_feature         1..642
                     note = synthetic
source               1..642
                     mol_type = other DNA
                     organism = synthetic construct
SEQUENCE: 177
caggcggtgc ttactcagcc cccaagtgtg tctgtttccc ccggtcagac tgcgtctata    60
acctgctccg gggataaaact cggcaacaag aatgcgtact ggtaccaaca gaagccggga   120
cagagcccag tcttggtcat gtaccaatcc acccggagac ctagcggcat tccagagcgc   180
tttagtgtca ctaattctgg caatacggcg acgttgacca tcagtggtac acaagcggta   240
gacgaggcag attactactg tcaggcatgg ctgtcatcat ccgggtggga ggtgtttggc   300
ggcggaacaa aactcactgt cctaggtcag cccaaggctg caccaagtgt cactctgttc   360
ccgccctcct ctgaggagct tcaagccaac aaggccacac tggtgtgtct cataagtgac   420
ttctacccgg gagccgtgac agtggcctgg aaggcagata gcagcccgt caaggcggga    480
gtggagacca ccacaccctc caaacaaagc aacaacaagt acgcggccag cagctatctg   540
agcctgacgc ctgagcagtg gaagtccac agaagctaca gctgccaggt cacgcatgaa    600
gggagcaccg tggagaagac agtggcccct acagaatgtt ca                      642

SEQ ID NO: 178       moltype = DNA  length = 642
FEATURE              Location/Qualifiers
misc_feature         1..642
                     note = synthetic
source               1..642
                     mol_type = other DNA
                     organism = synthetic construct
SEQUENCE: 178
caggccgtct tgactcaacc accctccgtt agtgtctccc ccggccagac ggcgagtatc    60
acctgtagtg gtgataagct gggcaataag aatgcttact ggtaccagca aaaacccgga   120
cagagcccag tgctggtgat gtatcagtct acaagacgac ctagcggcat cccagaaagg   180
tttttctgcca gcaattctgg caatacggcg acgctgacta ttagtggcac acaagcagag   240
gatgaggcgg actattactg ccaagcatgg gacagtagtg gtgttggga agtcttcggg   300
ggcggcacta agctcaccgt cctaggtcag cccaaggctg caccaagtgt cactctgttc   360
ccgccctcct ctgaggagct tcaagccaac aaggccacac tggtgtgtct cataagtgac   420
ttctacccgg gagccgtgac agtggcctgg aaggcagata gcagcccgt caaggcggga    480
gtggagacca ccacaccctc caaacaaagc aacaacaagt acgcggccag cagctatctg   540
agcctgacgc ctgagcagtg gaagtccac agaagctaca gctgccaggt cacgcatgaa    600
gggagcaccg tggagaagac agtggcccct acagaatgtt ca                      642

SEQ ID NO: 179       moltype = DNA  length = 642
FEATURE              Location/Qualifiers
misc_feature         1..642
                     note = synthetic
source               1..642
                     mol_type = other DNA
                     organism = synthetic construct
SEQUENCE: 179
```

-continued

```
caagctgtat tgacacaacc tcctagtgtc agtgtaagcc ctggtcaaac tgcctccatt    60
acttgctctg gcgacaagct cggaaataag aacgcgtact ggtaccaaca gaagcccgga   120
cagtcacctg tgcttgttat gtatcaaagc accaggagac cttcagggat accagaaagg   180
tttagtgcgt ctaattccgg gaataccgcg acactgacga taagcggcac tcaggctatg   240
gacgaagcgg attactactg tcaggcatgg gattcatcat caggttggga agtattcggg   300
ggcggtacaa aattgacggt cctaggtcag cccaaggctg caccaagtgt cactctgttc   360
ccgccctcct ctgaggagct tcaagccaac aaggccacac tggtgtgtct cataagtgac   420
ttctacccgg gagccgtgac agtggcctgg aaggcagata gcagcccgt caaggcggga    480
gtggagacca ccacaccctc caaacaaagc aacaacaagt acgcggccag cagctatctg   540
agcctgacgc ctgagcagtg gaagtccac agaagctaca gctgccaggt cacgcatgaa    600
gggagcaccg tggagaagac agtggcccct acagaatgtt ca                     642
```